(12) United States Patent
Talebpour et al.

(10) Patent No.: US 10,662,420 B2
(45) Date of Patent: *May 26, 2020

(54) APPARATUS AND METHOD FOR EXTRACTING MICROBIAL CELLS

(71) Applicant: QVELLA CORPORATION, Richmond Hill (CA)

(72) Inventors: Samad Talebpour, Richmond Hill (CA); Aye Aye Khine, Thornhill (CA); Robert Maaskant, King City (CA); Tino Alavie, Thornhill (CA)

(73) Assignee: QVELLA CORPORATION, Richmond Hill, ON (CA)

( * ) Notice: Subject to any disclaimer, the term of this patent is extended or adjusted under 35 U.S.C. 154(b) by 197 days.

This patent is subject to a terminal disclaimer.

(21) Appl. No.: 15/612,091

(22) Filed: Jun. 2, 2017

(65) Prior Publication Data

US 2017/0275612 A1     Sep. 28, 2017

Related U.S. Application Data

(63) Continuation-in-part of application No. 14/648,161, filed as application No. PCT/CA2013/000992 on Nov. 26, 2013, now Pat. No. 9,707,555, which is a continuation-in-part of application No. 13/833,872, filed on Mar. 15, 2013, now Pat. No. 8,975,060.

(60) Provisional application No. 61/750,242, filed on Jan. 8, 2013, provisional application No. 61/731,809, filed on Nov. 30, 2012.

(51) Int. Cl.
*C12Q 1/68* (2018.01)
*B01L 3/00* (2006.01)
*B01L 7/00* (2006.01)
*C12N 15/10* (2006.01)
*C12Q 1/6806* (2018.01)
*C12Q 1/24* (2006.01)

(52) U.S. Cl.
CPC ........ *C12N 15/1003* (2013.01); *B01L 3/5021* (2013.01); *B01L 3/5027* (2013.01); *C12Q 1/24* (2013.01); *C12Q 1/6806* (2013.01)

(58) Field of Classification Search
None
See application file for complete search history.

(56) References Cited

FOREIGN PATENT DOCUMENTS

EP    0107070 B1    11/1988

*Primary Examiner* — Robert J Yamasaki
*Assistant Examiner* — Charles Z Constantine
(74) *Attorney, Agent, or Firm* — Hill & Schumacher

(57) ABSTRACT

Methods and devices are provided for pre-treatment of a sample containing microbial cells. In some embodiments, the pre-treatment of the sample is performed via the initial selective lysis, within a sample pre-treatment vessel, of non-microbial cells, such as blood cells, and the subsequent centrifugal separation of the sample to remove the resulting debris and concentrate the microbial cells. An immiscible and dense cushioning liquid may be included for collecting the microbial cells adjacent to the liquid interface formed by the cushioning liquid upon centrifugation of the pre-treatment vessel. After removal of a substantial quantity of the supernatant, resuspension of the collected microbial cells, and re-establishment of the cushioning liquid interface, at least a portion of the remaining suspension may be removed without substantially removing the cushioning liquid. One or more intermediate wash cycles may be performed prior to extraction of the remaining suspension, which provides a "pretreated" sample.

34 Claims, 35 Drawing Sheets

Specification includes a Sequence Listing.

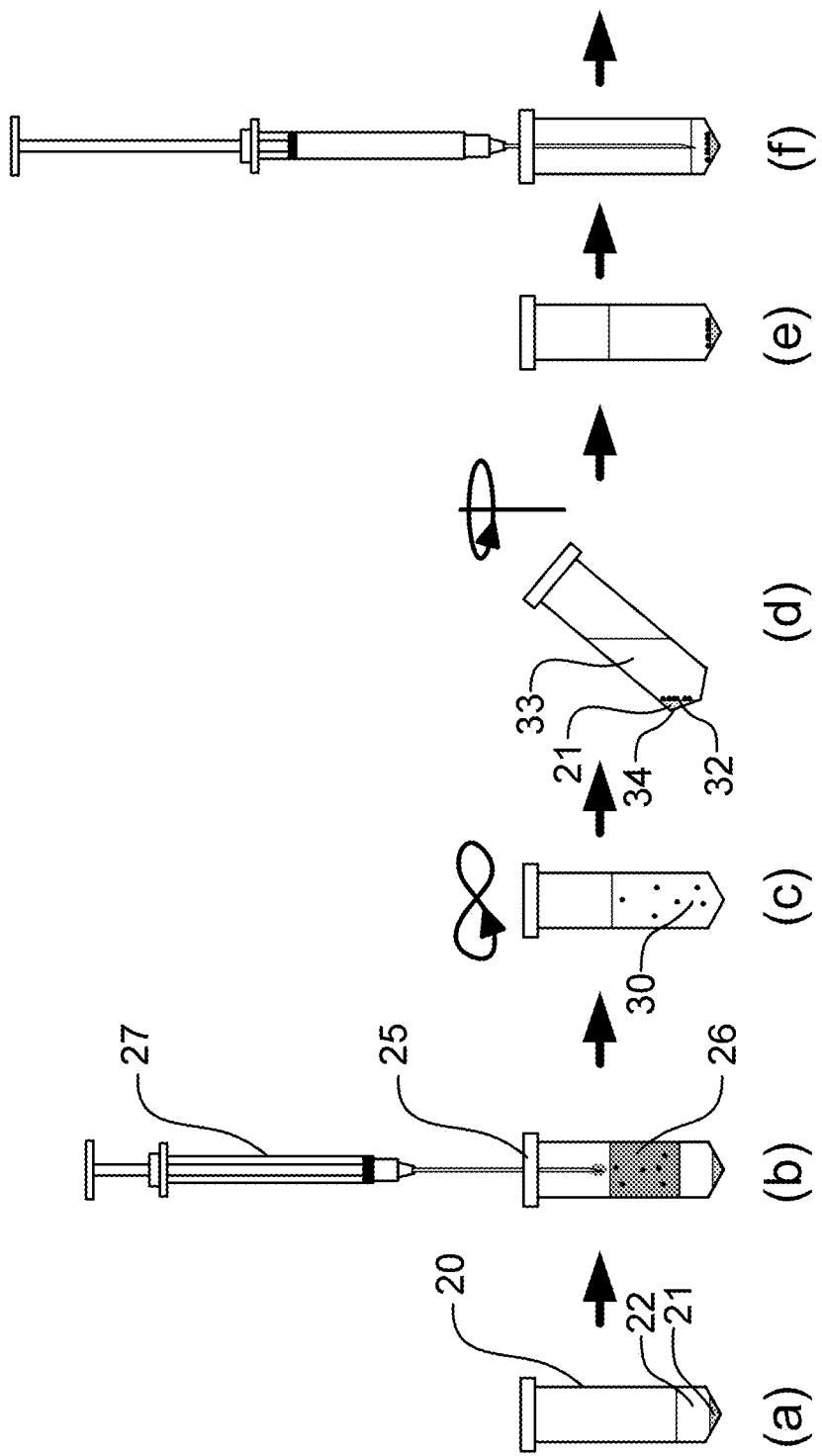
Figure 1 (a)-(f)

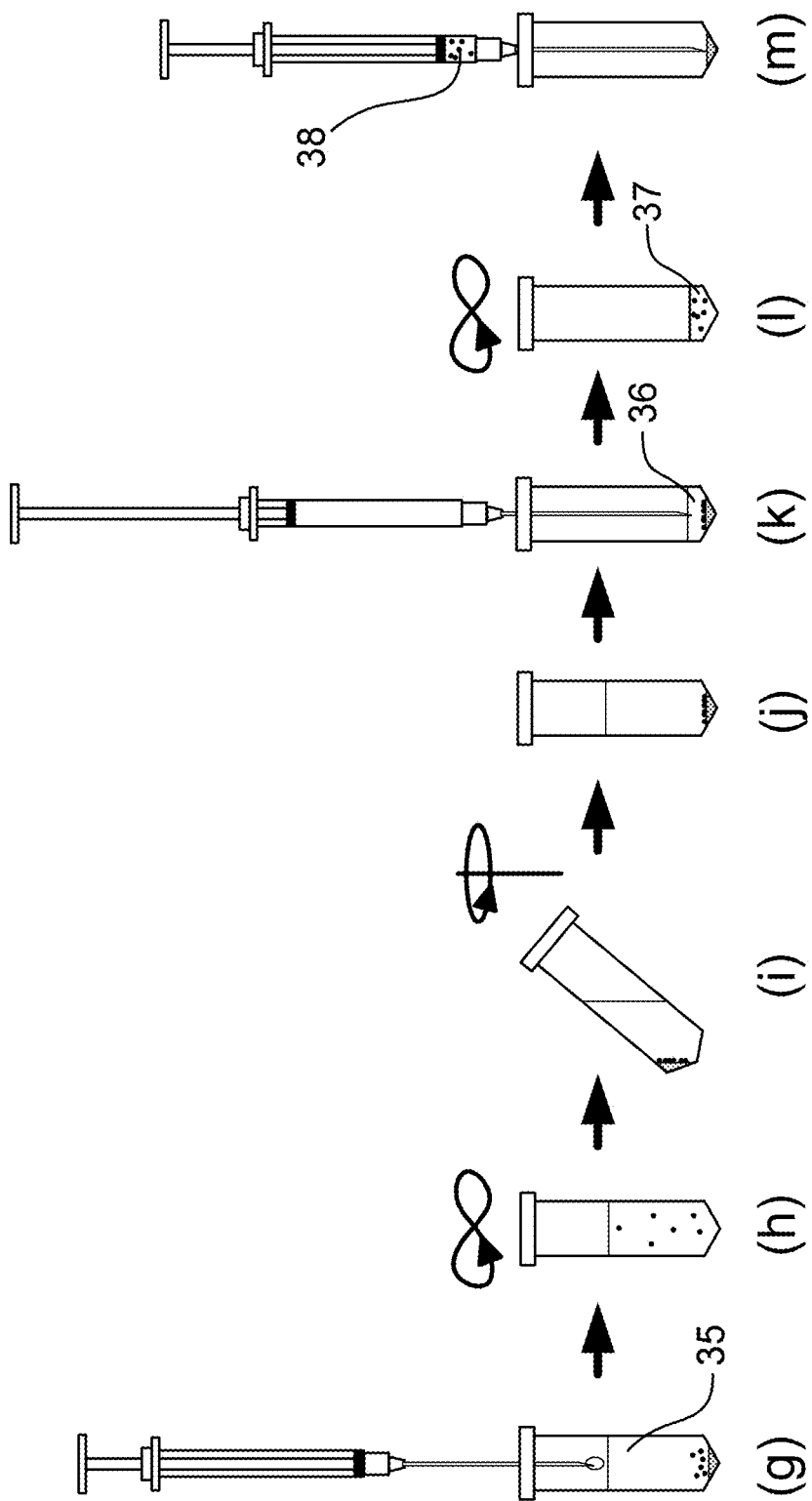
Figure 1 (g)-(m)

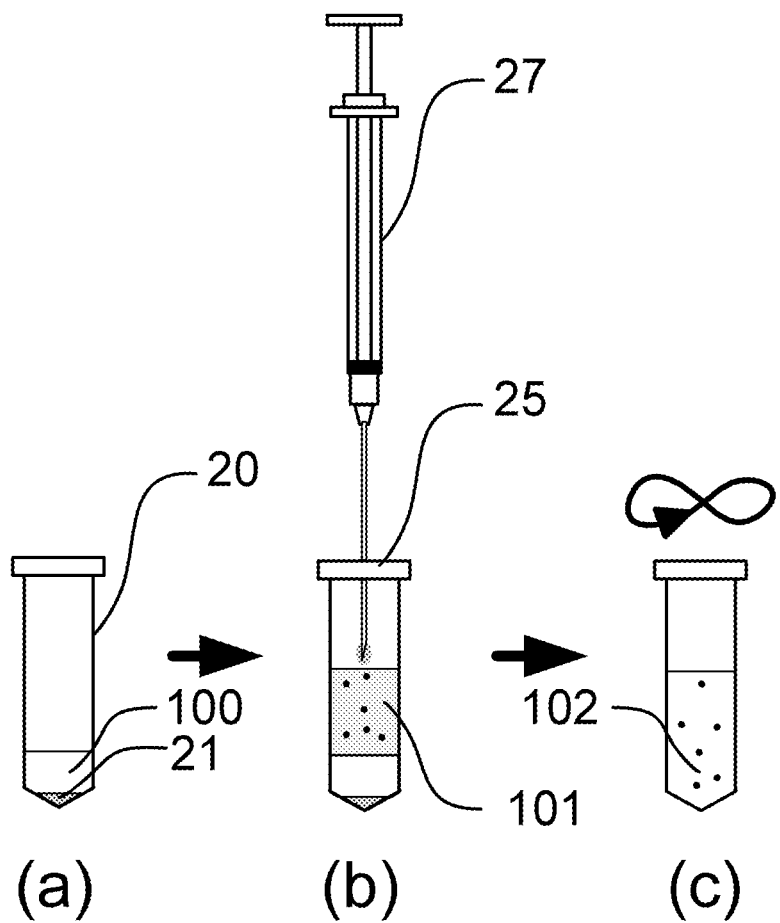
Figures 2(a)-(c)

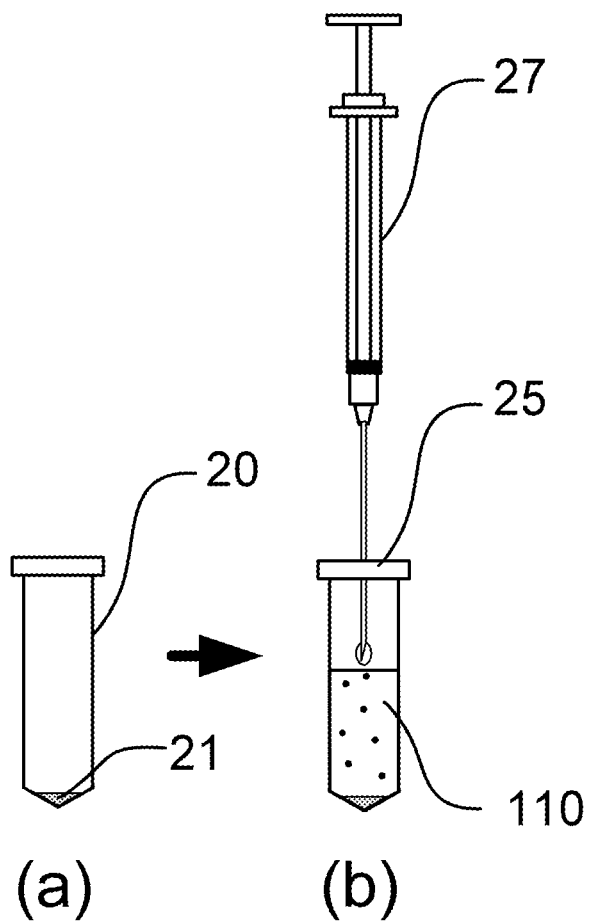
Figures 3(a) and (b)

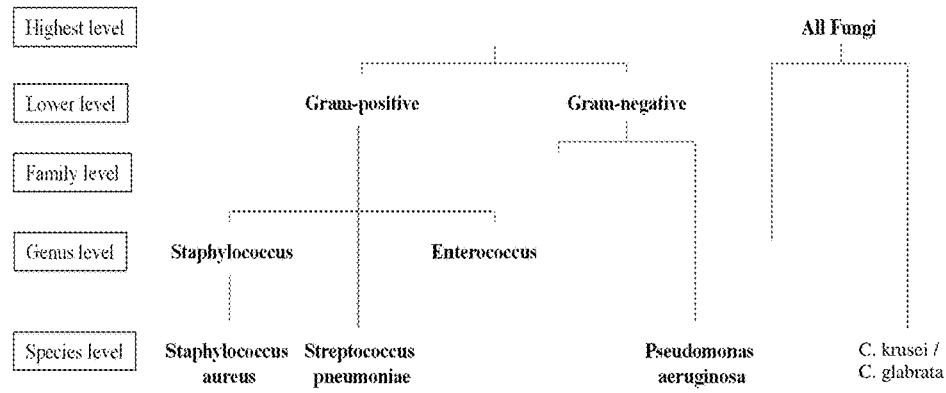

Figure 9(a)

| | Gram + | Gram - | Fung. | Staph. | Staph. aureus | Entero-coccus | Strep pneu. | Pseud. aerug. | C. Kru. /Gla. | Organ-ism | Example Antibiotic |
|---|---|---|---|---|---|---|---|---|---|---|---|
| 1 | ▓ | | | ▓ | ▓ | | | | | Staph. aureus | Vanco + oxacillin |
| 2 | ▓ | | | ▓ | | | | | | Other Staph. | Suspect contaminant |
| 3 | ▓ | | | | | | ▓ | | | Strep. pneu. | Vanco+ Ceftriax-one |
| 4 | ▓ | | | | | ▓ | | | | Enterro-coccus | Vanco + ampicillin |
| 5 | ▓ | | | | | | | | | Other Strep. | Ampicillin |
| 6 | | ▓ | | | | | | | | Entero-bacteria | Erapenem |
| 7 | | ▓ | | | | | | ▓ | | P. aeru. | Ceftizoxi-me |
| 8 | | | ▓ | | | | | | | Other fungi | Fluconaz-ole |
| 9 | | | ▓ | | | | | | ▓ | C. Krusei C. glabrata | Mycafun-gin |

Figure 9(b)

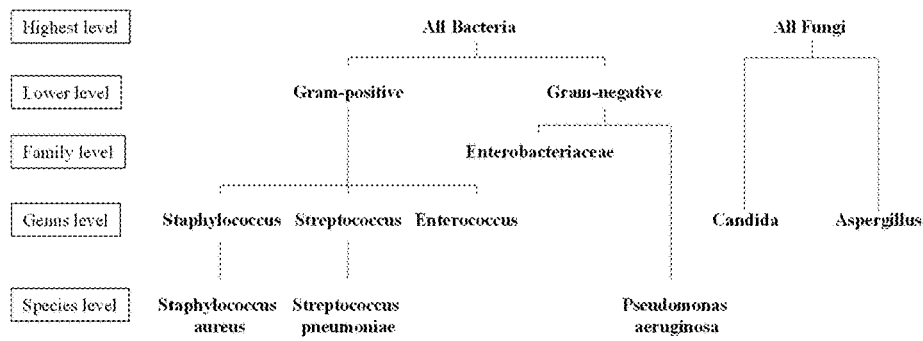

Figure 10(a)

| C-albicans Samples/Controls | Fluorescence intensity |
|---|---|
| negative control; buffer | 94 |
| negative control; blood | 88 |
| 1 cell-positive control | 131 |
| 1 cell-spiked blood sample | 129 |
| 1 cell-spiked blood sample | 140 |
| 10 cells-positive control | 151 |
| 10 cell-spiked blood sample | 146 |

Figure 17

| S.pneumoniae Samples/Controls | Fluorescence intensity |
|---|---|
| negative control; buffer | 110 |
| negative control; blood | 112 |
| 1 cell-positive control | 159 |
| 1 cell-spiked blood sample | 126 |
| 1 cell-spiked blood sample | 142 |
| 10 cells-positive control | 177 |
| 10 cell-spiked blood sample | 134 |
| 10 cell-spiked blood sample | 165 |

Figure 19

| E.coli Samples/Controls | Fluorescence intensity |
|---|---|
| negative control; buffer | 113 |
| negative control; blood | 110 |
| 1 cell-positive control | 146 |
| 1 cell-spiked blood sample | 131 |
| 1 cell-spiked blood sample | 129 |
| 10 cells-positive control | 151 |
| 10 cell-spiked blood sample | 145 |
| 10 cell-spiked blood sample | 149 |

Figure 21

| Highest level | Lower level | Family level | Genus level | Species level | Microbial cells tested |
|---|---|---|---|---|---|
| All bacteria | Gram-positive | | Staphylococcus | *Staphylococcus aureus* | *Staphylococcus aureus* |
| | | | Streptococcus | *Streptococcus pneumoniae* | *Streptococcus pneumoniae* |
| | | | Other Streptococcus | | *Streptococcus pyogenes* *Streptococcus sanguis* |
| | | | Enterococcus | | *Enterococcus faecalis* |
| | Gram-negative | Enterobacteriacae | | | *Escherichia coli* *Klebsiella pneumoniae* *Enterobacter cloacae* *Acinetobacter baumanni* |
| | | | | *Pseudomonas aeruginosa* | *Pseudomonas aeruginosa* |
| All fungi | | | | | *Candida albicans* *Candida glabrata* *Candida krusei* *Cryptococcus neoformans* |
| | | | Aspergillus | | *Aspergillus fumigatus* |

Figure 22

| Target | Primer | Sequence | Amplicon size |
|---|---|---|---|
| Gram-Negative | GNF8 | 5'-GTTACCCGCAGAAGAAGCACCG-3' (SEQ ID NO: 23) | 151 |
| | GNR8 | 5'-ATGCAGTTCCCAGGTTGAGCC-3' (SEQ ID NO: 24) | |
| Gram-Positive | GPF8 | 5'-GCTCGTGTCGTGAGATGTTGGG-3' (SEQ ID NO: 21) | 151 |
| | GPR8 | 5'-CAGGTCATAAGGGGCATGATGAT-3' (SEQ ID NO: 22) | |
| Fungi | UFF2 | 5'- ACGGGGAGGTAGTGACAATAAAT-3' (SEQ ID NO: 9) | 190 |
| | UFR2 | 5'- CCCAAGGTTCAACTACGAGCTT-3' (SEQ ID NO: 10) | |

Figure 23

APPARATUS AND METHOD FOR EXTRACTING MICROBIAL CELLS

CROSS-REFERENCE TO RELATED APPLICATION

This application is a Continuation of a National Phase application 14/648,161, filed May 28, 2015, claiming the benefit of international PCT Patent Application No. PCT/CA2013/000992, filed on Nov. 26, 2013, in English, which claims priority to U.S. Provisional Application No. 61/731,809, titled "APPARATUS AND METHOD FOR PRE-TREATMENT OF MICROBIAL SAMPLES" and filed on Nov. 30, 2012, the entire contents of which is incorporated herein by reference, U.S. Provisional Application No. 61/750,242, titled "APPARATUS AND METHOD FOR PRE-TREATMENT OF MICROBIAL SAMPLES" and filed on Jan. 8, 2013, the entire contents of which is incorporated herein by reference, and to U.S. patent application Ser. No. 13/833,872, titled "APPARATUS AND METHOD FOR PRE-TREATMENT OF MICROBIAL SAMPLES" and filed on Mar. 15, 2013, the entire contents of which is incorporated herein by reference.

BACKGROUND

This disclosure relates to methods of detecting the presence and the identity of microorganisms in a sample.

Emergence of drug resistant pathogens is a global healthcare crisis that is forcing physicians to treat common infectious diseases with ever more potent antibiotics. This is largely caused by the complexity and time required in identifying the offending bacteria, forcing physicians to prescribe empirically even with the knowledge of the high negativity rate amongst cultured specimens. The net result has been a significant increase in emergence of resistant strains, higher treatment costs, and longer recovery cycle due to an increase in side effect risks associated with taking broad spectrum and unnecessary antibiotics.

Broad spectrum antibiotics are commonly prescribed when treating patients that are exhibiting symptoms of sepsis or septic shock. Given the seriousness of these conditions, doctors will often prescribe one or more broad-spectrum antibiotics right away and are not likely to change the treatment regimen until the full effect of the drugs can be assessed or results from microbiology become available. For instance, the document "Surviving Sepsis Campaign Guideline" (SSCG) recommends a treatment protocol in which intravenous antibiotics, consisting of one or more broad-spectrum agents against likely bacterial/fungal pathogens, should be started within the first hour of recognizing severe sepsis and septic shock [R. P. Dellinger et al., Crit. Care Med 2008]. The treatment protocol states that the antimicrobial regimen is to be reassessed daily, and once the pathogen is known, as a matter of good practice, a more appropriate narrow-spectrum antimicrobial drug is to be administered.

Unfortunately, current clinical bacteriology methods typically provide pathogen identification information when it may be too late to impact patient outcomes. This is due to the time lag of 2-3 days from specimen collection to reporting results of pathogen identification and susceptibility testing. Causes for the time lag include the need to transport specimens to clinical laboratories staffed by expert clinical bacteriologists and the time required for blood culture and subsequent colony formation after plating the specimen on solid culture medium. Specimens that arrive at the clinical microbiology laboratory after normal business hours are typically held overnight until staff arrives the next day. Once specimens are plated on solid agar on day 2 (after a positive blood culture has been obtained), an additional 8-12 hours are needed for colonies to form. Plates are examined, colonies are enumerated, and appropriate colonies are selected for identification and susceptibility testing. The process further requires analysis and interpretation before reports are released, typically on day 3, which may be too slow to meaningfully impact antibiotic selection and patient outcomes.

While many aspects of clinical microbiology laboratory workflow have been automated, clinical bacteriology remains highly labour-intensive. Many laboratories currently automate identification and susceptibility testing using either the Vitek (Biomerieux) or Phoenix (Becton-Dickenson) instruments. However, these systems, and newer systems based on mass spectroscopy, depend on selection of appropriate colonies from overnight growth on agar plates by expert personnel.

Several nucleic acid amplification approaches for clinical bacteriology have recently been commercialized. However, most of these still require a sample preparation process which includes a nucleic acid extraction and purification step that can take more than 3 hours, as part of the pre-analytical process for species identification. These processes are required for providing an inhibitor and contaminant free sample for nucleic acid assays. Consequently, despite their specificity and sensitivity, molecular methods such as PCR have not replaced the much slower standard microbial culture-based techniques as the front line test in the clinical microbiology laboratory, and the results from clinical microbiology testing continue to be provided too late to substantially impact patient outcomes.

SUMMARY

Methods and devices are provided for pretreatment of a sample containing microbial cells. In some embodiments, the pretreatment of the sample is performed via the initial selective lysis, within a sample pretreatment vessel, of non-microbial cells (such as blood cells) and the subsequent centrifugal separation of the sample to remove the resulting debris and concentrate the microbial cells. An immiscible and dense cushioning liquid may be included for collecting the microbial cells adjacent to the liquid interface formed by the cushioning liquid upon centrifugation of the pretreatment vessel. After removal of a substantial quantity of the supernatant, resuspension of the collected microbial cells, and re-establishment of the cushioning liquid interface, at least a portion of the remaining suspension may be removed without substantially removing the cushioning liquid. One or more intermediate wash cycles may be performed prior to extraction of the remaining suspension, which provides a "pretreated" sample.

The methods described herein may be useful in decreasing the time to result of nucleic assays for the identification of microbial cells by taking a different approach to the preparation of target nucleic acid suspension. In some embodiments disclosed herein that involve a whole blood sample, blood cells in the whole blood sample are selectively lysed and their resulting debris are washed away while the microbial cells are kept intact and collected. The cell suspension is thereby rendered substantially free of molecular assay interferents and inhibitors. Subsequently, the microbial cells may be lysed with a method that does not require lytic reagents, and the lysate, which has been rendered substantially free of molecular assay interferents and inhibitors, may be directly assayed, without nucleic acid extraction and purification.

Accordingly, in one aspect, there is provided a method of extracting microbial cells from a whole blood sample, the method comprising:

adding a whole blood sample to a pretreatment vessel, the pretreatment vessel comprising a pretreatment mixture, the pretreatment mixture comprising a blood cell lysis reagent and a hydrophobic cushioning liquid having a density greater than that of the whole blood sample and the blood cell lysis reagent;

agitating the contents of the pretreatment vessel;

centrifuging the pretreatment vessel such that the cushioning liquid forms a liquid interface below a supernatant, wherein microbial cells from the whole blood sample are removed from suspension and collected adjacent to the liquid interface;

withdrawing a substantial quantity of the supernatant without removing the collected microbial cells;

agitating the contents of the pretreatment vessel and allowing the cushioning liquid to re-establish the liquid interface below a suspension containing the microbial cells; and extracting a least a portion of the suspension without extracting a substantial portion of the cushioning liquid, thereby obtaining an extracted suspension comprising microbial cells.

In another aspect, there is provided a pretreatment vessel for extracting microbial cells from a whole blood sample, comprising:

a vessel body defining an internal volume and an enclosure mechanism for sealing the vessel body, wherein the vessel body is configured for use in a centrifugation device;

the vessel body containing:
  a pretreatment mixture comprising a blood cell lysis reagent, and
  a hydrophobic cushioning liquid having a density greater than that of the whole blood sample and the blood cell lysis reagent, wherein the cushioning liquid forms a liquid interface below a supernatant upon centrifugation of said vessel body such that microbial cells within a whole blood sample are removed from suspension and collected adjacent to the liquid interface;
wherein the distal portion of said vessel body is conical in shape.

In another aspect, there is provided a method of extracting microbial cells from a liquid sample, the method comprising:

adding the liquid sample to a pretreatment vessel, the pretreatment vessel comprising a pretreatment mixture, the pretreatment mixture comprising a hydrophobic cushioning liquid having a density greater than that of the liquid sample;

agitating the contents of the pretreatment vessel;

centrifuging the pretreatment vessel such that the cushioning liquid forms a liquid interface below a supernatant, wherein microbial cells from the liquid sample are removed from suspension and collected adjacent to the liquid interface;

withdrawing a substantial quantity of the supernatant without removing the collected microbial cells;

agitating the contents of the pretreatment vessel and allowing the cushioning liquid to re-establish the liquid interface below a suspension containing the microbial cells; and extracting a least a portion of the suspension without extracting a substantial portion of the cushioning liquid, thereby obtaining an extracted suspension comprising microbial cells.

In another aspect, there is provided a method of extracting microbial cells from a whole blood sample, the method comprising:

adding a whole blood sample to a pretreatment vessel, the pretreatment vessel comprising a pretreatment mixture, the pretreatment mixture comprising a blood cell lysis reagent;

agitating the contents of the pretreatment vessel;

centrifuging the pretreatment vessel such that the microbial cells from the whole blood sample are removed from suspension and collected adjacent to the distal surface of the pretreatment vessel;

withdrawing a substantial quantity of the supernatant without removing the collected microbial cells;

performing at least one series of wash steps, each series of wash steps comprising:
  adding a volume of wash buffer to the pretreatment vessel;
  agitating the contents of the pretreatment vessel;
  centrifuging the pretreatment vessel such that the microbial cells are removed from suspension and collected adjacent to the distal surface of the pretreatment vessel; and
  withdrawing a substantial quantity of the supernatant without extracting the collected microbial cells; and
  agitating the contents of the pretreatment vessel to obtain a suspension containing the microbial cells; and extracting a least a portion of the suspension, thereby obtaining an extracted suspension comprising microbial cells.

In another aspect, there is provided a method of, the method comprising:

pretreating a sample containing microbial cells to obtain a suspension containing the microbial cells;

lysing the microbial cells within the suspension to obtain a lysate; and performing a multiplexed set of molecular assays on the lysate, the multiplexed set of molecular assays comprising:
  at least one primary rRNA-based molecular assay for identifying the kingdom of microbial cells present in the sample;
  at least one secondary rRNA-based molecular assay for identifying a Gram status of microbial cells present in the sample; and
  at least one tertiary rRNA-based molecular assay at the genus, species level for each of fungi, Gram-positive bacteria, and Gram negative bacteria;
wherein the at least one tertiary rRNA-based molecular assay for each of each of fungi, Gram-positive bacteria, and Gram negative bacteria are suitable for the de-escalation of antimicrobial therapy based on their outcome.

In another aspect, there is provided an apparatus for extracting microbial cells from a sample, the apparatus comprising:

a motor;

a rotor driven by the motor, the rotor being configured to support a pretreatment vessel such that a centrifugal force is applied to the contents of the pretreatment vessel during rotation of said rotor, wherein the motor is configured to rotate the rotor at a speed sufficient for removing the microbial cells from suspension and collecting the microbial cells near a distal surface of the pretreatment vessel;

a rotating union comprising a rotating portion and a non-rotating portion, wherein said rotating portion rotates in unison with said rotor;

an aspirant tube extending from said rotating portion of said rotating union into the pretreatment vessel through a cap provided on the pretreatment vessel, said aspirant tube having a distal aspirant orifice positioned near the distal surface of the pretreatment vessel;

a dispensing tube extending from said rotating portion of said rotating union into the pretreatment vessel through said cap, said dispensing tube having a distal dispensing orifice positioned near the distal surface of the pretreatment vessel;

a stationary entrance tube connected to said non-rotating portion of said rotating union, such that said stationary entrance tube is in fluid communication with said dispensing tube during rotation of said rotor;

a stationary exit tube connected to said non-rotating portion of said rotating union, such that said stationary exit tube is in fluid communication with said aspirant tube during rotation of said rotor; and a pump mechanism in fluid communication with said stationary entrance tube and said stationary exit tube for dispensing and aspirating fluids.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 1(a) to (m) depict an example sample pretreatment vessel and its contents at different stages during sample pretreatment.

FIGS. 2(a) to (c) illustrate an alternative example embodiment for performing pretreatment on a sample other than whole blood.

FIGS. 3(a) and (b) illustrate another alternative example embodiment for performing pretreatment on a sample other than whole blood.

FIGS. 5(a) and 5(b) schematically depict example embodiment for automating the sample pretreatment method, while

FIG. 9(a) illustrates an example rapid identification panel for de-escalation of antibiotic therapy.

FIG. 9(b) illustrates example organism identification based on the results from the rapid identification panel shown in FIG. 9(a), with a corresponding example antibiotic selection.

FIGS. 10(a) to (c) illustrate three example rapid identification panels for de-escalation of antibiotic therapy from broad-spectrum antibiotics to narrower spectrum antibiotics.

FIG. 11(b) shows the assay signals of cell lysates in the supernatant of fourth wash cycle and FIG. 11(c), the fifth wash cycles, illustrating the dependence of the assay signal on the number of wash steps and cell lysis method.

FIG. 17 is a table showing the fluorescence intensity values obtained for the detection of *Candida albicans* in blood samples detected by molecular beacon hybridization to RT-PCR amplified 18S rRNA.

FIG. 19 is a table showing the fluorescence intensity values obtained for the detection of *Streptococcus pneumoniae* in blood samples detected by molecular beacon hybridization to RT-PCR amplified 16S rRNA.

FIG. 21 is a table showing fluorescence intensity values for the detection of *Escherichia coli* in blood samples detected by molecular beacon hybridization to RT-PCR amplified 16S rRNA.

FIG. 22 is a table describing the microbial cells that were tested to show the repeatability of the detection method.

FIG. 23 is a table describing the primers employed for RT-PCR assays described in FIGS. 25-27 which show the repeatability of the detection method.

DETAILED DESCRIPTION

Figure 4A:
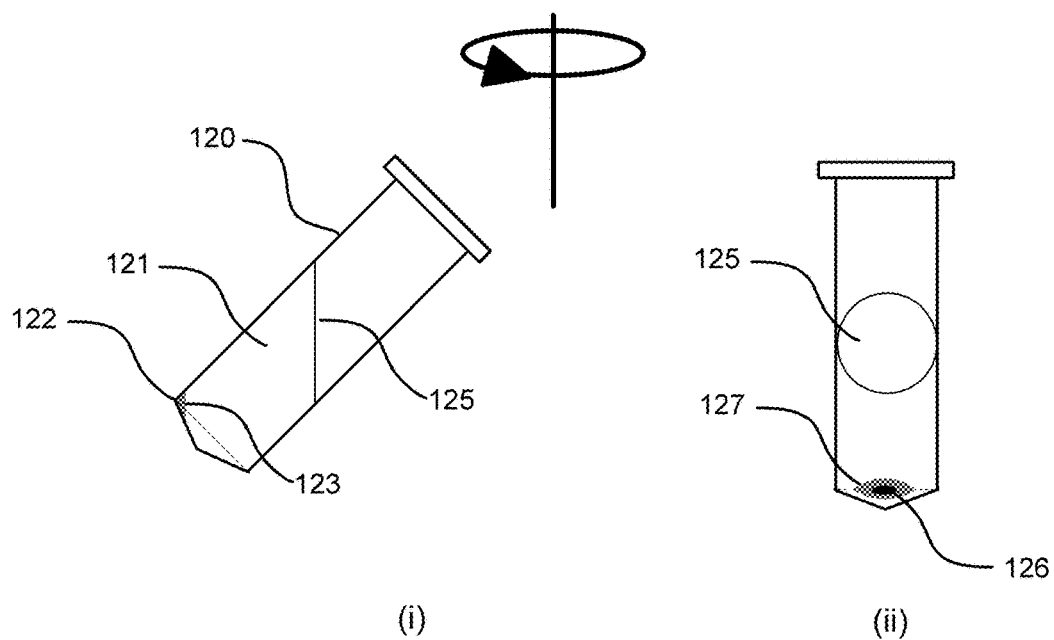
FIGS. 4(a) to (c) schematically illustrate three example pretreatment vessels and their respective sedimentation zone in an angled centrifuge.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure. In some embodiments, the phrases "about" and "approximately" refer to ranges of plus or minus 25% of the stated value.

In embodiments disclosed below, methods and devices are provided for sensitive detection and identification of microbial cells in a sample. In some embodiments, the pretreatment of the sample is performed via the initial selective lysis of non-microbial cells (such as blood cells) and subsequent centrifugation and optional wash cycles to remove the resulting debris and concentrate the microbial cells, where the microbial cells are subsequently resuspended. The resulting microbial cell suspension is herein termed the "pretreated cell suspension".

Sample Pretreatment Using a Cushioning Liquid

A method was disclosed by Dorn, for example, in U.S. Pat. Nos. 5,070,014, 4,131,512, 4,212,948, 4,693,972, and 5,108,927, for lysing a blood sample and concentrating microbial pathogens for the purpose of culturing and detection. Dorn teaches the use of a sample collection tube that includes a blood lysis agent, containing saponin and sodium polyanetholesulfonate (SPS), and a cushioning liquid such as a high density liquid fluorinated hydrocarbon. A volume of whole blood is added to the sample collection tube, and the saponin lyses blood cells in the sample. The cushioning liquid forms a distinct liquid layer at the bottom of the sample collection tube, and is provided to collect microbial cells at its liquid interface when the tube is centrifuged and retain the viability of the microbial cells which may otherwise be damaged by impact or compaction forces in the resulting pellet. After removal of the majority of the supernatant, Dorn teaches the removal of all of the remaining liquid in the tube, including any residual supernatant and all of the cushioning liquid.

The method of Dorn enjoyed commercial success prior to the advent of automated blood culture systems, as it was suitable for preparing microbial cells in a form that could be readily cultured. Unfortunately, the present inventors have found that the Dorn sample preparation method is not suitable for many other applications, such as molecular assays, as the concentrated cell suspension obtained contains contaminants and inhibitory substances.

Many other known methods which employ blood lysing agents for the preparation of cell suspensions followed by a microbial lysing step, or which use non-selective lysing methods to lyse both blood cells and microbial cells to prepare the sample, are also incompatible with downstream molecular assays as they do not provide adequate removal of contaminants or inhibitory substances and therefore require the use of nucleic acid extraction and purification methods prior to the molecular assay (Nierhaus, A., et al. "Comparison of three different commercial PCR assays for the detection of pathogens in critically ill sepsis patients." *Medizinische Klinik-Intensivmedizin and Notfallmedizin* (2013): 1-8.).

Accordingly, in some embodiments of the present disclosure, devices and methods are provided for the separation and concentration of microbial cells from a liquid sample, in which a cushioning liquid is optionally employed to collect microbial cells during a centrifugation step, but without substantially transferring the cushioning liquid when extracting the pretreated sample. Furthermore, in some embodiments, one or more wash procedures are performed prior to extraction of the pretreated sample in order to reduce the concentration of lysed blood cell debris and other undesirable components and substances that may be present in the pretreated sample. The reduction in concentration of these substances in the pretreated sample may be beneficial in avoiding enzyme inhibition for molecular assays, reducing the presence of non-target macromolecules and preventing degradation of target macromolecules.

The retained microbial cells present in the pretreated sample may be lysed and optionally subjected to treatment processes (example treatment processes are described further below) for rendering the intracellular nucleic acid macromolecules (such as ribosomal RNA (rRNA) and DNA) available for subsequent molecular analysis. In some embodiments, subsequent amplification and detection steps may be employed for the identification of the microbial cells. For example, the amplification and detection steps may be performed directly on the pretreated and lysed sample without employing common nucleic acid extraction and purification techniques. In particular, lysing techniques which do not employ reagents that would otherwise interfere with amplification and detection (for example, lysing techniques such as electrical, thermal and mechanical lysis) may be employed in this context.

In some embodiments, in which the sample is a blood sample containing blood cells (such as red blood cells and white blood cells) in addition to potentially containing microbial cells, the sample may be pretreated in order to lyse the blood cells.

In embodiments of the present disclosure that involve performing molecular assays after performing sample pretreatment, the composition of the cell lysis reagent may be selected to be different from that disclosed by Dorn, because unlike the methods disclosed by Dorn that required cell viability for subsequent analysis, cell viability may not be required for molecular methods, and the threshold for acceptable cell injury in the context of such molecular methods may be higher than that of the Dorn protocol.

In some embodiments that involve the pretreatment of blood samples, the formulation of the blood lysis reagent is modified relative to that disclosed by Dorn in order to improve the efficiency of washing cycles without substantial loss of target nucleic acids. For example, an improved blood cell lysis reagent may be provided by selecting appropriate concentrations of saponin and SPS. Moreover, as described below, other blood lysis reagents, such as, for example, Triton X-100, which in the context of culture methods may inhibit cell growth, can be used in some of the methods disclosed herein. Examples of such blood lysis reagents are described in detail below.

In some embodiments, aspects of the sample pretreatment method are controlled or prescribed such that: a high recovery of microbial cells is obtained, such that a substantial percentage (e.g. greater than 10%, 25%, 50%, 75%, or 95%) of the microbial cells present in the original sample are transferred to the pretreated cell suspension; appreciable injury is not inflicted on the microbial cells, such that the recovered microbial cells preserve a substantial percentage (e.g. greater than 10%, 25%, 50%, 75%, or 95%) of the target rRNA or mRNA or 100% of the target DNA; and the pretreated cell suspension liquid should be substantially free of contaminants and substances that are detrimental to or inhibit subsequent nucleic acid assays (e.g. in some applications, it has been found that such contaminants and/or interferents should have a concentration below approximately 0.1%). As described further below, various aspects of the methods described herein are suitable to be performed as automated methods and devices.

FIGS. 1(a)-(m) illustrate an example implementation of a pretreatment device and method according to one embodiment of the present disclosure, which may be employed for the pretreatment of whole blood samples, in which a cushioning liquid is employed. Referring to FIG. 1(a), pretreatment vessel 20 is provided containing a volume of blood cell lysis reagent 22 and volume of cushioning liquid 21.

Pretreatment vessel 20 is a vessel suitable for centrifugation, such as a microcentrifuge tube. In some embodiments, the centrifuge tube has a conical bottom shape and a smooth inner surface, which minimises adsorption or trapping of microbial cells during centrifugation. In some embodiments, pretreatment vessel 20 includes an injectable closure member, such as pierceable stopper 25 (such as a rubber stopper), or another suitable sealing mechanism that may be evacuated such that an appropriate volume of sample is drawn when the pierceable stopper is pierced by the needle of syringe 27.

In some embodiments, pretreatment vessel 20 is employed to obtain a selected volume of blood from a previously filled blood tube, such as another blood collection tube. In some embodiments, pretreatment vessel 20 may be employed as a sample collection device. For example, pretreatment vessel 20 may include a pierceable stopper that is configured for use with a Vacutainer®-type needle and holder device.

Cushioning liquid 21 is a high density and water immiscible liquid that serves to form liquid surface 32 onto which the microorganisms settle during centrifugation. As shown in FIG. 1(a), cushioning liquid 21 has a density such that it settles at the bottom of pretreatment vessel 20 under the influence of gravity. It will be understood that the term "high density", as used herein with regard to cushioning liquid 21, means a density that is sufficiently high such that the target microbial cells will not substantially penetrate the cushioning liquid under the prevailing centrifugal force. The density of the cushioning liquid 21 is therefore chosen be greater than both the microbial cells and the other liquids. The cushioning liquid is also immiscible in the other liquids including, but not limited to, whole blood, blood cell lysis reagent 22, and a wash liquid (as described below) such that it remains a distinct liquid phase throughout the pretreatment process.

Blood cell lysis reagent 22 is an aqueous liquid that includes one or more substances selected to lyse blood cells. In some embodiments, the composition of the blood cell lysis reagent is selected such that blood cells are lysed without substantially affecting the integrity of microbial cells. Examples of suitable compositions of blood cell lysis reagent 22 are provided below.

FIG. 1(b) illustrates the addition of a volume of blood sample 26 to pretreatment vessel 20, where mixing of blood lysis reagent 22 with the blood sample 26 forms mixture 30 shown in FIG. 1(c). After providing a sample to pretreatment vessel (e.g. through pierceable rubber stopper 25), pretreatment vessel 20 may be agitated to produce further mixing of the sample with blood cell lysis reagent 22, as shown in FIG. 1(c). For example, pretreatment vessel 20 may be manually inverted one or more times to provide gentle mixing. In an alternative example, pretreatment vessel 20 may be vortexed at a low speed. A non-limiting example of a suitable low vortexing speed is a speed near approximately 300 rpm for a 4.9 mm orbit vortex mixer. An alternative mixing method can be employed in which the liquid is aspirated and dispensed for a number of cycles.

As stated above, the presence of blood cell lysis reagent 22 in mixture 30 causes the selective lysis of blood cells. In one example implementation, blood cell lysis reagent 22 may be an aqueous liquid including at least the following components: saponin, sodium polyanetholesulfonate (a sodium salt of polyanetholesulfonic acid, known as SPS), and an antifoaming agent, such as poly (propylene glycol) (PPG, e.g. with a molecular weight of approximately 2000). In some embodiments, the saponin is purified saponin. Example methods for purifying saponin are disclosed in U.S. Pat. No. 3,883,425, titled "Detoxification of Saponins", which is incorporated herein in its entirety. It has been found that without saponin purification blood cell lysis is less efficient and a gel-like substance is formed upon centrifugation.

In one example implementation, a composition of the blood cell lysis reagent, per approximately 1 mL of whole blood, may be provided as follows: an aqueous solution having a volume of approximately 500 µL with a concentration of approximately 75 mg/mL saponin (84510, Sigma), approximately 15 mg/mL sodium polyanetholesulfonate (SPS) (P2008, Sigma) and approximately 1% by volume of poly(propylene glycol) (PPG) MW 2000 (202339, Sigma). Upon mixing the blood lysis reagent with the whole blood sample the final concentrations of Saponin, SPS and PPG are approximately 25 mg/ml, 5 mg/ml, and 0.3% respectively.

In one example implementation, the concentrations of saponin and SPS, upon mixing whole blood and the blood lysis reagent may be in the range of approximately 1.5 to 80 mg/mL and 0.5 to 20 mg/mL, respectively. In another example implementation, the concentrations of the saponin and SPS may be in the range of from approximately 10 to 30 mg/mL and 2.5 to 10 mg/mL, respectively.

SPS is an anti-coagulant and anti-phagocytosis agent and is known to inhibit antimicrobial agents (Sullivan, N. M., Sutter, V. L., & Finegold, S. M. (1975). Practical aerobic membrane filtration blood culture technique: development of procedure. *Journal of clinical microbiology*, 1(1), 30-36.). The mechanism by which SPS assists in blood cell lysis is not well understood. Without intended to be limited by theory, it is believed that SPS may offer some level of protection to the microorganisms during blood cell lysis, reduce the incidence of entrapment of bacteria in cell debris, and/or reduce the amount of coagulated components which may otherwise be present in the sediment.

It is noted that SPS a known PCR inhibitor. At higher concentrations of SPS, more washing cycles may be employed to remove excess SPS, for applications in which a low concentration of SPS in the final extracted sample is desirable. It is also noted that U.S. Pat. No. 8,481,265 describes the use of saponin with concentrations (the final concentration) in the range of 40-100 mg/ml as a lysis reagent, without the use of SPS or a cushioning fluid. However, such an approach results in the pelleting of the microbial cells during centrifugation, and difficulty in resuspending the pelleted microbial cells. In fact, in the examples provided in U.S. Pat. No. 8,481,265, mechanical means were required for harvesting of the microorganism from the tube wall, which is less amenable to automation.

The addition of PPG, an antifoaming agent, assists in maintaining a suitable viscosity of the mixture. It has been found that without the inclusion of PPG, the mixture may be thick and/or sticky.

In another example implementation, a composition of the blood cell lysis reagent, for lysing approximately 1 mL of whole blood, may be provided as follows: an aqueous solution having a volume of approximately 500 µL, with a concentration of approximately 1.5% by volume Triton X-100 (X-100, Sigma), approximately 18 mg/mL sodium polyanetholesulfonate (SPS) (P2008, Sigma) and approximately 1% by volume poly(propylene glycol) (PPG) MW 2000 (202339, Sigma) in a buffer pH ranging from 5 to 11. Upon mixing the blood lysis reagent with the whole blood sample the final concentrations of Triton X-100, SPS and PPG are approximately 0.5%, 6 mg/ml, and 0.3% respectively. In one example implementation, the concentrations of Triton X-100 and SPS upon mixing the lysing reagent and whole blood sample may be in the range of approximately 0.5 to 1.5% and 5 to 10 mg/mL, respectively. In another example implementation, a composition of the blood cell lysis reagent, for lysing approximately 1 mL of whole blood, may be provided as follows: an aqueous solution having a volume of approximately 1 mL, and with a concentration of approximately 1% Triton X-100 (X-100, Sigma) in a buffer pH ranging from 9 to 11. In one example implementation, upon mixing the lysing reagent and whole blood sample the concentrations of Triton X-100 may be in the range of approximately 0.05 to 2.5%.

After forming mixture 30 and agitating pretreatment vessel 20, pretreatment vessel 20 is centrifuged, as illustrated in FIG. 1(*d*). Pretreatment vessel 20 is centrifuged at a suitable rate and for a suitable time to cause microbial cells in mixture 30 to pass out of the suspension and collect at interface 32 between cushioning liquid 21 and supernatant 33 as shown in FIG. 1(*d*).

It will be understood that the centrifugation time and speed required to effect sedimentation of the microbial cells depends on the centrifuge radius, sample viscosity and density, and sedimentation path length, and may be determined readily by those skilled in the art. For example, in one example embodiment, in which a blood volume of approximately 1 ml is injected into a 2 ml pretreatment vessel (with a suitable quantity of blood lysis reagents 22 and cushioning liquid 21 disclosed above) and placed in a fixed angle centrifuge, a centrifugal force of approximately 10000 g and a centrifugation time of approximately 1 minute is sufficient to sediment microbial cells of interest. It will be understood that other combinations of time, speed, and sample volume may be selected to achieve complete collection of the microbial cells at the cushioning surface 32.

As noted above, cushioning liquid 21 has a density greater than that of mixture 30 and is immiscible with mixture 30 such that interface 32 is formed. This ensures that under centrifugal forces cushioning liquid 21 rapidly moves to the sedimentation region 34 and displaces supernatant 33, thereby forming a distinct fluid phase in the sedimentation region 34 of pretreatment vessel 20. Cushioning liquid 21 prevents the loss of microbial cells during the pretreatment process. Such a loss could otherwise occur due to adsorption and trapping of microbial cells on the surface of pretreatment vessel 20 within or near sedimentation region 34, but is substantially prevented in the present embodiment due to the presence of the liquid interface 32, where the microbial cells collect. Since the density of the cushioning liquid is greater than that of the cells the cushioning liquid prevents the cells from coming into close contact with the vessel walls or entering cavities in the wall which may otherwise trap said cells.

Fluorinated hydrocarbons, having molecular weight ranging from about 300 to 850, are suitable as cushioning liquids. Examples are FC-40, FC-43, FC-70, and FC-77. For the examples provided in this disclosure, Fluorinert™ FC-40 (F9755, Sigma) was used. The cushioning liquid volume should be sufficiently large to provide an adequately large sedimentation surface so that all target precipitate is collected on its surface. The cushioning liquid volume suitable for effective microbial cell recovery is dependent on a number of factors, including the pretreatment vessel geometry, pretreatment vessel surface condition, centrifuge angle, centrifugal force and target cell sedimentation coefficient which are collectively termed centrifugal conditions.

One guiding principle for determining the volume of the cushioning liquid volume is that the surface of the pretreatment vessel wetted by the cushioning liquid should at least envelop the region of the pretreatment vessel surface where the microbial cells would sediment in the absence of the cushioning liquid. During centrifugation suspended cells move radially and when they encounter the pretreatment vessel wall they continue to move along the wall toward the extreme radial position until the component of the centrifugal force in the direction of the preferred movement is insufficient to overcome buoyancy and frictional forces which oppose cell motion. In the absence of the cushioning liquid the cells come to rest in a sedimentation region whose geometry reflects the centrifugal conditions. By providing cushioning liquid which envelops this region the cells will come into contact with the cushioning liquid either directly on its surface or on its periphery. By way of illustration FIGS. 4(a), (b) and (c) show three different pretreatment vessel bottom angle geometries respectively in a 45 degree angle centrifuge. In each case, the pretreatment vessel is shown in radial section view (along the rotor radius) as (i) and in a view from the rotor axis in a direction perpendicular to the pretreatment vessel axis as (ii). In FIG. 4(a) the pretreatment vessel 120 has a bottom cone angle which is approximately 25 degrees and contains a fluid 121 in which the target microbial cells are initially suspended. The surface of this fluid is shown in FIG. 4(a) (i) and (ii) as 125. In the absence of a cushioning liquid, after centrifugation for a sufficient duration at an appropriate speed, the cells will come to rest at or near the radially outermost portion 122 of the pretreatment vessel which in this case is at the intersection between the cylindrical and conical portions of the pretreatment vessel. The sedimentation region 126 may extend a distance circumferentially on either side of the radially outermost point of the pretreatment vessel as shown in FIG. 4(a) (ii) due to the decreasing net force in the direction of movement of sedimenting cells which are moving along the wall toward the extreme radial position.

When a cushioning liquid is initially present in the pretreatment vessel and centrifugation is performed in its presence, its surface 123 will approximately form a vertical plane and the cushioning liquid will wet the pretreatment vessel surface within the region 127 shown approximately in FIG. 4(a) (ii). In order to ensure that sedimenting cells come into contact with the cushioning liquid before coming to rest on the pretreatment vessel surface, the cushioning liquid should fully envelop the region 126 where sedimentation would have occurred in the absence of the cushioning liquid.

Figure 4B:
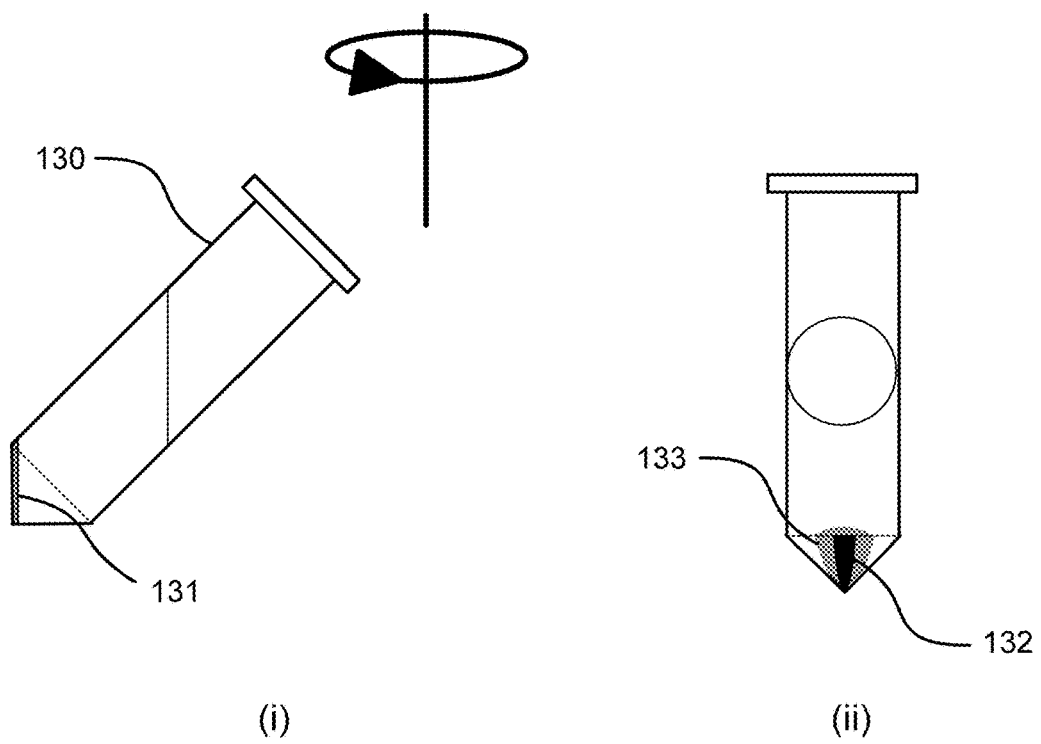

Likewise, in a pretreatment vessel with a bottom cone angle of 45 degrees which matches the centrifuge angle in this example, shown in FIG. 4(b) as 130, the cushioning liquid will form a surface 131 as shown in FIG. 4(b) (i). The sedimentation zone 132 in the absence of the cushioning liquid will generally be distributed along the cone as shown in FIG. 4(b) (ii). The surface region 133 of the pretreatment vessel wetted by the cushioning liquid should at least envelop the sedimentation zone 132.

Figure 4C:
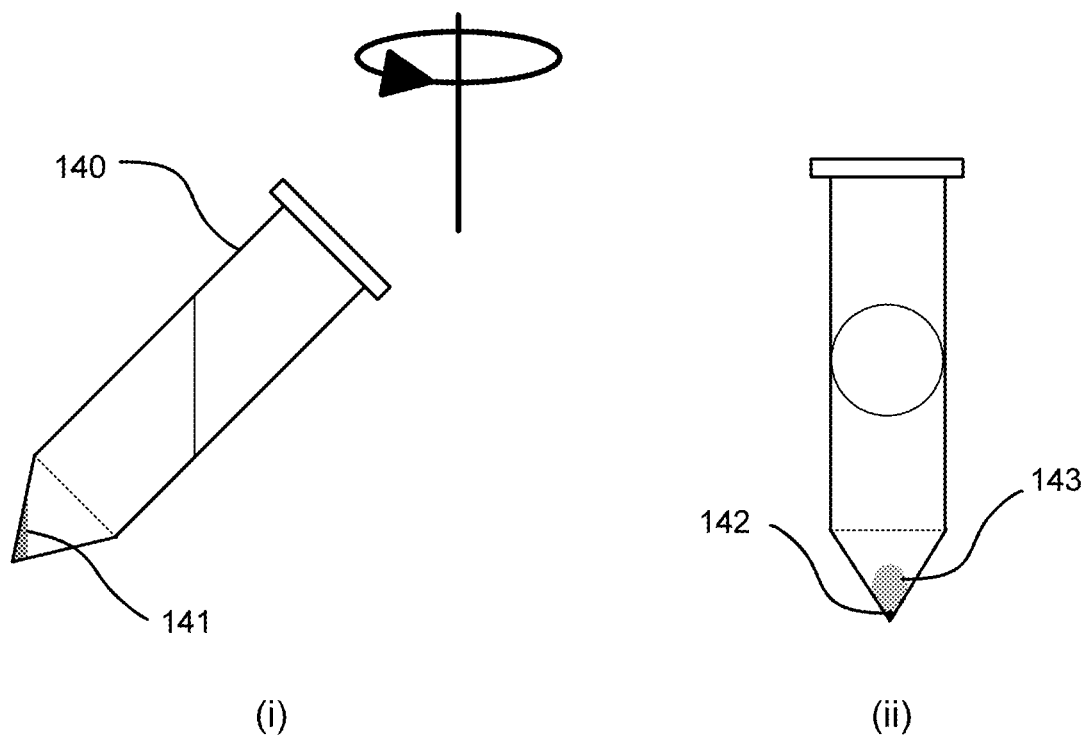

When the pretreatment vessel bottom cone angle is greater than the centrifuge angle as shown in FIG. 4(c) the sedimentation zone is at the apex of the cone and the cushioning liquid 143 should envelop the sedimentation zone 142.

It is evident from these examples that the minimum volume of cushioning liquid is dependent on the prevailing geometrical and sedimentation conditions. Swinging bucket or horizontally oriented centrifuges can likewise be considered and will generally have a sedimentation region at the apex of the pretreatment vessel, which should be enveloped by the cushioning liquid.

Other sedimentation vessels and centrifugal conditions can be similarly considered to determine the minimum cushioning liquid volume.

It is noted that variability in the centrifugal conditions may necessitate a cushioning liquid volume somewhat larger than the minimum determined as described above to ensure maximum recovery.

The sedimentation region on the surface of the pretreatment vessel which prevails in the absence of the cushioning liquid, and which is wetted by the cushioning liquid in accordance with the selected embodiments disclosed above, can be determined empirically. An example of an empirical method is the observation of the pellet of the sedimented cells on the surface of the selected pretreatment vessel under centrifugal conditions which are the same as those expected in the pretreatment process in the absence of the cushioning fluid. This may be assisted by fluorescent or other dyes applied to the cells to enhance the optical detection of the sedimented cells. The volume of cushioning fluid suitable for enveloping this measured region could be determined by observing the extent of the wetted region of the cushioning fluid on the surface of the pretreatment vessel under the same centrifugal conditions and ensuring that this wetted region extends at least beyond the previously observed sedimentation region (for example, by performing several experiments of cushioning liquid, and selecting the volume that sufficiently wets the measured region). Alternatively, the recovery of cells in the final suspension obtained by the methods described herein can be measured by various means such as, for example, culturing and colony enumeration, and a suitable volume of cushioning liquid determined empirically by selecting a volume that provides a suitable (e.g. maximum) cell recovery.

The volume of cushioning liquid can also or alternatively be estimated by considering the interaction between the sedimenting particle and the inner surface of the pretreatment vessel during, centrifugation. During centrifugation, the particle whose density is greater than that of the suspension fluid will move radially outward under the influence of the centrifugal force vector $\vec{F}_c$ of magnitude $|\vec{F}_c|=V_p(\rho_p-\rho_m)\omega^2 R$ until it reaches the surface of the pretreatment vessel. Here $V_p$, $\rho_p$, $\rho_m$, r represent the volume of the particle, the density of the particle, the density of the particle suspension medium, the angular velocity and the radial distance from the particle to the axis of rotation respectively.

Figure 4D:
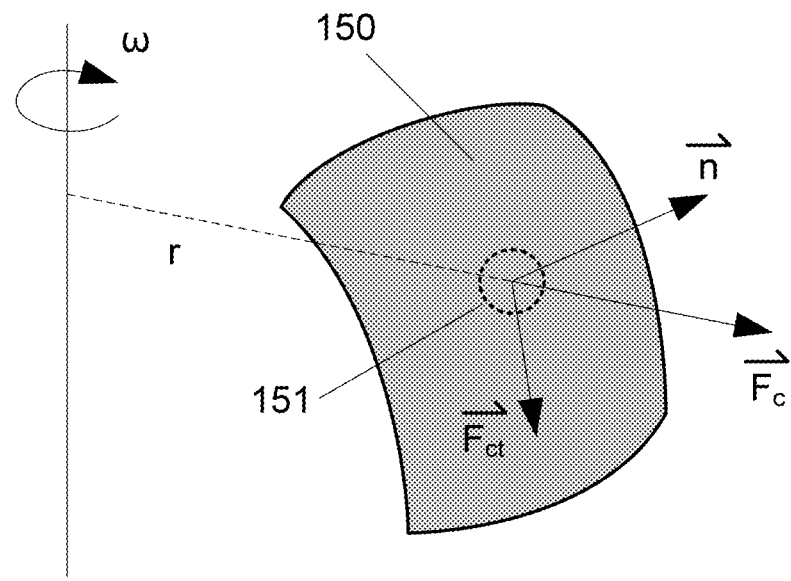
FIG. 4(d) schematically illustrates centrifugal force acting on a particle which has reached pretreatment vessel surface during centrifugation.

Upon the particle 151 reaching this surface 150 where the unit outward normal vector to the surface is n as depicted in FIG. 4(d), the particle path will be altered due to the presence of the pretreatment vessel wall. The particle trajectory will then be along the pretreatment vessel inner surface in the direction of the vector component of the centrifugal force ($\vec{F}_{ct}$) in the tangent plane at the particle position given by the relation $\vec{F}_{ct}=\vec{F}_c-(\vec{F}_c \cdot \vec{n})\vec{n}$.

Directly opposing this force will be fluid resistance whose magnitude is commonly represented in the state of the art by the Stokes equation $F_s=6\pi\eta rv$, where $\eta$ and $v$ are the fluid viscosity of the suspension medium and the velocity of the particle respectively, and a wall frictional force $F_w$ which, if of sufficient magnitude relative to the other prevailing forces, should be included and determined for the particular conditions of the pretreatment vessel surface, particle and suspension fluid under consideration.

Thus the particle will reach a limiting or terminal velocity when force equilibrium is achieved as represented by $|\vec{F}_{ct}|=F_S+F_W$. A condition defining formation of a stable sediment may be defined by $v=0$ or $v$ a sufficiently small value and thereby the above equations can be used to define a locus of points on the pretreatment vessel surface at which the particles will effectively come to rest. This locus of points defines a sedimentation region on the pretreatment vessel inner surface which should be wetted by the cushioning fluid in accordance with the principles discussed above. As a number of parameters in the above are subject to some amount of variation or uncertainty it is generally recommended to confirm the results empirically.

It is also to be understood that the cushioning liquid surface should not be so large as to cause loss of sedimented cells during aspiration of the supernatant during the centrifugal separation step.

In this respect, a consideration is the location of the sedimentation zone during centrifugation. Generally, some of the collected cells will settle on the periphery of the cushioning liquid (referred to below as a "periphery collection region") and some of such cells may remain on the pretreatment vessel wall even if the pretreatment vessel is reoriented for aspiration. Since these cells are easily resuspended to the presence of the cushioning liquid, and care should be taken not to disturb this region with convective disturbances in order to prevent loss of cells. Such convective disturbance may occur due to aspiration of the supernatant.

In some embodiments the pretreatment vessel geometry and/or the volume of cushioning fluid should be selected so that this periphery collection region remains distant from the aspiration device. Moreover, in some embodiments, the pretreatment vessel geometry and/or the volume of cushioning fluid may be selected such that the periphery collection region remains submerged in the residual liquid during aspiration of supernatant.

For example, a pretreatment vessel (e.g. centrifuge tube) with a conical or round (e.g. hemispherical) bottom (or a combination thereof, such as conical tapering side walls terminating in a hemispherical or otherwise round bottom), may be employed to allow the sediment to remain in the bottom of the pretreatment vessel at a location that is distant from the aspiration device, and hence undisturbed while removing the supernatant. This becomes more important as the desired residual fluid volume is decreased.

A suitable maximum volume of cushioning liquid is thereby related to a number of factors, such as the desired residual fluid volume, the pretreatment vessel geometry, centrifuge angle and aspiration method. The distance between the aspiration tip and the cushioning fluid during the aspiration of the supernatant should be at least 1 mm and preferably 3 mm to 5 mm or greater.

An example volume of cushioning liquid 21 is approximately 10 μL for a 2 mL pretreatment vessel in an angle centrifuge operating at 6000 g. In another example embodiment, the volume of cushioning liquid may range between approximately 5 μl and 15 μl. In another example embodiment, the volume of cushioning liquid may range between approximately 2.5 μl and 100 μl.

After centrifugation, pretreatment vessel 20 may be re-oriented in a position suitable for subsequent aspiration and dispensing operations, such as, for example, a vertical orientation as shown in FIG. 1(e), such that cushioning liquid 21 moves to the bottom of pretreatment vessel 20 and remains there due to gravity. This step may be performed sufficiently slowly such that convective disturbances in the liquid are minimised such that most or all of the microbial cells are prevented from being resuspended. The sedimented microbial cells may be deposited on the surface of the vessel proximal to the location of the sedimentation region or some cells may move with the cushioning liquid as it relocates under gravity.

The prevention of resuspension of cells enables the removal of most of the supernatant, as shown in FIG. 1(f), such that only a small volume of residual supernatant is left behind containing the retained microbial cells. For example, a syringe may be employed to remove a substantial portion of the supernatant. In order to achieve concentration of the retained microbial cells and to remove substances that could interfere with downstream processes, it is beneficial to remove as much of the supernatant as possible while leaving behind a sufficient volume of supernatant such that removal of the microbial cells in the aspirant is substantially avoided. Such an embodiment is effective in reducing the transfer of the blood cell debris and lysis reagents to the subsequent washing stages, and to the final pretreated sample. It is to be understood that in some embodiments, step (e) and step (f) may be performed with different orientations and positions of the pretreatment vessel and aspiration device. For example, in step (e) the pretreatment vessel may remain in the orientation of step (d) but be gently rotated 180 degrees in its holder such that the sedimentation region is now located at the bottom of the angled pretreatment vessel. This will allow aspiration of a greater amount of supernatant while leaving the sedimentation region undisturbed.

In one embodiment, the amount of the supernatant that is removed is between 80% and 95% of the total amount of supernatant. In an example implementation employing the quantities according to those described in the above example, a suitable aspirant volume is approximately 1.35 mL.

As shown in FIG. 1(g)-(k), one or more washing cycles may be optionally performed to purify the supernatant and to reduce the concentration of blood cell debris and blood cell lysis reagent present in the pretreated sample. Referring to FIG. 1(g), a volume of the washing liquid 35 may be added to sample pretreatment vessel 20. After addition of washing liquid 35, the solution is mixed to resuspend debris that may have sedimented or adsorbed to the vessel wall during centrifugation. This may be accomplished by vortexing as shown in FIG. 1(h). Pretreatment vessel 20 is subsequently centrifuged and re-oriented, and a substantial portion of the supernatant is removed, as shown in FIGS. 1(i) to (k), similar to the manner described for FIGS. 1(d) to (f).

In one example implementation, washing liquid 35 may be any low ionic strength aqueous medium such as salt solutions or buffers. The choice of lower ionic strength enables using the microbial cell lysate, following electrical or mechanical cell lysis, for molecular assays without requiring an ion balance step.

As noted below, the microbial cells are suspended in residual washing liquid 37 when the pretreated sample is extracted from pretreatment vessel 20. Accordingly it may be beneficial for the washing liquid 35 to have a composition suitable for downstream processing of the sample. In one example implementation, washing liquid 35 may include one or more reagents or media for preserving the viability of the retained microbial cells. For example, washing liquid 35 may include monovalent salt solution such as potassium chloride or sodium chloride. In another example, the washing liquid is a buffer such as phosphate buffer pH 7.4, Tris buffer pH 8.0. In another example, the washing liquid is a buffer that is compatible with downstream nucleic acid amplification reactions. In embodiments in which electrical lysis is performed subsequent to extraction of the pretreated sample (as described below), the ionic strength of the washing liquid should be selected such that it is compatible with working parameters of the electrical lysis method. For example, for the case of lysing microbial cells via electrical method, the ionic strength of washing liquid 35 may be between approximately 0.1 and 1 mM.

The number of wash cycles employed during sample pretreatment may depend on various factors, such as the desired level of dilution of the residual supernatant 36. For example, in an embodiment in which the sample is a blood sample and the blood lysis reagent includes SPS, it may be useful to dilute the supernatant 36 such that the residual concentration of SPS is less than approximately 0.01 µg/mL.

In one example implementation, the wash procedure is not performed prior to extraction of the processed sample. This embodiment is particularly suited when the intended nucleic acid assay uses inhibitor-resistant PCR reagents, examples of which have been described by A. T. Hall et al ("Evaluation of Inhibitor-Resistant Real-Time PCR Methods for Diagnostics in Clinical and Environmental Samples." *PloS one* 8.9 (2013): e73845.). It is known that high level of haemoglobin left in the suspension quenches the fluorescence signal that typically is employed for monitoring real-time PCR assays. It is understood that the inhibitor-resistant PCR reagents often do not offer the rapid cycling time, therefore wash cycles may be desirable when fast detection time is required.

In another embodiment, one wash cycle may be employed. In other embodiments, two or more wash cycles may be employed. In one example, based on the example parameters disclosed above, four wash cycles were found to provide effective removal of contaminants and inhibitory substances from the sample for downstream processing.

After performing the (optional) washing cycles, pretreatment vessel 20 may be agitated as is shown in FIG. 1(*f*), such that the retained microbial cells are resuspended in the residual supernatant 37. For example, pretreatment vessel 20 may be vortexed for approximately 5 to 20 seconds at a low speed, as described above.

After agitation, cushioning liquid 21 is allowed to settle at the bottom of pretreatment vessel 20, as shown in FIG. 1(*m*), such that pretreatment vessel 20 includes a residual suspension of the retained microbial cells above the cushioning liquid 21. This residual suspension may then be removed to obtain the extracted sample, referred to as the pretreated sample 38.

In one embodiment, a substantial volume of the residual suspension is removed, such that little or none of cushioning liquid 21 is removed. Such an embodiment is beneficial in removing most of the retained microbial cells, while avoiding contamination by cushioning liquid 21. For example, the controlled removal of a selected volume of the residual suspension may be achieved via the insertion of a syringe with calibrated length, which may be inserted through pierceable rubber stopper 25, leaving cushioning liquid 21 behind.

In some embodiments, the portion of the suspension that is removed does not include cushioning liquid. In another embodiment, the portion of the suspension that is removed is substantially free of the cushioning liquid, such that the presence of any cushioning liquid would not have an impact on the performance of a subsequent assay. In another embodiment, all of the residual suspension is removed, which may further include a small fraction of cushioning liquid 21, such as, for example, <1%, <2%, <5%, or <10%. In some embodiments, an acceptable amount of cushioning liquid that can be withdrawn may be determined based on knowledge of an acceptable concentration of the cushioning liquid in a subsequent assay (i.e. such that assay performance is not degraded). In some embodiments, a portion of the cushioning liquid may be removed, where the volume of cushioning liquid that is removed is less than amount that would reduce the performance of a subsequent assay below a preselected level. For example, in the case of a downstream assay involving real-time PCR, experiments may be performed to determine the volume of cushioning liquid that can be removed without reducing the cycle number below a pre-selected threshold for a given standard analyte concentration (e.g. a performance deficit of less than one cycle). In other assay formats, other suitable measures can be employed, such as threshold values associated with the limit of detection and the signal intensity.

In yet another embodiment, in which one or more optional wash cycles are performed, both the residual suspension and a substantial portion of cushioning liquid may be removed, and the cushioning liquid may be externally separated from the residual suspension. For example, in one embodiment, both the residual suspension and a substantial portion of the cushioning liquid may be removed by an aspiration vessel such as a pipette tip. In this case the cushioning liquid may be separated from the residual suspension by allowing it to settle adjacent to a lower orifice of the aspiration vessel (e.g. the pipette tip) and subsequently be dispensed from the orifice of the aspiration vessel or allowed to drip from the orifice of the aspiration vessel without loss of the residual suspension. In another example embodiment, external filtration may be employed to separate the suspension from the cushioning liquid.

Although the preceding example embodiments relate to the processing of whole blood as a sample matrix, it is to be understood that the methods disclosed herein may be adapted to the pretreatment of a wide variety of specimens. Suitable specimens include, but are not limited to, urine, sputum, cerebral spinal fluid, swabbed tissue samples, vaginal samples, and other sample types of biological origin, and non-biological samples that may contain microbial cells. A sample may be provided by processing a solid or partially solid sample in order to produce a liquid sample (e.g. using a process such as homogenization). Examples of other sample types include other liquid samples that may contain microbial cells, such as environmental water samples, liquid food samples, and homogenized food samples. The initial sample may be combined with a reagent, buffer, or other medium prior to introduction into the pretreatment vessel.

FIGS. 2 and 3 illustrate two additional example embodiments for the pretreatment of a biological sample. Both FIG. 2 and FIG. 3 show the initial steps of alternative sample pretreatment embodiments, where the remaining steps are preformed according to the remaining steps (by Figure sub-letter) shown in FIG. 1.

In FIG. 2, an embodiment is shown in which sample pretreatment vessel 20 includes a pretreatment buffer, reagent or liquid 100 that may or may not include a blood cell lysis reagent. For example, liquid 100 may be useful in stabilizing a sample other than a whole blood sample, such as sputum. Sample is added in step (b) and pretreatment vessel 20 is agitated in step (c), with the remainder of the steps performed as described above in relation to FIG. 1(*a*)-(*m*).

Similarly, FIG. 3 shows an example embodiment in which sample pretreatment vessel 20 initially includes cushioning liquid 21, to which sample, or a sample combined with a buffer, reagent or other liquid, is added in step (b). The remainder of the steps are performed as described above in relation to FIG. 1(*a*)-(*m*). Such an embodiment may be useful for the pretreatment of a urine sample, for example. Alternatively, the pretreatment of a urine sample may be performed according to a method similar to that disclosed in FIG. 2, where liquid 100 includes a blood cell lysis reagent for the lysis of blood cells that may be present in the urine sample.

Sample Pre-Treatment without Cushion Liquid

The preceding methods and devices employ the use of a pre-treatment vessel with a cushioning liquid. The cushioning liquid prevents a loss in cell recovery (or assay signal in the case of downstream molecular assays) that would otherwise occur (in the absence of the cushioning liquid) due to the adhesion of microbial cells to the walls of the pretreatment vessel.

Figure 14:
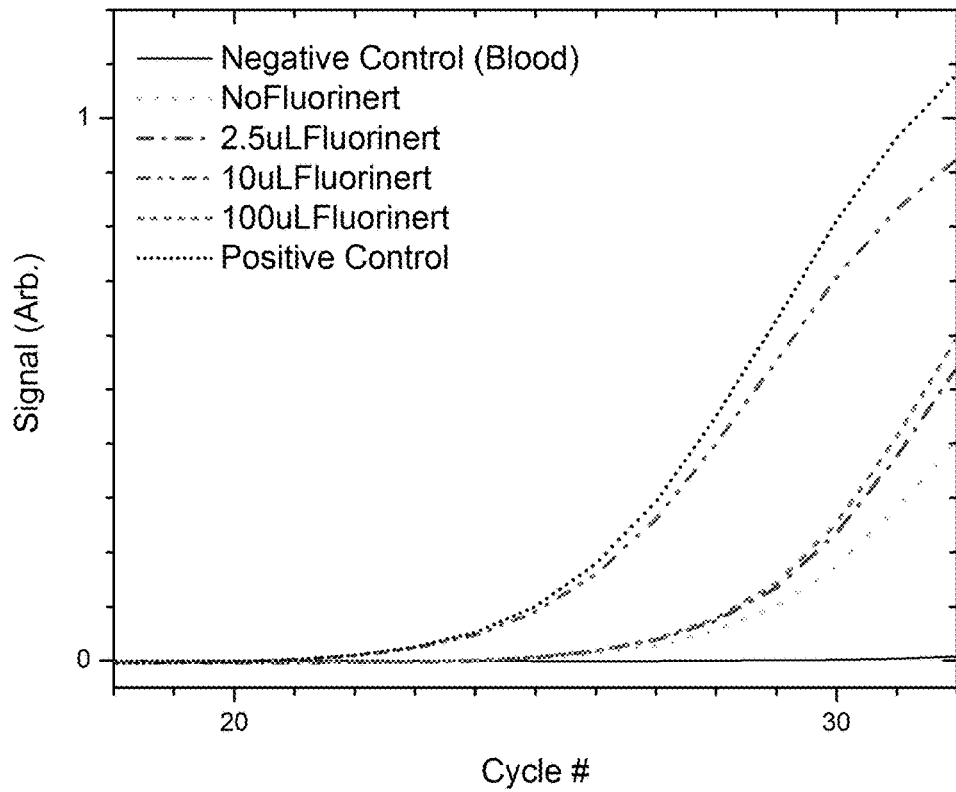
FIGS. 14(a) and (b) show the fluorescence signal versus PCR cycle number measured during real-time RT-PCR assays, illustrating the dependence of the assay signal on the volume of Fluorinert™ in (a) 2 mL and (b) 1.7 mL microcentrifuge tubes
Figure 14:
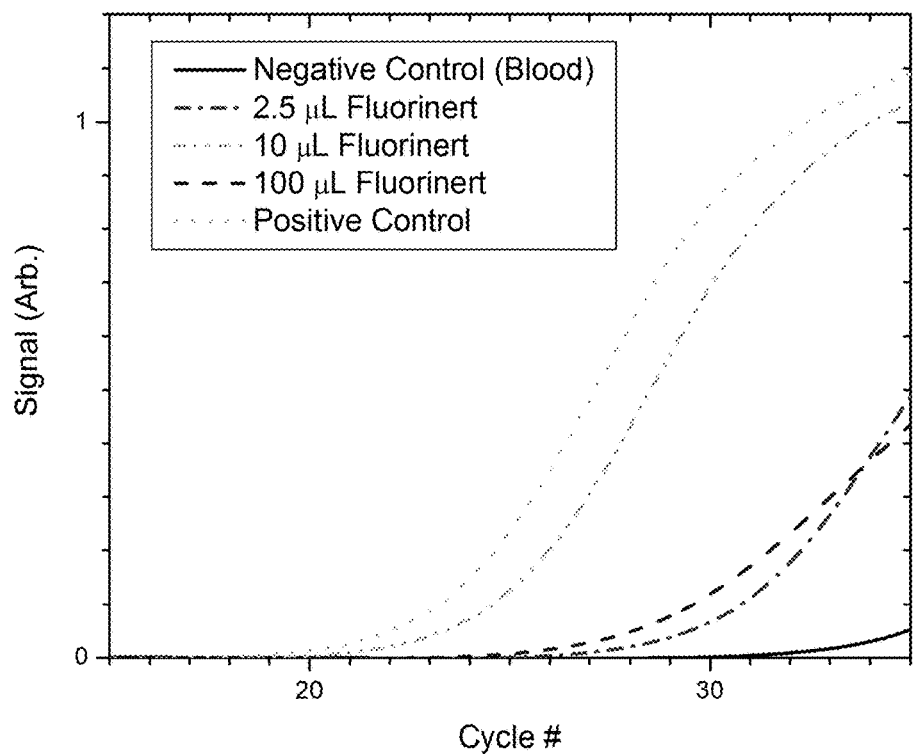

For example, as illustrated in FIG. 14(a), and as described in Example 4.4 below, the inclusion of 10 uL of Fluorinert™ in a siliconized plastic microcentrifuge tube produced a gain of four PCR cycles relative to a pretreatment vessel without a cushioning liquid. This result suggests that the inherently rough or adsorbent surfaces of plastic microcentrifuge tubes, even when treated with siliconization, result in a substantial reduction in recovery when a cushioning liquid is not used. Therefore, in the case of plastic pre-treatment vessels, both the use of a cushioning liquid and the hydrophobic treatment of the vessel surface appear to play significant roles in enabling a high recovery of microbial cells in the extracted suspension.

In other implementations, however, the pretreatment vessel may be formed from a material having a smoother surface than the plastic microcentrifuge tubes described above, and the smoother surface may allow for suitable or acceptable recoveries in the absence of the cushioning liquid. For example, it has been shown by Dorn, in U.S. Pat. No. 4,164,449, that a glass centrifuge tube, having a siliconized surface, may be suitable for pretreatment in the absence of a cushioning liquid, while enabling high recovery values. It is noted, however, that the recovery values reported by Dorn were based on inoculation of a 1000 microbial cells, and that the recovery may be considerably lower for lower inoculation numbers. It is also noted that the Dorn method involved the withdrawal of the major portion of the supernatant after a single centrifugation step, followed by the resuspension of the retained microbial cells in the residual supernatant. Such a method would be incompatible with downstream molecular assays due to the interferents present within the residual supernatant that is used to form the suspension.

Accordingly, in one embodiment, a pretreatment method may be performed according to the embodiments described above, but without employing the cushioning liquid, provided that the pretreatment vessel has a smooth inner surface having a hydrophobic surface treatment (such as a glass centrifuge tube having a siliconized surface). Unlike the method disclosed by Dorn, which was suitable for subsequently growth analysis, the method according to the present embodiment employs one or more intermediate wash steps prior to the withdrawal of the final suspension of microbial cells. The one or more intermediate was steps may be performed according to any of the washing methods described in the present disclosure. The one or more intermediate wash steps result in a higher purity microbial suspension, with a substantially reduced concentration of interferents that would otherwise inhibit or prohibit subsequent (downstream) molecular assays. Such purity was not important to the method of Dorn, in which the suspension was employed for growth purposes, as opposed to for molecular assays that are susceptible to interferents present in the supernatant of a lysed blood sample following an initial centrifugation step. Accordingly, the present embodiment, in which one or more intermediate wash steps are employed in a pretreatment method absent of a cushioning liquid, can be employed to provide a suspension having a high recovery of microbial cells while also having a dramatically lowered concentration of interferents, such that the suspension is suitable for subsequent molecular assays.

In some embodiments, a pretreatment method may be performed without using a cushioning liquid, where a pretreatment vessel having a smooth hydrophobically-treated inner surface is employed (such as a glass centrifuge tube having a siliconized surface), and where the distal portion of the pretreatment vessel has a conical or rounded (e.g. hemispherical) shape that is suitable for extraction of the supernatant (after centrifugation) while leaving a residual volume of less than approximately 100 ul, or less than approximately 50 ul. Such an embodiment results in a concentrated microbial cell suspension (purified by optional wash steps), that is suitable for performing molecular methods. This is in stark contrast to the method of Dorn, in which the final suspension was employed for subsequent growth analysis, without requiring or employing a low-volume concentrated suspension.

Automated Methods of Sample Pre-Treatment

In some embodiments, the sample pretreatment processes disclosed above (with or without a cushioning liquid), or variations thereof, may be automated to reduce the operator involvement and to improve cell collection and washing effectiveness. For example, a centrifuge that is configured with the ability to perform automated wash steps may be employed for this purpose.

Figure 5A:
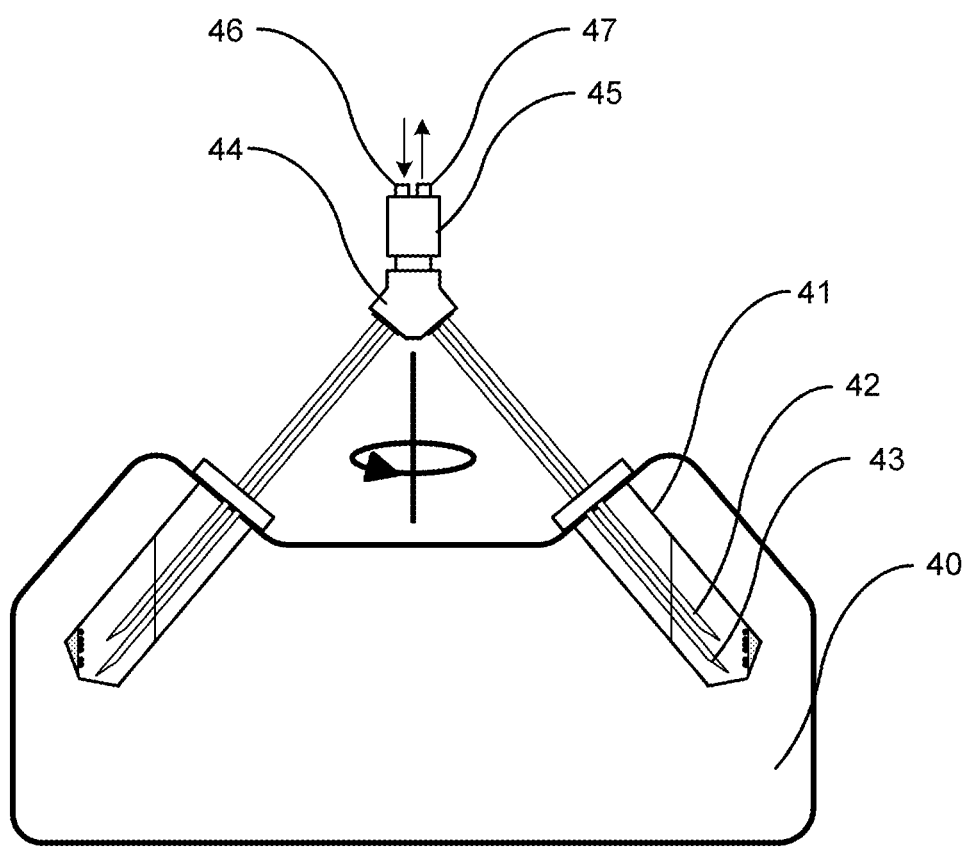
Figure 5B:
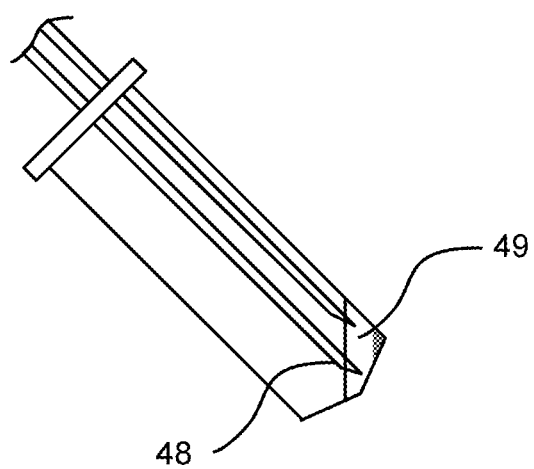
Figure 5C:
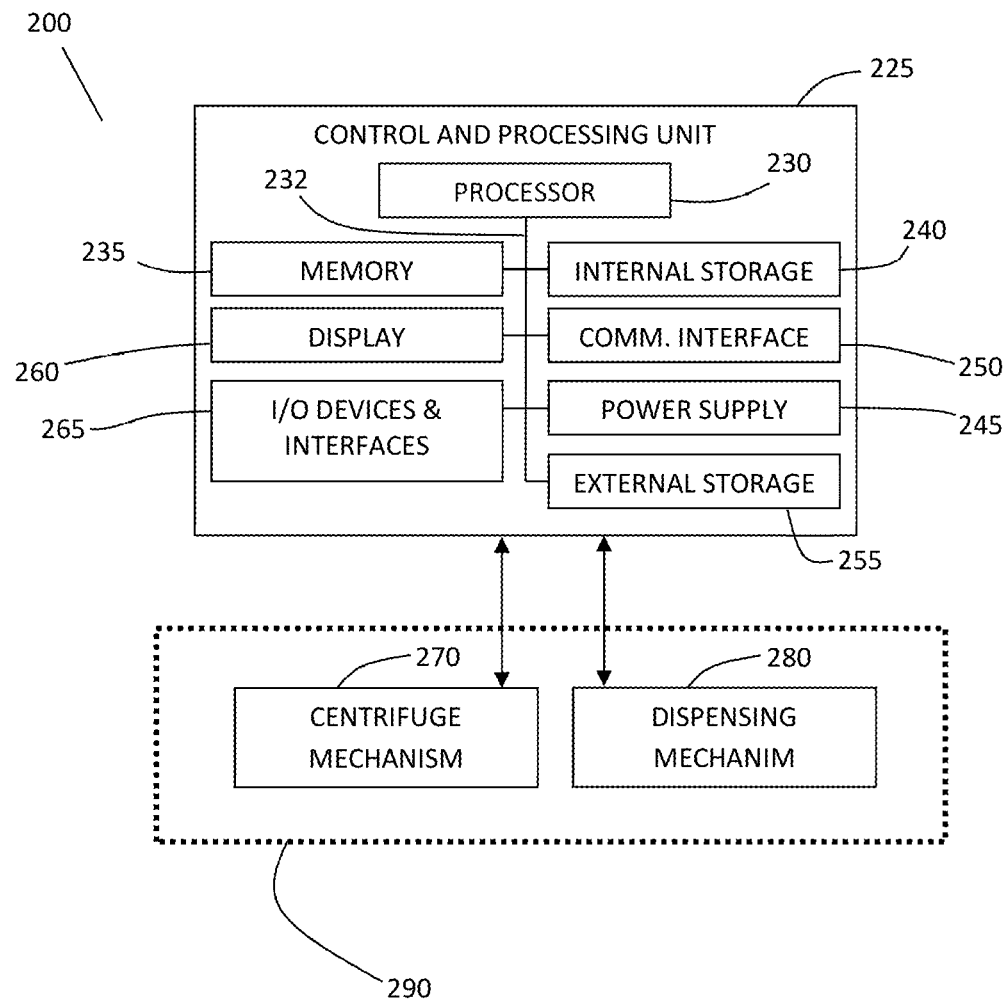
FIG. 5(c) illustrates an example control and processing system.

FIGS. 5(a)-(c) illustrate an example implementation of an automated device for use in sample pretreatment, including a centrifugation mechanism that is integrated with a washing mechanism. FIG. 5(a) shows a diametrical cross-sectional view of a centrifuge with a closed aspirant path. The centrifuge is powered by a motor capable of achieving speeds and centrifugal forces described in the aforementioned embodiments.

Rotor 40 contains receptacles for a plurality of pretreatment tubes 41. A dispensing tube 42 and an aspirant tube 43 are inserted into the pretreatment tube 41 by piercing the pierceable top cap of the pretreatment tube. Dispensing tube 42 and aspirant tube 43 may be provided according to a number of different configurations, such as concentrically, or in a parallel/adjacent configuration as shown in FIG. 5 The dispensing and aspiration tubes, or the plurality of dispensing tubes and aspiration tubes in the case of multiple pretreatment tubes for simultaneous pretreatment, terminate at a manifold 44 which is fluidically connected to a rotating union 45. The rotating union 45 is provided to allow fluidic connection during rotor rotation of the dispensing and aspiration paths to entrance and exit tubes 46 and 47 respectively which are stationary. Such rotating unions are available commercially and may be designed for rotational speeds disclosed herein.

Entrance tube 46 and exit tube 47 may be connected to a dispensing fluid source and waste reservoir respectively, each of which are provided with a dispensing mechanism (such as a peristaltic pump or a syringe pump) for independently dispensing and aspirating fluids. The vortexing, dispensing, and aspiration actions may be controlled independently by the device in accordance with a pre-programmed treatment protocol, following one or more of the steps outlined in FIG. 1(a)-(m), in an automated fashion, instead of a manual fashion. Vortexing may be accomplished, for example, by varying rotational speed, rotational stop/start cycles, rapid alternating rotational direction cycles, and other suitable motions of rotor 40. Alternatively a vibratory mechanism may be applied to the rotor at rest or located on the rotor to apply the forces necessary to resuspend sediment and mix the fluids as required by the pretreatment process described. For example the centrifuge tube may be directly vortexed by a motorised orbiting mechanism. Alternatively a piezo driven vibrator or a motorised vibrator comprising a motor and an eccentric mass on its rotating shaft may be employed in this respect. Following sedimentation steps, aspiration may be performed while rotor 40 rotates at a speed for which the cushioning liquid and cells are held in the sedimentation region with the aspiration tube so positioned as to prevent disturbance of the sedimented microbial cells and avoid aspiration of the cushioning liquid or the microbial cells. With proper placement of the aspiration tube, a small residual fluid volume may be achieved which in turn may increase the wash efficiency. For example a residual volume of 100 ul, 50 ul, or 25 ul may be achieved. For example FIG. 5(*b*) illustrates an aspiration tube placement 48 and residual fluid volume 49 which may be achieved without disturbing the sedimented cells and the cushioning fluid when aspiration occurs during rotor rotation.

The pretreatment protocol may be performed with the automated centrifuge washer in the following manner. With reference to FIG. 1, the sample insertion steps (b) may be performed manually and the pretreatment tubes so prepared are placed in the centrifuge washer. The dispensing and aspiration tubes are inserted into the pretreatment tubes as described above and the manifold connections made. The centrifuge washer is pre-programmed and operated in accordance with the desired parameters for the subsequent series of vortexing, centrifugation, aspiration and dispensing steps analogous to the steps of FIG. 1(*c*) to (*l*) in order to perform the sample pretreatment and washing actions. It is to be understood that some or all of the steps shown in FIGS. 1(*c*)-(*l*) may be automated without re-orienting the pretreatment tube. The pretreatment tubes are then removed from the centrifuge washer and the aspiration step of FIG. 1(*m*) is performed manually.

As shown in FIG. 5(*c*), centrifuge mechanism 270, and liquid dispensing mechanism 280, may be connected to, or connectable to, a control and processing unit 225 for controlling the operation of the liquid dispensing and centrifuge mechanisms according to the presently disclosed sample pretreatment methods. Control and processing unit 225 may include computer or processing hardware such as one or more processors 230 (for example, a CPU/microprocessor), bus 232, memory 235, which may include random access memory (RAM) and/or read only memory (ROM), one or more internal storage devices 240 (e.g. a hard disk drive, compact disk drive or internal flash memory), a power supply 245, one more communications interfaces 250, external storage 255, a display 260 and various input/output devices and/or interfaces 255.

Although only one of each component is illustrated in FIG. 5(*c*), any number of each component can be included in the control and processing unit 225. For example, a computer typically contains a number of different data storage media. Furthermore, although bus 232 is depicted as a single connection between all of the components, it will be appreciated that the bus 232 may represent one or more circuits, devices or communication channels which link two or more of the components. For example, in personal computers, bus 232 often includes or is a motherboard.

In one embodiment, control and processing unit 225 may be, or include, a general purpose computer or any other hardware equivalents. Control and processing unit 225 may also be implemented as one or more physical devices that are coupled to processor 230 through one of more communications channels or interfaces. For example, control and processing unit 225 can be implemented using application specific integrated circuits (ASICs). Alternatively, control and processing unit 225 can be implemented as a combination of hardware and software, where the software is loaded into the processor from the memory or over a network connection.

Control and processing unit 225 may be programmed with a set of instructions which when executed in the processor causes the system to perform one or more methods described in the disclosure. Control and processing unit 225 may include many more or less components than those shown.

FIGS. 6(*a*)-(*e*) illustrate alternative devices which allow automation of some steps of the pretreatment process. FIG. 6(*a*) portrays an elutriation device 300 which is operated in accordance with the principles of counterflow centrifugal elutriation. The elutriation device consists of an inlet tube 301, a conical collection chamber 302 opening in the direction of fluid flow, and an exit cone 303 and outlet tube 304. The elutriation device is placed in a centrifuge rotor and rotated such that the centrifugal force 306 or a sufficient component thereof is directed along the axis of the elutriation device. The fluid suspension is passed through the device flowing from the inlet tube 301, through the collection chamber 302, and exiting through the outlet tube 304. While passing through the collection chamber the particles are subjected to centrifugal forces which oppose the flow direction such that particles with sedimentation coefficients less than a predetermined magnitude are prevented from flowing out of the collection chamber as the fluid flows outward through the chamber outlet 304. The collection zone 306 within the collection chamber is dependent on the centrifugal force and flow velocity both of which vary with position and can be predetermined by choosing appropriate chamber dimensions and centrifuge operating speed.

In the context of the current disclosure the initial pretreatment steps of FIG. 1(*a*) to (*c*) are completed in a separate pretreatment vessel and the pretreatment fluid/sample mixture is passed through the elutriation device as described above. The cells thereby remain suspended in the collection chamber while the full volume of the pretreatment fluid mixture is passed through the chamber. A further volume of wash buffer is passed through the chamber so as to displace the pretreatment fluid and produce a clean cell suspension thus eliminating any contaminants that may be detrimental to subsequent sample processing. In this embodiment the presence of the cushion liquid is not required as cells are held in suspension throughout the centrifugal process and therefore loss of cells due to entrapment or adsorption on the chamber surface will not occur. The final pretreated cell suspension is obtained by lowering the centrifuge speed and/or increasing the flow rate thereby allowing the cell suspension to exit through the outlet tube 304 to a pretreated sample collection device. Alternatively the cell suspension may be removed by reversing the flow and removing the fluid from the chamber via the inlet tube 301 either during or after stopping centrifugal rotation.

Since it is also generally necessary to concentrate the cells in a smaller fluid volume than the original sample, the elutriation chamber should be of an appropriate size to allow extraction of the suspended cells into the desired pretreated sample volume. Thus an elutriation chamber volume may be similar in size to the final sample. For example, the pretreatment fluid/sample volume used in examples herein is approximately 1.5 ml and a preferred final clean cell suspension volume is approximately 50 µl for some applications. For a typical elutriation chamber geometry with a volume of approximately 50 µl and typical benchtop centrifuge parameters the elutriation flow rate is limited to approximately 1 µl/second for which the total elutriation time amounts to processing times of approximately 30 minutes. This processing time can be substantially reduced by initially performing steps (a) to (f) followed by steps (l) and (m) of FIG. 1 to obtain a concentrated pretreatment fluid/sample volume and performing the wash steps in the current elutriation device with the reduced volume.

Figure 6A:
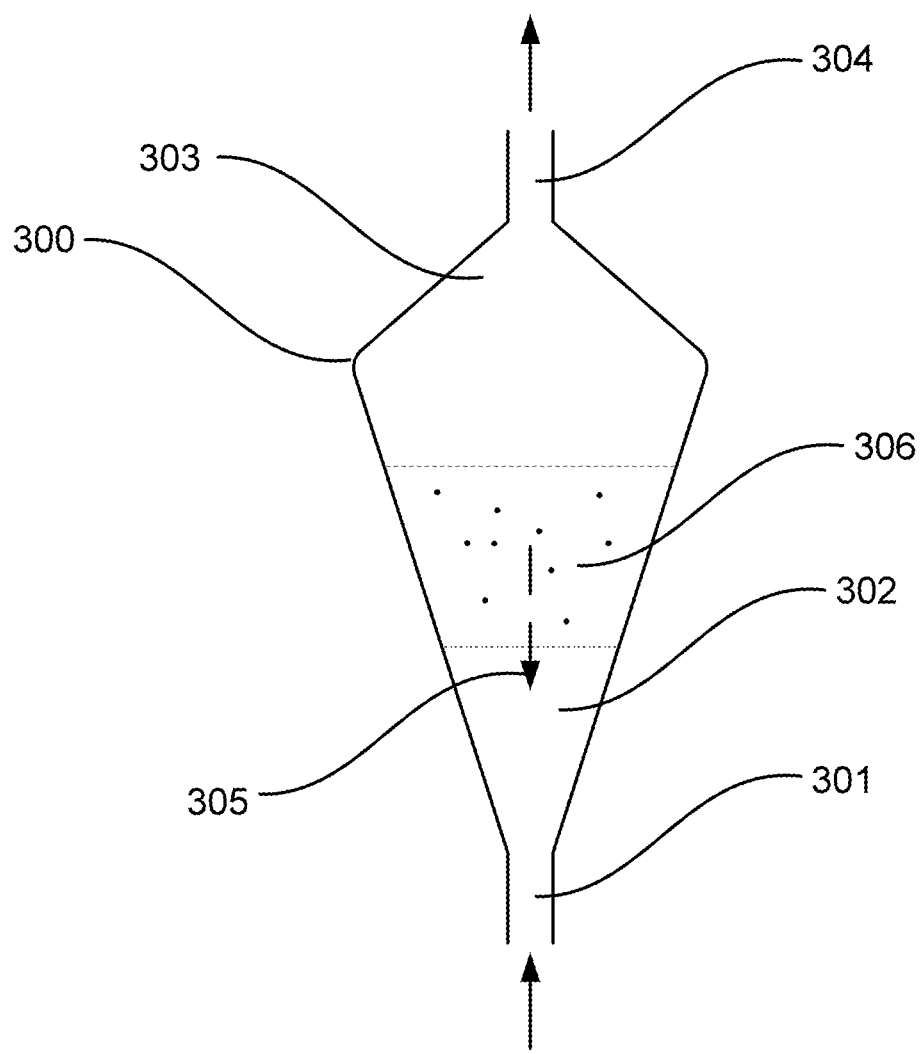
FIGS. 6(a) to (f) illustrate alternative example embodiments for automation of the sample pretreatment method.
Figure 6B:
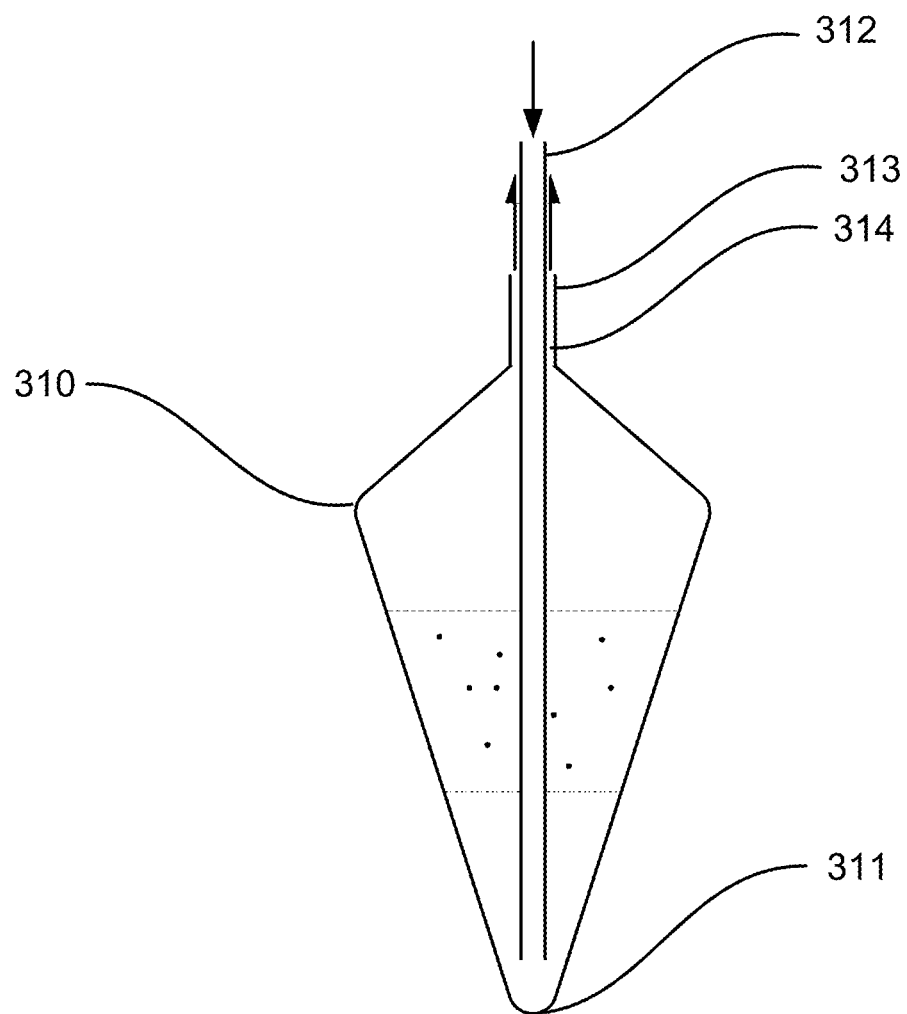
Figure 6C:
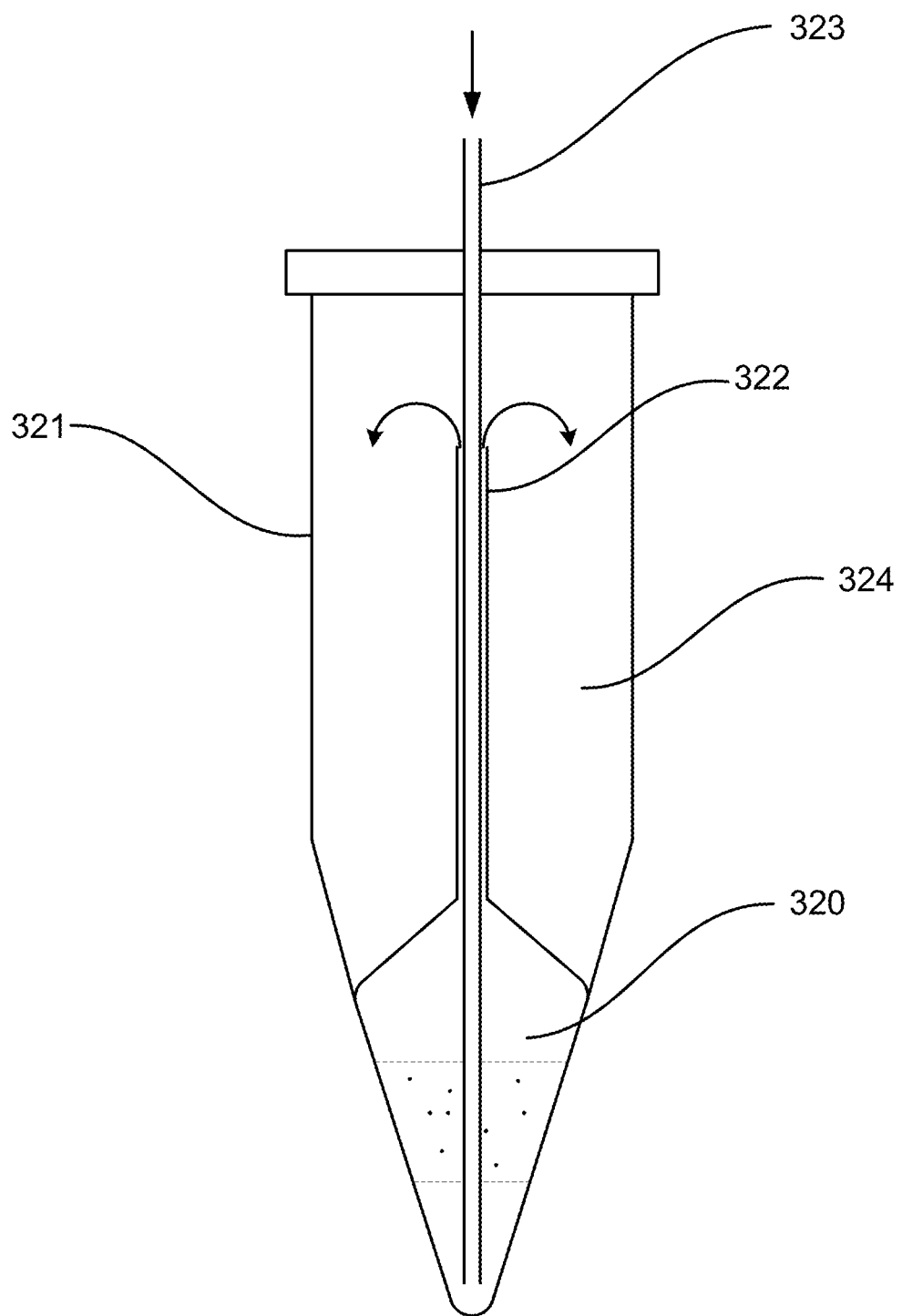

An alternative pretreatment device 310 is shown in FIG. 6(b) which is similar in function to the elutriation device of FIG. 6(a) but differs in some aspects. In this case the elutriation chamber has a closed bottom 311 and the inlet tube 312 is inserted through the outlet tube 313 such that the incoming fluid is dispensed close to but at a predetermined distance away from the bottom of the tube. The outgoing fluid flows from the annular outlet 314 created by the inlet and outlet tubes. The operation of this device is similar to that of the elutriation device described above but its design allows access to both the chamber inlet and outlet from one end of the device. A related embodiment is shown in FIG. 6(c) in which the elutriation chamber 320 is integral to a centrifuge tube 321 and the elutriation chamber outlet tube 322 exits into an isolated waste chamber 324. A similar embodiment can be envisaged for the flow-through embodiment of FIG. 6(a). The waste chamber prevents contamination of external waste flow paths and retains all fluid waste within the device which is advantageous for safe operation and disposal of potentially hazardous sample fluids. For this embodiment it is preferred to remove the cell suspension by drawing the fluid from the chamber through the inlet tube 323 in the reverse direction to the fluid flow during operation. The outlet tube 322 extends beyond the surface of the waste fluid under the conditions prevailing when washing is complete and the clean cell suspension is removed from the elutriation chamber.

Figure 6D:
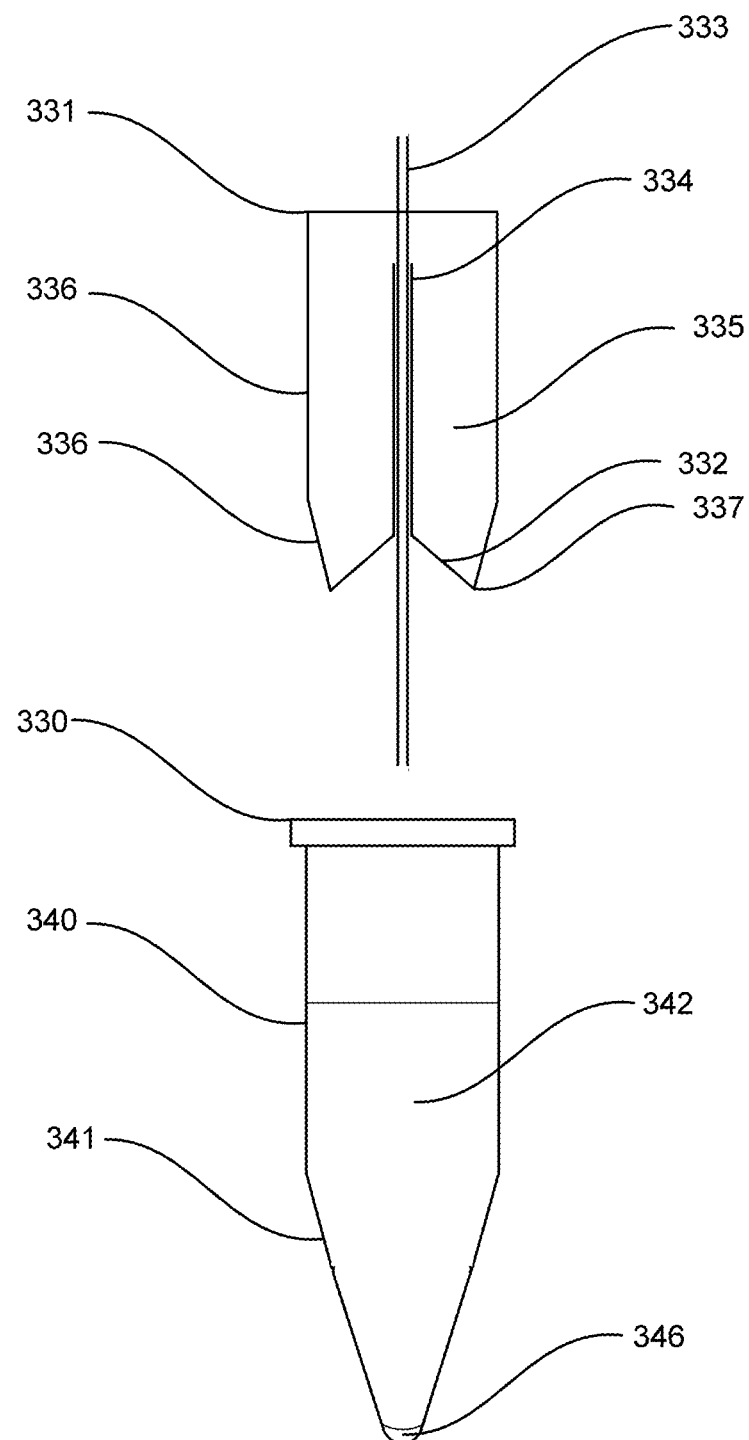
Figure 6E:
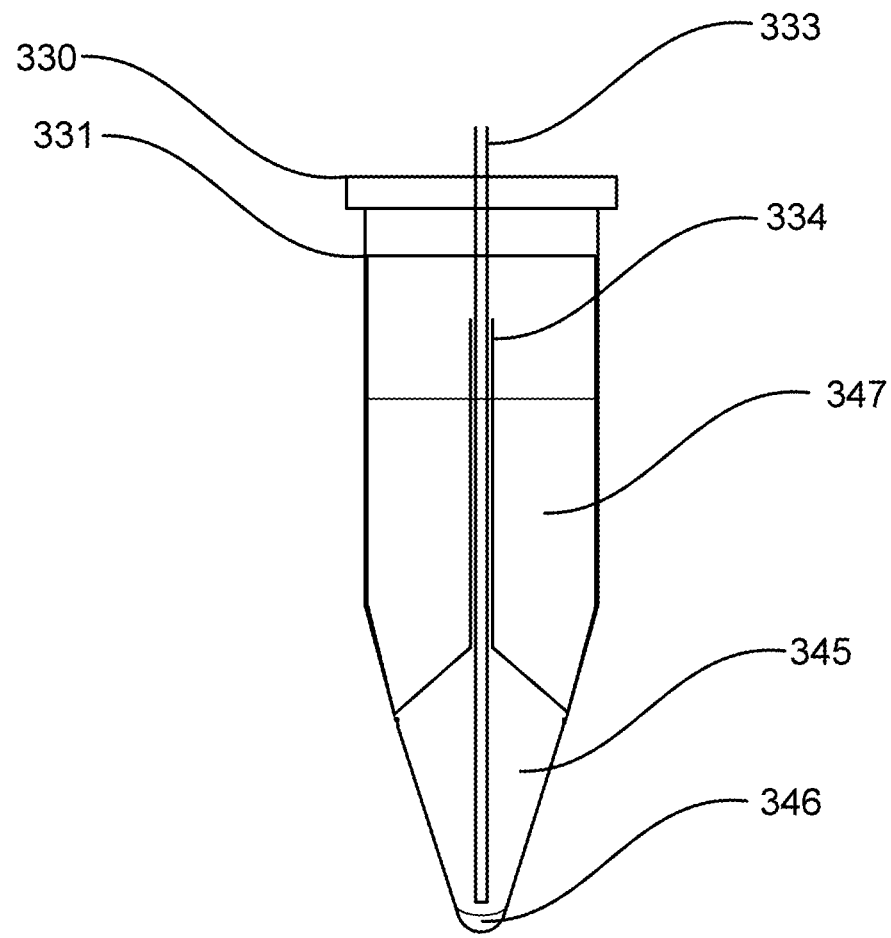

A further embodiment is shown in FIGS. 6(d) and 6(e), which extends the concept of FIG. 6(c) to a two part device consisting of a first part 330 which is the centrifuge tube and the second part 331 which includes the elutriation exit cone 332, inlet tube 333, outlet tube 334 and waste chamber 335 as shown in FIG. 6(d). The main body of the second part 331 has a cylindrical outer surface 336 and is insertable into the cylindrical portion 340 of the first part and may be pushed into said first part until the bottom portion 336 of the second part engages with the bottom portion 341 of first part as illustrated in FIG. 6(e). The extremity of the bottom portion of the second part is so formed that it seats tightly with the bottom portion of the first part such that a seal is obtained between the first and second parts thus forming an isolated chamber 345 with inlet tube 333 and outlet tube 334. A deformable portion or material such as a rubber gasket may be provided at the extremity 337 of the second part to provide an adequate seal.

The pretreatment fluid/sample mixture 342 containing the cushioning fluid is initially dispensed into the first part 330 and subjected to centrifugation such that the microbial cells sediment on the surface and periphery of the cushioning fluid 346 at the bottom apex of the tube. Optionally the first part 330 contains a volume of blood lysis reagent and cushioning liquid as described previously and the sample is inserted, followed by mixing so as to produce a mixture and effect lysis of the blood cells, and is subsequently subjected to centrifugation.

Following sedimentation of the microbial cells the second part 331 is inserted into and pushed to the bottom of the first part 330 sufficiently slowly to allow the supernatant so displaced to flow through the outlet tube and into the waste chamber resulting in the engaged position of the parts as shown in FIG. 6(e). In this way, a large portion of the supernatant 347 is separated from the chamber 345 and a washing step may proceed within the smaller chamber volume. Hence the washing function can proceed by rotating the engaged tube assembly while flowing wash fluid through the inlet tube into the chamber. Cells which were sedimented on the cushioning liquid at the bottom of the chamber may be disturbed by the incoming flow but will be retained in the chamber due to centrifugal forces which exceed flow induced forces on the cells due to the controlled flow rate. The wash fluid will displace pretreatment fluid and non-sedimenting particles to produce a clean fluid in the chamber.

Figure 6F:
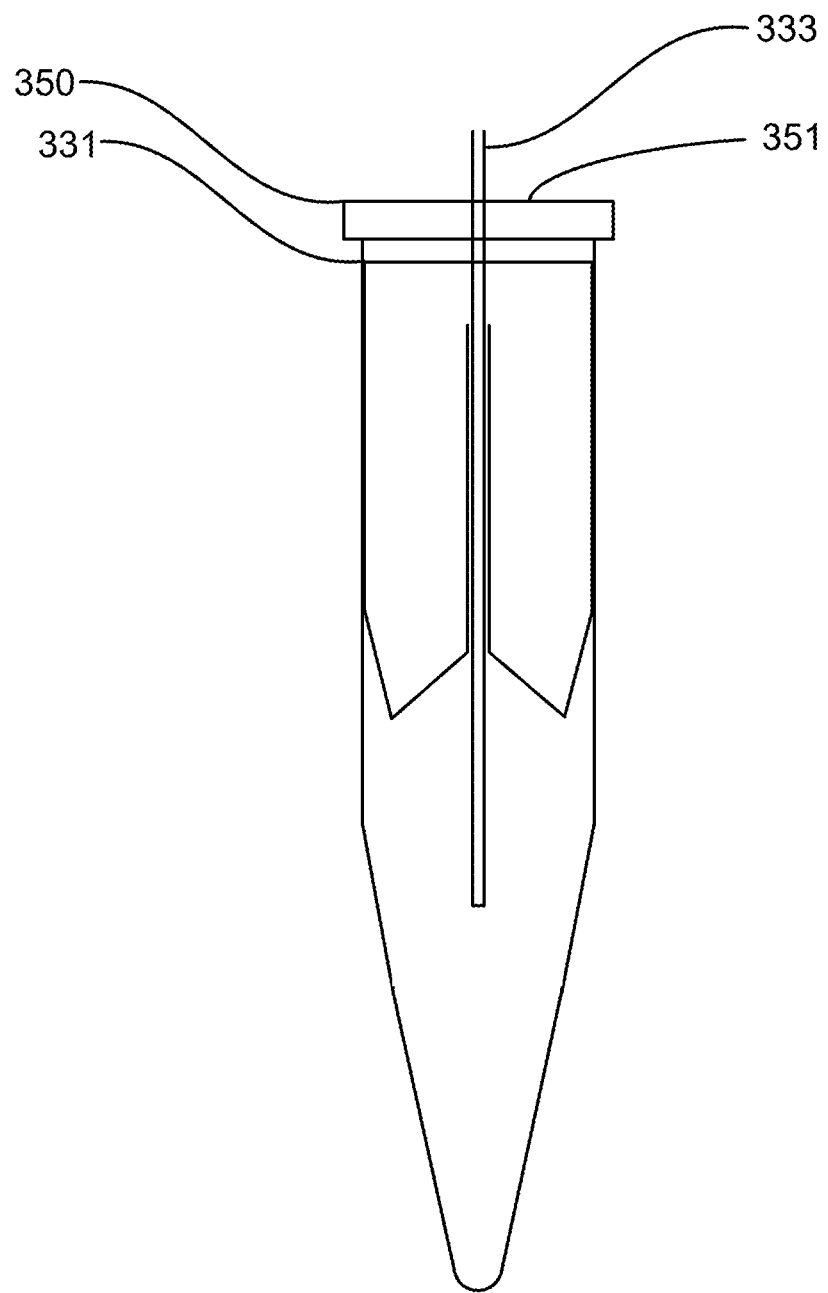

In order to improve the washing efficiency the fluid in the chamber may be mixed by vibration or vortexing intermittently in order to resuspend particulate that may attach to the chamber wall and to dilute fluid zones of relative stagnation. Furthermore the density of the wash fluid may be increased to a level exceeding that of the pretreatment fluid/sample mixture by, for example, the addition of trehalose to provide a more effective displacement of pretreatment fluid/sample mixture from the chamber. FIG. 6(f) illustrates an alternate embodiment for which the second part 331 is inserted into a first part 350 prior to operation of the device. Optionally the inlet tube 333 may be a separate device which is inserted through a pierceable membrane 351 at the top of the tube. The inlet tube 333 may optionally also be used to insert the sample or the pretreatment fluid/sample mixture into the tube.

Integration of Sample Pre-Treatment with Downstream Molecular Processing

In some embodiments, the preceding embodiments may be employed for the initial extraction and concentration of microbial cells, followed by downstream methods for identifying microbial cells using reverse transcription-PCR (RT-PCR); the reverse transcription of rRNA into complementary DNA (cDNA), with subsequent amplification and detection of the cDNA by PCR. The amplification of cDNA may optionally be performed simultaneously, or serially, with the amplification of genomic DNA, where the cDNA and the gDNA are employed for identifying different genotypic taxa of the microbial cells. The gDNA may be obtained from the same lysate as the rRNA.

Microbial cells that may be identified according to embodiments of the disclosure include bacteria and fungi. In some embodiments, rRNA from the microbial cells is released, and a reverse transcription step is employed to obtain cDNA, where the cDNA is representative of a first genotypic taxa level, and where the cDNA, if present, is subsequently amplified and detected in order to identify the first genotypic taxa level of the microbial cells. Simultaneously or sequentially, amplification and detection of gDNA released from the microbial cells is employed to identify a second genotypic taxa of the microbial cells of a second level, where the second level is of a lower level than the first level. In another embodiment, mRNA may be used as a target for the microbial identification, and a reverse transcription step is employed to obtain cDNA and where the cDNA, if present, is subsequently amplified and detected in order to identify the second genotypic taxa level of the microbial cells. This embodiment may be preferred when the information on the viability of the microorganism is desired. As it is known in the art, mRNA content of microorganisms drop following the cell death.

Figure 7A:
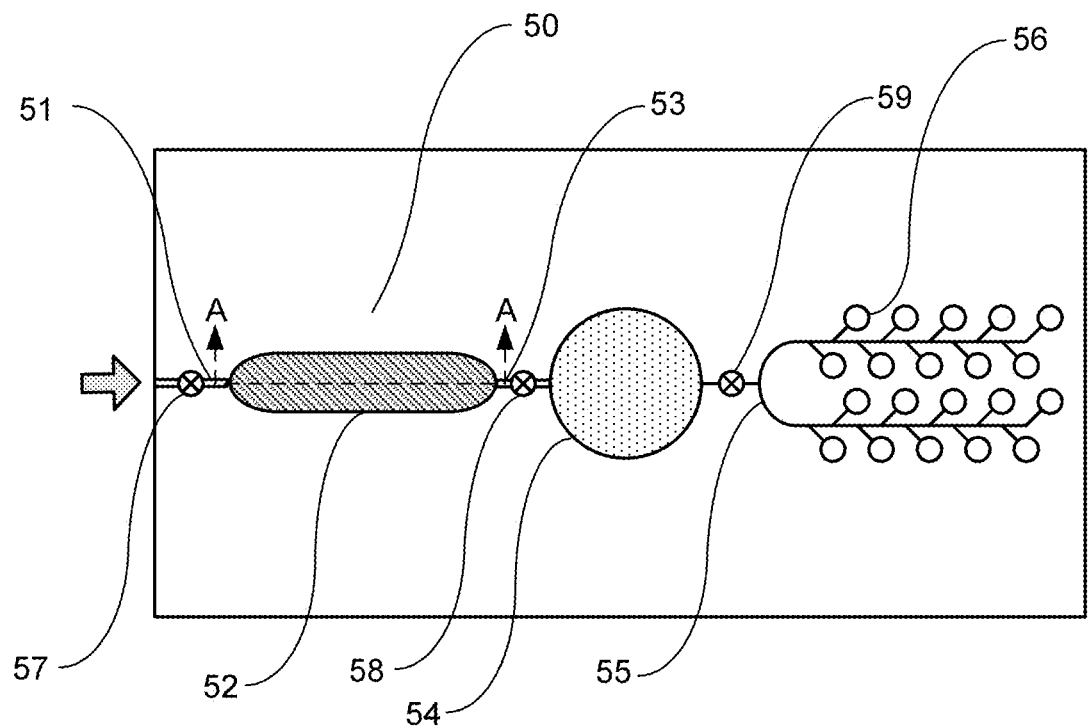
FIG. 7(a) schematically depicts an example fluidic device for performing electrical cell treatment, rRNA reverse transcription, PCR, and amplicon detection.

An example module for performing electrical treatment, reverse transcription of rRNA, PCR, and amplicon detection is schematically presented in FIG. 7(a). Electrical channel 52 includes an inlet port 51 through which fluid sample and other fluids may be introduced. Electrical channel 52 also includes outlet port 53, which is in fluid communication with downstream thermal chamber 54, where the reverse transcription of rRNA and PCR may be performed. Flow along electrical channel 52 is provided by a pressure differential between inlet 51 and outlet 53 ports.

The device may include additional fluid features, such as valves for opening and closing ports 51 and 53. For example, valves 57 and 58 may optionally be provided at the inlet 51 and outlet ports 53 of electrical channel 52, and valve 59 is optionally provided at the outlet of thermal chamber 54. Valves 57, 58 and 59 may employ any suitable valving mechanism compatible with a microfluidic channel, including, but not limited to, pinch valves, ball valves, disc valves, plug valves. Valves 57 and 58 may be provided to assist in controlling evaporation of the liquid during electrical lysing and treatment and to control the exposure of the fluid to electrical field and thermal effects. For example, valves 57 and 58 may be useful in ensuring that a sufficiently high temperature is achieved for sufficient and/or efficient electrical lysis (for example, some organisms, such as fungi, may require higher temperatures and/or temperature rates of change for efficient lysis).

Figure 7B:
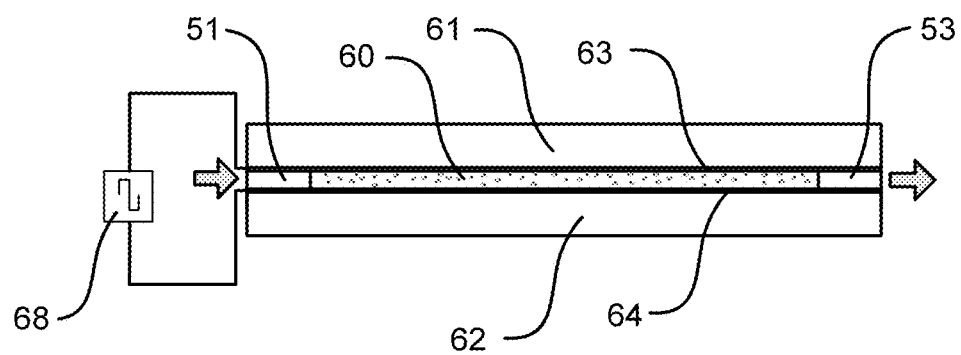
FIG. 7(b) schematically depicts the cross section A-A of electrical chamber 52 of FIG. 7(a) and shows the application of voltage pulses to the electrical chamber.

Referring now to FIG. 7(b), cross section A-A of electrical chamber 52 of FIG. 7(a) is shown along with a circuit for applying voltage pulses to the electrical chamber. Electrical treatment of the processed sample may be performed, for example, according to methods disclosed in co-pending PCT Application Number PCT/CA2012/000698, titled "METHODS AND DEVICES FOR ELECTRICAL SAMPLE PREPARATION" and filed on Jul. 25, 2012, which is incorporated herein by reference in its entirety. The device includes a thin channel defined on one side by the top plate 61, upper electrode 63 and on the opposite side by base plate 62 and lower electrode 64. The upper and lower portions are separated by a thin spacer, in which material is removed to form the channel cavity. The spacer may be made from a dielectric material, which may be slightly deformable under an applied clamping pressure, or which is bonded to the upper and lower surfaces of the channel cavity. The spacer thus defines the side walls of the channel, provides the fluid seal, and electrically insulates the top and bottom electrodes from each other.

The lower electrode 64 and upper electrode 63 are electrically isolated from the base and top plates (substrates) by lower and upper electrically insulating layers. In accordance with thermal requirements, thermal insulating layers may also be provided which may be separate from or be suitable selections of the electrical insulating material. The channel has dimensions H×W×L which, in one example implementation, used for the tests in the following examples, was 0.2×6.4×15 mm$^3$. The two electrodes 63 and 64 are intended for inducing an electric field across the channel resulting in the establishment of an ionic current.

As per the methods disclosed in PCT Application Number PCT/CA2012/000698, the application of suitable amplitude modulated electric pulse train by the external voltage source 68 on the two electrodes, establishes an electric field in the electric chamber. The electric field results in ionic current and Joule heating of the liquid. As the duration of the electric pulse train and, consequently, the accompanying Joule heating is brief, this mechanism of heating is known as flash heating. The coupled effect of the electric field acting on the cells and the flash heating of the liquid causes the microbial cells to lyse and intracellular molecules, such as proteins and nucleic acids, to be released from the cell. The lysis process, irreversibly permeabilizes the microbial cell membrane and readily supports molecular exchange in and out of the cell.

The thermal properties of the channel are dependent on many different channel parameters. For example, the channel conductivity and heat capacity can be controlled according to the geometry and/or thickness of the metal electrode. Most electrodes will have a high thermal conductivity, but the thermal properties of the channel can be tailored by selecting an appropriate electrode thickness to provide a suitable heat capacity and an appropriate (e.g. thermally insulating) substrate upon which the electrodes are supported.

Accordingly, one or more of the channel electrodes may be provided as a metal foil or coating having a high thermal conductivity and/or a high heat capacity relative to the total volume of fluid in the channel to promote rapid cooling after electrical treatment, while at the same time providing a sufficiently small heat capacity such that the flash heating can produce a rapid temperature rise within the channel during the application of the voltage pulses (for example, a temperature rise greater than approximately 250 degrees Celsius per second).

Generally speaking, the following ranges may be employed for electrical processing of microbial cells. The electric field strength within the channel that is produced by the application of the voltage pulses may range between approximately 200 V/cm<E<50 kV/cm, depending on the type of cell that is to be processed and the degree of electrical processing that is desired. A range of approximately 2 kV/cm<E<30 kV/cm may be preferable for lysis of microorganisms and using the lysate for performing diagnostic tests on the released nucleic acids.

According to different example implementations, the pulse width of individual voltage pulses may range between approximately 1 µs<$t_p$<10 ms, depending on the type of cell that is to be processed and the degree of electrical processing that is desired. A range of approximately $t_p$<1 ms may be preferable for avoiding the electrical breakdown of the dielectric coating in the case of blocking electrodes, minimizing the accumulation of the electrochemical products in the case of non-blocking electrodes. A range of approximately $t_p$>10 µs is preferred for lowering the high frequency demands of driving electronics.

According to other example implementations, the time duration over which the voltage pulses are applied may be less than about 5 s, depending on the type of cell that is to be processed and the degree of electrical processing that is desired. In some cases, such as to minimize the heat induced degradation of target macromolecules and decrease the power demands of the driving electronics, an effective time duration for electrical processing may be less than about 100 ms.

According to other example implementations, the ionic strength of the cell containing liquid may range from approximately 0.1 mM<I<100 mM, depending on the ionic composition of the initial sample that is to be processed and the degree of electrical processing that is desired. In some cases, when filtering is used and fluid exchange is allowed, a more suitable range for the ionic strength may be from approximately 0.1 mM<I<10 mM, or 0.2 mM<I<1 mM.

According to other example implementations, the peak temperature of the liquid within the channel during the application of voltage pulses may range from approximately 30° C.<$T_p$<250° C., depending on the type of cell that is to be processed and the degree of electrical processing that is desired. In some applications, such as lysis of microorganisms and using the lysate for performing diagnostic tests on the released nucleic acids, it may be preferable for the temperature range to lie within approximately 80° C.<$T_p$<200° C.

The heating rate of the liquid for the electrical processing may be greater than approximately 250° C./s, depending on the type of cell that is to be processed and the degree of electrical processing that is desired. In some cases, such as lysis of Gram positive bacteria, fungi, and spores, a suitable range may include rates greater than about 2000° C./s.

The cooldown time of the liquid following electrical treatment may be less than approximately 1 s, depending on the thermal sensitivity of the target macromolecule. In some cases, such as when the target macromolecule is particularly sensitive, a preferred range may include times below about 100 ms.

The macromolecular content of the cell may undergo a transformation in the period between turning on of the electric field and cooling down of the liquid. This process, referred to herein as "E-treatment", may render nucleic acids, such as rRNA and gDNA, more accessible to enzymes, thus improving the efficiencies of the ensuing nucleic acid reverse transcription and amplification processes. Moreover, E-treatment may be effective in inactivating most of enzymes that are released from microbial cells or have been left in the channel from residual blood cell debris. Thus, the deleterious inhibitory effects of such enzymes in the subsequent processes may be minimized. Other inhibitors that hinders transcriptase and/or polymerase activity may be also rendered less effective or benign through E-treatment.

Referring again to FIG. 7(a), according to one example implementation, thermal chamber 54 is provided for performing reverse transcription of rRNA followed by the PCR. (e.g. one-step RT-PCR). The RT-PCR master mix may be introduced in liquid form or may be present in the chamber in dry format prior to the introduction of the sample. After the introduction of the treated sample into thermal chamber 54 and mixing with the RT-PCR master mix, the resulting mixture is incubated to perform reverse transcription of rRNA and thermally cycled to perform PCR. In one example embodiment, the heating and cooling operations may be provided by placing the device on a Peltier device. In other embodiments, heating may be provided by electrical resistance contact heaters, radiant heating, or convection heaters and cooling may be provided by circulating fluids, forced air flow, and other suitable methods.

According to this example implementation, the nucleic acid sequences of the rRNA are reverse-transcribed to complementary DNA (cDNA). The reagent for reverse transcription typically contains reverse transcription enzyme, deoxy nucleotide triphosphate mixture (dNTPs), an appropriate buffer with magnesium or manganese cofactor, and optionally RNase inhibitor. The reverse transcription can be any RNA-dependent DNA polymerase enzyme known in the prior art such as Moloney Murine Leukemia Virus (M-MuLV) reverse transcription, Avian Myeloblastosis Virus (AMV) reverse transcription and *Thermos thermophilus* (Tth) DNA polymerases.

The primers can be non-specific random primers or gene-specific primers. In some embodiments, nucleic acid sequences of no more than 500 bases will be reverse transcribed to cDNA using gene-specific primers. The specific primers can be primer sets or degenerate primers. One or more target nucleic acid sequences of one or more microorganisms will be reverse transcribed at the same time.

In one embodiment, three sets of primers, respectively targeting Gram-positive, Gram-negative, and fungal rRNA, are simultaneously used (multiplexed). Reverse transcription takes place at an appropriate temperature depending on the enzyme and on the primer annealing temperature (for example, for no more than 10 minutes). In addition, the reaction mixture may contain ingredients for performing PCR, including Taq DNA polymerase, deoxy nucleotide triphosphate mixture (dNTPs). Optionally, RNase inhibitors, Taq DNA polymerase antibody for hot-start, adjuvants to inhibit PCR inhibitors (example; bovine serum albumin) or to enhance PCR performance (example; betaine) may be included.

The PCR cycles may involve an initial incubation at 94-98° C. for 2-5 minutes, to inactivate the reverse transcription enzyme from the first stage, and to activate DNA polymerase for PCR, followed by a 2-step or 3-step thermal cycling. The thermal chamber may contain one or more specific primer sets or degenerate primers. In addition to the primers, one or more components of PCR reagent may also be provided in the chamber in a dry format, such as freeze-dried reagent, or ambient temperature dried reagent employing appropriate stabilizers.

In the example implementation illustrated in FIG. 7(a), in order to perform the multiplexed detection of amplicons produced during PCR, the contents of thermal chamber 54 are transferred into plurality of wells 56 via channels 55. Each well may be pre-filled, optionally in dry format, with appropriate nucleic acid detection reagents. Accordingly, spatially multiplexed detection may be performed. In one embodiment, spatially multiplexed detection may be performed using molecular beacons for signal generation. In other embodiments, multiplexed detection may be performed by melting curve analysis of the amplicons stained with a double-stranded DNA dye, or employing fluorophores with different emission wavelengths.

In one embodiment, the detection is performed using molecular beacons. Molecular beacons have a stem-and-loop structure, with the loop portion being complementary to a single-stranded DNA target while the stem is formed by 6 to 8 nucleotides from two complementary arm sequences. A fluorophore (such as, but not limited to, fluorescein (6-FAM) is attached to the end of one arm, while a quencher (such as but not limited to dabcyl succinimidul ester) is attached to the other arm. In the absence of the specific target, the molecular beacon remains in a "dark" state. In the presence of the specific target, the fluorophore and quencher are separated and the fluorescence emission, resulting from excitation by light with appropriate spectrum, can be detected by an optical system. In the preferred embodiment, the excitation and detection are performed using epi-fluorescence microscopic objective that may utilize an LED light source. In some embodiments, the molecular beacon may be stored in wells 56 in a solution or in dry format. According to one example implementation, a primer pair to detect all bacterial 16S rRNA genes may be CGGCTAACTCCGTGCCAGCAG (SEQ. ID. 1) and ATCTCTACGCATTTCACCGCTACAC (SEQ. ID. 2), which targets a hypervariable region of target bacterial species (nucleotides 504 to 697 using *Escherichia coli* O104:H4 str. 2011C-3493 as a reference). A primer pair to detect target fungal species could be AGGGGGAGGTAGT-GACAATAAAT (SEQ. ID. 3) and CAAAGTTCAACTAC-GAGCTT (SEQ. ID. 4), which targets a variable region of eukaryotic 18S rRNA (nucleotides 436 to 622 using *Candida albicans* AB013586 as a reference). The molecular beacons can subsequently be used to identify specific nucleotide patterns within this amplified region to distinguish between the pathogens of interest. For example, a molecular beacon designed to detect target Gram-negative species could be 6-FAM-5'-CCGAGCGGTGCAAGCGT-TAATC GGAATTACTGGGCGCTCGG-3'-DABCYL (SEQ. ID. 5), which targets a region of the 16S rRNA gene (nucleotides 541-569 using *Escherichia coli* O104:H4 str, 2011C-3493 as a reference) conserved in all Gram-negative bacteria. Alternatively, a molecular beacon designed to detect target fungal pathogens could be 6-FAM-5'-CCGAGCTCTGGTGCCAGCAGCCGCGGTAAT-TCGCTCGG-3'-DABCYL (SEQ. ID. 6), which targets a region of the 18S rRNA gene (nucleotides 539 to 564 using *Candida albicans* AB013586 as a reference) conserved in all fungi. Using this strategy, target bacterial and fungal blood pathogens can be identified using a small number of primer pairs and several molecular beacons. The molecular beacons could ultimately be multiplexed, allowing one to identify multiple bacterial and/or fungal pathogens in a single chamber.

In another example embodiment, microbial cells may be identified by two-step RT-PCR. Thermal chamber 54 in FIG. 7(*a*) is provided for performing reverse transcription of rRNA. The RT-PCR master mix may be introduced in liquid form or may be present in the chamber in dry format prior to the introduction of the sample. After the introduction of the treated sample into thermal chamber 54 and mixing with the RT-PCR master mix, the resulting mixture is incubated to perform reverse transcription of rRNA. In order to perform the multiplexed detection of the target, the contents of thermal chamber 54, containing cDNA and the master mix required for PCR are transferred into plurality of wells 56 via channels 55. Each well may be pre-filled, optionally in dry format, with appropriate specific primer sets. The nucleic acid detection reagents such as double-stranded DNA dyes may be provided in the RT-PCR master mix and spatially multiplexed detection may be performed by real-time PCR in detection wells 56.

Figure 8:
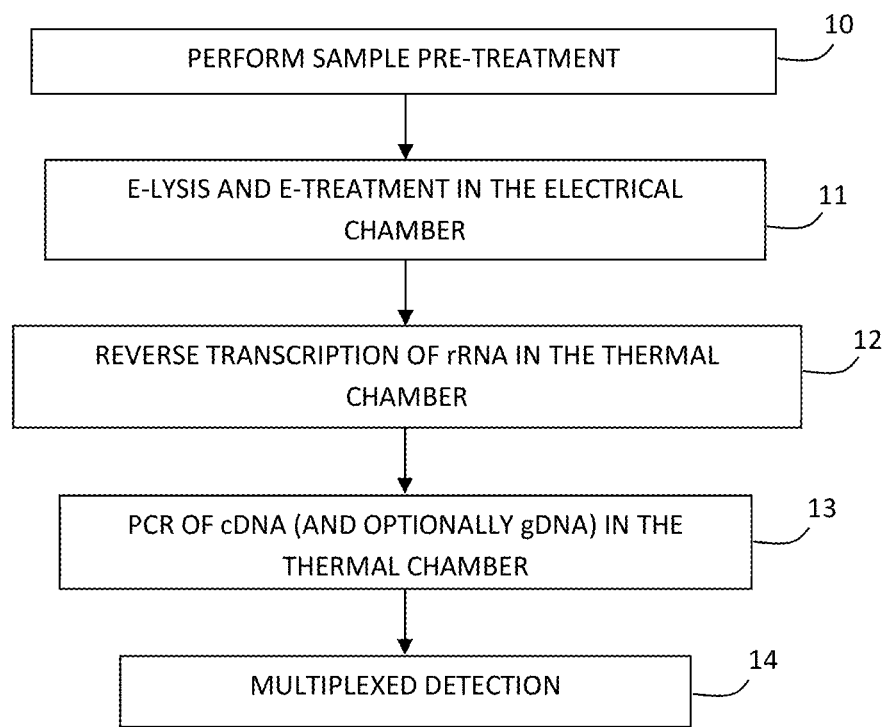
FIG. 8 provides a flow chart illustrating an example method of detecting and identifying microbial cells in a whole blood sample.

In another example embodiment, thermal chamber 54 in FIG. 7(*a*) may be provided for introduction of RT-PCR master mix which may be introduced in liquid form or may be present in the chamber in dry format prior to the introduction of the sample. After the introduction of the treated sample into thermal chamber 54 and mixing with the RT-PCR master mix, the resulting mixture is incubated to ensure proper mixing of the mixture. In this example embodiment, microbial cells may be identified by real-time one-step RT-PCR. In order to perform the multiplexed detection of the target, the contents of thermal chamber 54, containing the cell lysate and the master mix required for RT-PCR are transferred into plurality of wells 56 via channels 55. Each well may be pre-filled, optionally in dry format, with appropriate specific primer sets. The nucleic acid detection reagents such as double-stranded DNA dyes may be provided in the RT-PCR master mix and spatially multiplexed detection may be performed by real-time one-step RT-PCR. Referring now to FIG. 8, a flow chart is provided that illustrates an example method of performing microbial classification and/or identification according to one embodiment (e.g. using RT-PCR followed by signal detection using molecular beacon). In step 10, sample pretreatment is performed according to the preceding embodiments. The result is a cell suspension in a liquid with desired composition that is appropriate for the subsequent sample treatment and nucleic acid amplification steps. The sample pretreatment step may also be useful for substantially reducing or eliminating the presence of DNA fragments from dead microbes that can be introduced while taking sample from infected patients.

Electrical processing, by which the microbial cells are lysed and the intracellular rRNA and genomic DNA are rendered accessible for external enzyme action, is performed in step 11, as described above. Electrical treatment in this step may also inactivate or reduce the effect of enzymes or factors inhibitory to subsequent amplification and detection, in step 12, the pretreated and lysed sample is mixed with an appropriate master mix in the thermal chamber and targeted regions of the rRNA are reverse transcribed into corresponding cDNA. The master mix contains components for performing cycles of PCR amplification on the cDNA or specific regions of gDNA, as shown in step 13.

In the method and embodiments disclosed, the three preceding steps, namely 11, 12 and 13, may be performed in fluidic sequence in a single device in order to prevent or reduce losses in the number of target molecules. Such losses are associated with liquid exchanges and movements in commonly used methods for sample extraction and/or preparation. Accordingly, this aspect of the present method, along with the efficient sample pretreatment step 10, potentially enables achieving a detection limit down to a few microbial cells in the sample.

Performing an assay based on rRNA, as opposed to gDNA, as the primary mode of detection, may provide enhanced sensitivity for two reasons. Firstly, rRNA is not as stable as gDNA and thus foreign rRNA has a much smaller chance of being introduced into the thermal chamber as a major contamination component. Secondly, the number of rRNA molecules becoming available after electrical treatment of step 11, for even a single cell, is in the range of $10^4$, which, according to the methods disclosed herein, will generally exceed the quantity of contaminant background molecules.

Following the completion of step 13, the liquid contains sufficient cDNA and/or amplicons to be split into multiple aliquots and delivered into a plurality of wells, in a manner such that each well receives a statistically significant number of target molecules.

Test Panels for Rapid De-Escalation of Antimicrobial Therapy Based on Processing of Direct Samples In some embodiments, the panel of rRNA tests may be selected to enable rapid de-escalation of antibiotic therapy from one or more broad-spectrum antibiotics to one or more narrow-spectrum antibiotics. Using narrow-spectrum antimicrobial drugs not only provides a benefit in terms of cost reduction, but it also limits the potential for adverse effects such as superinfection and the development of drug-resistant microbes. As noted above, the present embodiments enable the rapid detection and/or identification of infectious agents, which could improve the decision-making process of health care professionals, and help them to administer narrow spectrum antimicrobial drugs at an earlier time. This may prevent the development of resistance, reduce toxicity, and substantially reduce healthcare costs.

Unlike known molecular methods that are focused on the targeted identification of an organism at the species level based on a comprehensive, species-level test panel, such as the Septifast system, selected embodiments described herein provide sufficient information for rapid de-escalation of antimicrobial therapy, without needing to provide full species and/or genus level identification for every expected pathogen. The reduced panels described herein are suitable for effective rapid re-vectoring of antimicrobial treatment because many organisms will respond to a common narrow-spectrum antibiotic, and as such, the test panel need not identify each and every genus and/or species of the expected pathogens, an instead need only identify those organisms or groups of organisms whose presence or absence will impact antimicrobial therapy and guide the selection of appropriate narrow-spectrum antibiotics. In many of the embodiments provided herein, a test panel is selected to provide information that is not exclusive to the genus or species level, but is instead includes a combination of rRNA test results at the kingdom, Gram-status, genus, and species levels.

Accordingly, in some embodiments, a test panel for rapid de-escalation of antimicrobial therapy includes, at a minimum, the following:

(a) one or more primary rRNA tests at the kingdom level to determine whether the organism is a bacterial or a fungal organism;

(b) one or more secondary tests to identify the Gram status of the organism, if bacterial; and (c) one or more tertiary rRNA tests, for each of fungi, Gram-positive bacteria, and Gram-negative bacteria, to identify at least one genus or species of the organism, where the result of the tertiary test is suitable for selecting an appropriate narrow-spectrum antibiotic.

In some embodiments, one or more of the rRNA tertiary tests may be replaced and/or augmented by a strain level test, where the strain level test may be a gDNA test suitable for identification of a selected strain.

It has been found that such test panels are sufficient for rapid de-escalation of antimicrobial therapy from broad spectrum antibiotics to narrow spectrum antibiotics, especially when the test is performed on a direct, non-enriched sample, prior to enrichment or culturing.

The selection of one or more tertiary tests at the species or genus level will depend on a number of factors, such as the nature of the antibiogram, and the availability of suitable antibiotics. Non-limiting examples of test panels are described below. For example, over time, a suitable genus or species level tertiary test for Gram-negative bacteria may change due to changes in pathogen prevalence, changes in antibiotic resistance, and/or the availability of new antibiotics.

In some embodiments, the reduced test panel is selected by mapping the available antibiotics to information associated with the highest levels of pathogenic taxa, and the test panel is selected to include the tests for these highest levels. For example, the test panel may include, at a high level, three multiplex tests for isolating a true positive sample to one of Gram-positive, Gram negative, or fungi. This may be achieved, as noted above, by isolating specific regions of the ribosome belonging to all Gram-positive bacteria, to the exclusion of all others, for example, it becomes possible to identify a true Gram-positive sample. If this same procedure is repeated for all Gram-negative bacteria to the exclusion of all others, it becomes possible to identify a true Gram-negative sample. A third test would isolate and identify a true fungal sample.

This reduction principle may be repeated in a hierarchical format (for example, a decision tree or a flow chart) to determine the set of tests needed to de-escalate antimicrobial therapy. This effectively reduces the very large number of tests for all possible organisms to a subset of tests relevant to antimicrobial re-vectoring.

For example, a suitable test panel may involve a kingdom-based primary test for bacterial vs. fungal organisms, a Gram-status secondary test, and a tertiary test for the genus of *Streptococci*, and an additional species-level tertiary test, provided that the species-level test would enable further antimicrobial de-escalation. For example, a species-level tertiary test for *Streptococcus pneumoniae* would enable further de-escalation, based on presently available antibiotics.

In another example, a suitable tertiary test may be for the genus of *Staphylococcus*, and the test panel may include an additional species-level tertiary test for the species of *Staphylococcus aureus*. A sample testing positive to both of these tertiary tests would be thought to include *Staphylococcus aureus*, and a medical practitioner could subsequently decide to de-escalate antibiotic therapy to Vancomyacin and Oxacillin due to the awareness of potential methicillin resistance. On the other hand, if the sample found to be positive to Gram-positive and *Staphylococcus*, but negative to *S. aureus*, then the medical practitioner may determine that the offending organism is probably Staphylococci other than *S. aureus* and most probably a contaminant, which could lead the medical practitioner to determine that treatment is not warranted.

This principle is illustrated in FIGS. 9(*a*) and 9(*b*). In FIG. 9(*a*), a hierarchical panel diagram is shown in which the number of tests that determines a course of antimicrobial therapy for blood infections has been reduced to nine, FIG. 9(*b*) shows an example of organism identification based on different possible panel test results, along with a corresponding determination of a suitable antibiotic. Such a panel is important in at least two respects. Firstly, the number of tests is significantly reduced, compared to species-level test panels. For example, there are well over 100 possible sources of bacterial or fungal infections, and testing for each and every one would be an arduous and complicated task, making a rapid diagnosis and targeted treatment difficult. Secondly, the degree of confidence with each hierarchical level in the panel tree is increased, which could very possibly impact treatment decisions on a real-time basis. This approach, in effect, has a built-in control that improves the confidence interval.

Figure 10B:
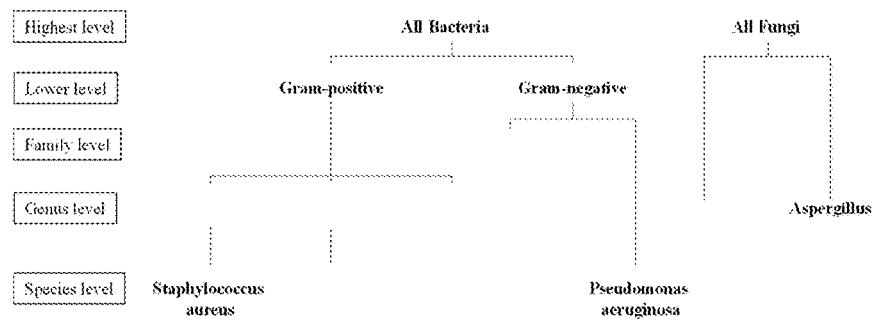
Figure 10C:
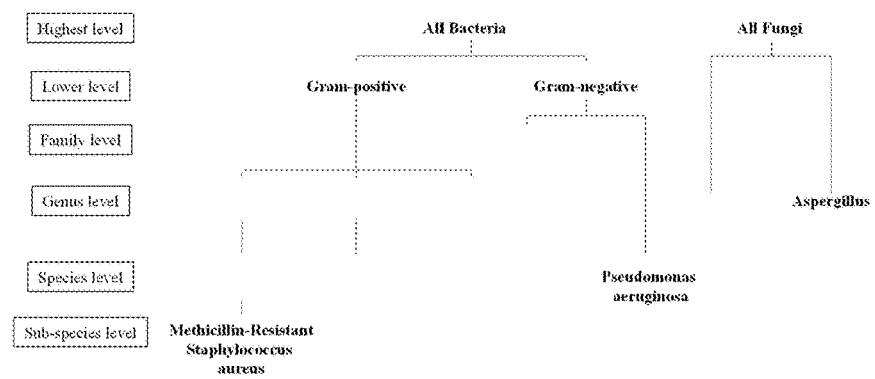

Three additional example panels are presented in FIGS. 10(*a*) through (c). The panel shown in FIG. 10(*a*) provides the following information: an indication of the kingdom classification (bacterial or fungal) of the pathogen, the Gram status of a bacteria, and further identification of selected genus and/or species levels. As noted above, identification of pathogens at a family and/or genus level may assist in decision making for antimicrobial drug selection and further testing as necessary. In this example panel, identification of selected pathogens at a species level provides the physician with specific information that is relevant to de-escalation of antimicrobial treatment, and information that can warrant further testing. For example, the identification of *S. aureus* at the species level could indicate to the physician that further testing for MRSA is warranted. Also, for example, the identification of *S. pneumoniae* at species level could alarm the physician to increasing ampicillin-resistant strains of *S. pneumoniae*. Furthermore, the identification of *P. aeruginosa* at species level could support a decision to alter the antimicrobial therapy to a more targeted, narrow-spectrum antimicrobial drug that is more selective for *P. aeruginosa*. Similarly, identification of *Aspergillus* can assist decision-making for more appropriate and narrow-spectrum treatment, while other fungi are generally sensitive to wider spectrum antimycotic agents.

In the panel shown in FIG. 10(*b*), pathogen Information is provided at the family, genus and/or species level in a more selective manner that is correlated with the selection of narrow-spectrum and appropriately targeted antimicrobial therapy. This panel is formulated based on the assessment that other than *S. aureus*, similar antibiotics can be considered for other Gram-positive bacteria. As a result, the *S. aureus* species level test is sufficient to provide suitable information for de-escalation of antibiotic therapy if the pathogen is found to be Gram-positive. Furthermore, if *S. aureus* is identified, the physician may request a test known for the mecA gene in order to determine whether or not the pathogen is MRSA. As noted above, the detection and identification for the panels shown in FIGS. 10(*a*) and 10(*b*) may be performed by detecting specific nucleic acid sequences within the pathogen's rRNA.

In the example panel shown in FIG. 10(*c*), the mecA gene a strain level test is provided for the detection of MRSA, which renders the species level test for *S. aureus* unnecessary. The test for the mecA gene may be performed based on the detection of genomic DNA. If the pathogen is found to be Gram-positive but not MRSA, then suitable other antibiotics which can cover all Gram-positive pathogens can be considered for treatment.

The aforementioned rapid sample pretreatment and rRNA-based testing protocols, when combined with a rapid de-escalation test panel as described above, enables the rapid and effective selection of appropriate narrow-spectrum antibiotics, or the appropriate initial selection of a suitable antibiotic, thereby dramatically reducing the number of tests, and the complexity of medical inquiry, required to enable a therapeutic decision. In particular, when aforementioned methods of sample pretreatment and rapid rRNA reverse transcription PCR are employed to perform tests according to such a rapid de-escalation panel, results are provided on a suitable timescale to affect patient outcomes, and with sufficient information to guide the de-escalation of antimicrobial therapy.

As noted above, the present embodiments do not require an enrichment step, and are capable of rapidly providing results that influence antimicrobial treatment. For example, in some embodiments, the time delay between initiating the pretreatment phase and the availability of the test results may be less than approximately 30 minutes. The rapid availability of the test results is important for enabling de-escalation of antimicrobial treatment, or prescribing an initial narrow-spectrum antibiotic, on a clinically relevant and effective timescale.

This is to be contrasted with existing molecular methods, which fail to find widespread clinical utility due to (1) the requirement for complex and time consuming manual sample preparation steps, (2) insufficient recovery of microbial cells when performing sample preparation based on direct, non-enriched samples, and (3) overly complex test results that fail to clearly inform appropriate decision making in antimicrobial stewardship.

The following examples are presented to enable those skilled in the art to understand and to practice embodiments of the present disclosure. They should not be considered as a limitation on the scope of the present embodiments, but merely as being illustrative and representative thereof.

EXAMPLES

In the following examples, Gram-negative bacteria cells were grown on LB agar plates and a single colony of cells was cultured in LB broth overnight at 37° C. Gram-positive bacterial and fungal cells were grown on tryptic soy agar with 5% sheep blood and a single colony of cells was cultured in tryptic soy broth overnight at 37° C. The cells were centrifuged at 7000 rpm for 5 min. The cell pellet was washed twice and re-suspended in 0.8 mM phosphate buffer pH 7.4, pre-filtered through a 0.2 µm filter.

The blood cell lysis reagent was used whenever blood sample pretreatment was required. The blood cell lysis reagent consisted of a mixture of saponin (84510, Sigma), sodium polyanethol sulfanate (SPS) (P2008, Sigma) and poly(propylene glycol) (PPG) MW 2000 (202339, Sigma). Saponin was dissolved in reagent grade water, filtered through 0.2 µm PES syringe filter and purified using Amicon Ultra-15 10K MW cut-off (Z706345, Sigma). SPS was dissolved in reagent water and filtered through 0.2 µm PES syringe filter. PPG MW 2000 (202339, Sigma) was used directly from the original bottle. In addition, Fluorinert™ FC-40 (F9755, Sigma) was added to serve as cushioning liquid.

Unless any variation is specified, the following example pretreatmet procedure which includes blood cell lysis step followed by 4 wash cycles was performed in experiments which required pretreatment of blood samples. 10 µL of Fluorinert™ was added to 2 mL siliconized microcentrifuge tubes (T3531, Sigma), followed by the addition of 500 µL of the blood cell lysis reagent. The blood cell lysis reagent consisted of 75 mg/mL saponin, 15 mg/mL SPS and 1% PPG. Sodium citrate-treated human whole blood (Bioreclemation Inc.) of 1 mL spiked with microbial cells was added to the tube containing the blood cell lysis reagent and the Fluorinert™, and mixed by inverting ten times and vortexing at low speeds for 10 sec. The final concentrations of the components in the mixture were 25 mg/mL saponin, 5 mg/mL SPS and 0.33% PPG. The tubes were centrifuged at 12,000 rpm for 1 min and 1.35 mL of the supernatant was removed, leaving 150 uL of the liquid supernatant, Fluorinert™ and the sedimented microbial I cells. The first wash cycles was performed by adding 1.35 mL of 0.8 mM phosphate buffer to the remaining liquid supernatant of 150 uL as described above, mixing by vortexing at low speed for 10 sec, centrifugation at 12,000 rpm for 1 min and removal of 1.35 mL of the supernatant, leaving 150 µL of the liquid supernatant, the Fluorinert™ and the sedimented microbial. The remaining wash cycles were performed by adding 0.75 mL of 0.8 mM phosphate buffer to the remaining liquid supernatant of 150 uL, mixing by vortexing at low speed for 10 sec, centrifugation at 12,000 rpm for 1 min and removal of 0.75 mL of the supernatant, leaving 150 µL of the liquid supernatant, the Fluorinert™ and the sedimented microbial. After the last wash, the sedimented microbial cells were re-suspended in the residual liquid, whose volume was in the range of 100 to 300 ul. Positive control samples are prepared by spiking 0.8 mM phosphate buffer pH 7.4 with the same concentration of respective microbial cells as the nominal concentration of the pretreated sample in respective experiments.

In examples that employed electrical cell lysis, the pretreated samples and the positive control samples were passed through an electrical chamber with steps of 10 µL/10 s and applying n=250 bipolar square pulses having duration of 50 µs and amplitude of 190 V. The electrical chamber had a dimension of 6.4×15×0.2 $mm^3$ and the iInlet and outlet ports were of restricted type.

In the following examples, real-time reverse transcription PCR (real-time RT-PCR) assay was performed to detect a specific target region in 16S or 18S rRNA of respective microbial cell types. The primers were designed by sequence alignment software (Bioedit, Ibis Biosciences, USA) and primer design software (Primera, National Institutes of Health). The cell lysate of the pretreated sample and the spiking control following the electrical lysis was subjected to real-time RT-PCR. In addition to the samples, the following negative controls were subjected to real-time RT-PCR:

pre-filtered phosphate buffer used for cell suspension (negative control; buffer), and unspiked blood subjected to the same pretreatment and electrical lysis protocol as the spiked blood samples (negative control; blood).

Unless any variation was specified, RT-PGR reaction of 20 µL volume was prepared by mixing 5 µL of sample, 10 µL of Kapa 2G Robust Hotstart 2×PCR reaction mix (kk5515, KAPA Biosystems), 1.2 µL of reverse transcriptase (GoScript, A5004 Promega), 1 µL of forward primer (10 µM), 1 µL of reverse primer (10 µM), 1 µl of SYTO-9 (100 nM, S34854, Invitrogen) and 0.8 µL of RNAase free water. One-step real time RT-PCR was performed by reverse transcription at 55° C. for 5 min, inactivation of reverse transcription at 95° C. for 2 min, followed by 35 cycles of cDNA amplification (denaturation at 95° C. for 3 sec, annealing at respective temperature for 3 sec, and extension at 72° C. for 3 sec) in Eco Real Time PCR system (illumine) using a double stranded DNA binding fluorescent dye, SYTO-9.

Example 1: The Effect of Washing on the Reduction of the Quenching Effect of Lysed Blood Debris on Amplicon Detection by Fluorescent Signal The experiments presented in this example were performed to determine the effect of washing cycles of reducing the quenching effect of lysed blood debris on the fluorescent signal and enabling efficient real time RT-PCR assay, according to an example method of pretreatment and amplification.

Figure 11:
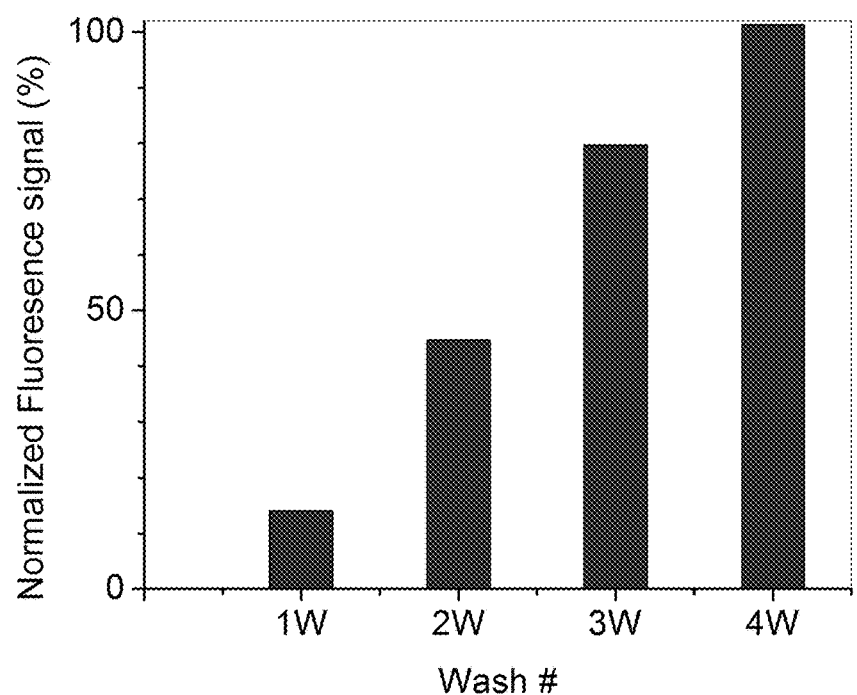
FIG. 11(a) shows the fluorescence signals of the amplicons in the supernatant of each wash cycles, illustrating the quenching effect of lysed blood debris and how wash cycles can be employed to alleviate quenching.
FIGS. 11(b) and (c) show the fluorescence signal versus PCR cycle number measured during real-time reverse transcription PCR (real time RT-PCR) assays of the cell lysates in the supernatants of a sample pretreatment procedure in which wash cycles are employed without centrifugation.
FIG. 11(d) shows the fluorescence signal versus PCR cycle number measured during real-time RT-PCR assays for cell lysates in the supernatants of wash cycles using an example sample pretreatment procedure, illustrating the dependence of the assay signal on the number of wash steps and electrical treatment.
Figure 11:
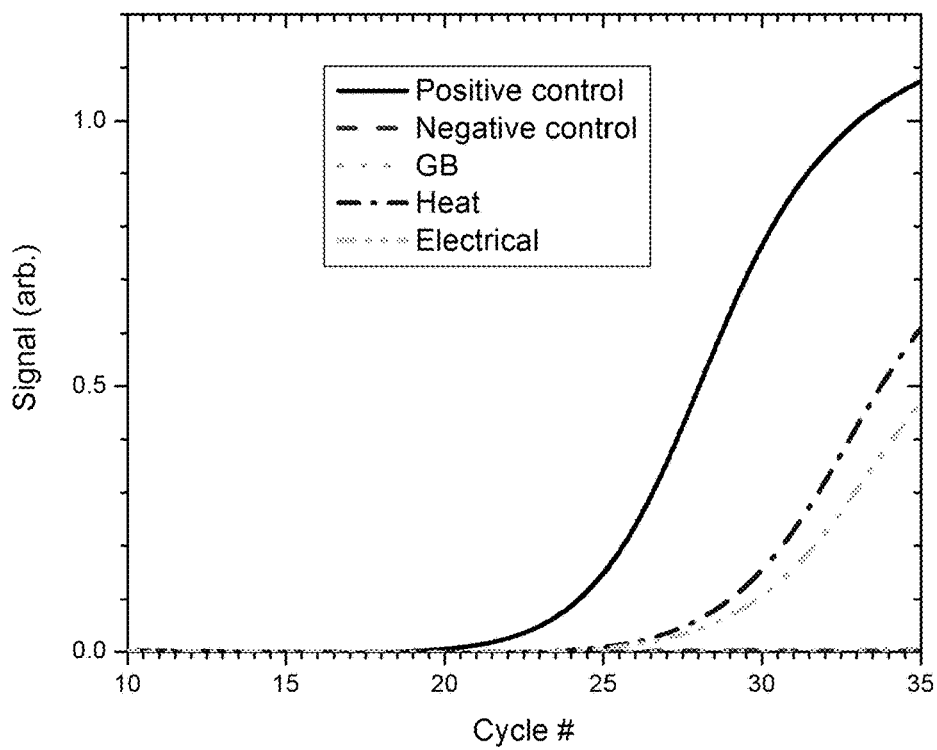
Figure 11:
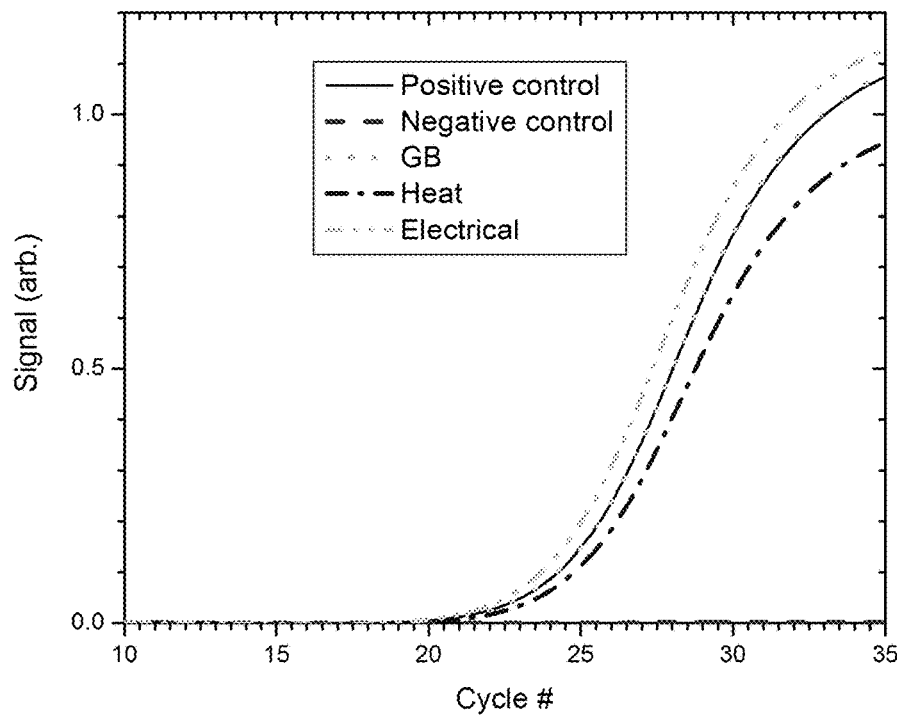
Figure 11:
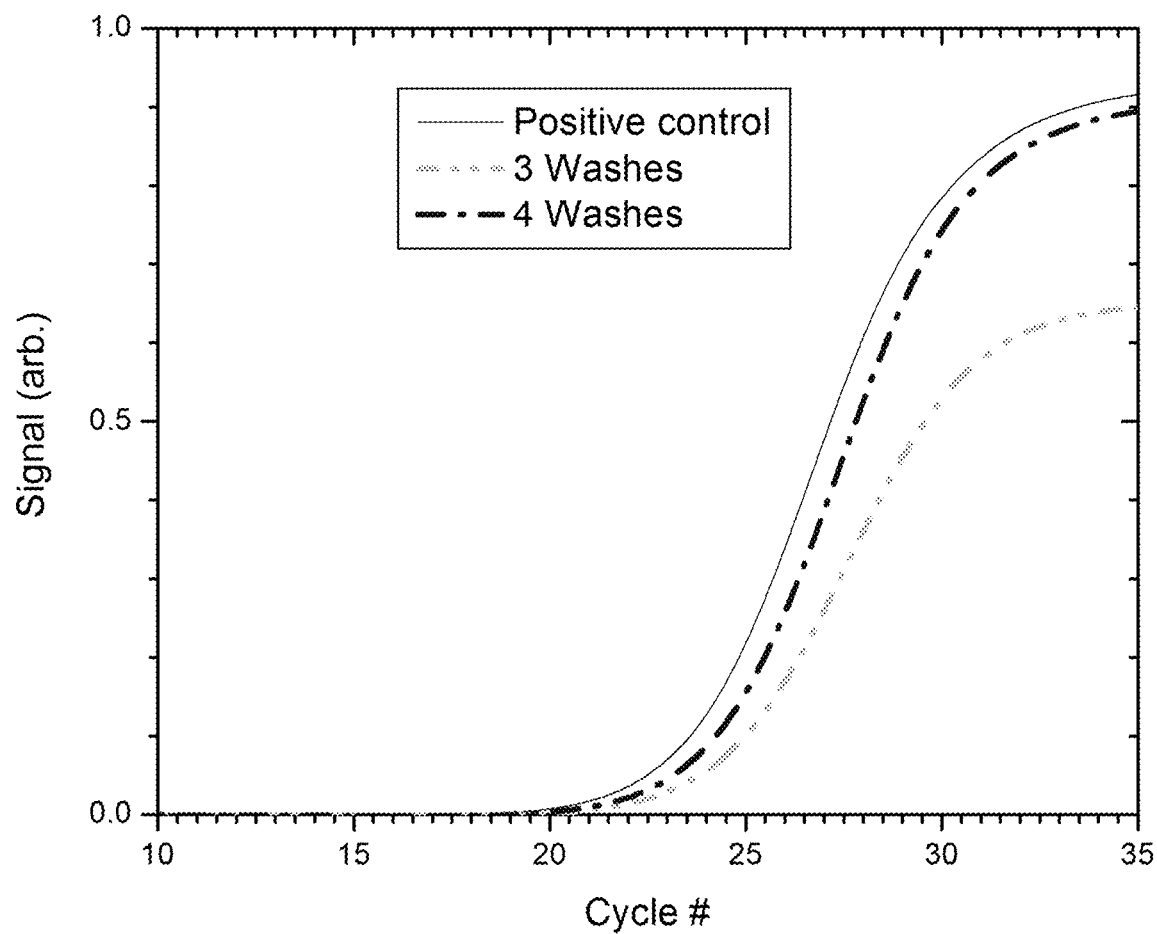

A suspension of 2000 CFU/mL Pseudomonas aeruginosa cells in 0.8 mM phosphate buffer with pH 7.4 was electrically lysed. The lysate was subjected to real time RT-PCR to prepare sufficient volume of amplicons for the experiment in this example. The forward and reverse primers used for RT-PCR were GGGCAGTAAGTTAATACCTTGC (SEQ. ID. 25) and TCTACGCATTTCACCGCTACAC (SEQ. ID. 26), respectively. The 16S rRNA gene fragment of 251 bases pair at a conserved region of *P. aeruginosa* (nucleotides 438 to 689 using *P. aeruginosa* D377P as a reference) was amplified. Human whole blood, which had been drawn into a collection tube with sodium citrate anticoagulant were subjected to the example sample pretreatment procedure described above with four wash cycles as described above (involving centrifugation). At the end of each wash cycle the removed supernatant was stored. A 5 µL volume of amplicon, prepared as described above, was added to 5 µL of the stored supernatant of each wash cycle. The fluorescence signal was read in Illumina machine. The signals were normalized to the signal of amplicons added to the clean phosphate buffer. The results of three different runs were presented in FIG. 11(*a*). As it is observed, the fluorescence quenching effects of the debris are significant up to 3 times washing, which corresponds to a 500 fold dilution.

Example 2: The Effect of Dilution-Based Wash Steps and Microbial Cell Lysis Method on Molecular Assays The experiments presented in this example were performed to demonstrate how number of wash steps and microbial cell lysis method affect the inhibitory effects of the lysed blood debris on the downstream molecular assays.

*Pseudomonas aeruginosa* cells were used and the cell suspension was prepared as described above. Human whole blood was subjected to the sample pretreatment procedure as described above with the following exceptions. The wash cycles were performed by adding the respective volume of 0.8 mM phosphate buffer to the remaining liquid supernatant of 150 uL and mixing by inverting 10 times, without vortexing or centrifugation. Thus, the samples are simply the serial dilutions of the originally lysed blood. The dilution-based wash cycles were performed five times instead of four times as per the example sample pretreatment procedure described above that employed centrifugation when washing. The removed supernatant of each wash cycle was split into 3 aliquots and spiked with *P. aeruginosa* cells. Each aliquot of 75 µL included nominal 30 microbial cells. One aliquot was electrically lysed and one aliquot was heat lysed by heating the suspension at 95° C. for 10 minutes. The third aliquot was subjected to mechanical lysis using glass beads (GB). To perform GB lysis, an equal volume of glass beads (<106 µm, G4649 Sigma) was added to 75 µL of cell suspension and mechanically lysed by vortexing at a high speed for 2 minutes. The GB cell lysate was centrifuged at 14,000 rpm for 1 minute to separate the beads and the supernatant was collected for the assay.

All lysates of 5 µL each containing the equivalent of 2 lysed microbial cells were assayed with real-time RT-PCR alongside negative control (buffer) and positive control (buffer spiked with microbial cells and electrically lysed). The forward and reverse primers used for RT-PCR were GGGCAGTAAGTTAATACCTTGC (SEQ. ID. 25) and TCTACGCATTTCACCGCTACAC (SEQ. ID. 26), respectively. The 16S rRNA gene fragment of 251 bases pair at a conserved region of *P. aeruginosa* (nucleotides 438 to 689 using *P. aeruginose* D77P as a reference) was amplified. The resulting signal versus real time PCR cycle # plots are presented in FIG. 11(*b*) for lysates of the fourth wash cycle and FIG. 11(*c*) for lysates of the fifth wash cycle. As it is observed in FIG. 11 (*b*), electrical and heat lysis greatly reduce the inhibitory effects of blood debris present in the supernatant of fourth wash cycle. However, as it is observed in FIG. 11(*c*), in the absence of centrifugation, a dilution equivalent to five wash cycles is required to eliminate the inhibitory effect of blood debris on the performance of RT-PCR assay when using the reagents and conditions similar to the present experiments.

Example 3: The Effect of Washing During the Example Sample Pretreatment Procedure on Reducing Inhibitory Effects of Lysed Blood Debris on Molecular Assays The experiments presented in this example were performed to demonstrate how washing cycles and electrical treatment reduces the inhibitory effects of the lysed blood debris on the downstream molecular assays. The dependence of a typical RT-PCR assay on the number of washing cycles during the example sample pretreatment was tested.

*Pseudomonas aeruginosa* cells were used and the cell suspension was prepared as described above.

Human whole blood was subjected to the example sample pretreatment procedure with four wash cycles as described above. The removed supernatants of third and fourth wash cycles were spiked with *P. aeruginosa* cells and subjected to electrical lysis. Each wash cycle supernatant aliquot of 75 µL included nominal 30 microbial cells. All lysates of 5 µL each containing the equivalent of 2 lysed microbial cells were assayed with real-time RT-PCR alongside positive control (buffer spiked with microbial cells and electrically lysed). The forward and reverse primers used for RT-PCR were GGGCAGTAAGTTAATACCTTGC (SEQ. ID. 25)

and TCTACGCATTTCACCGCTACAC (SEQ. ID. 26), respectively. The 16S rRNA gene fragment of 251 bases pair at a conserved region of *P. aeruginosa* (nucleotides 438 to 689 using *P. aeruginosa* D77P as a reference) was amplified.

The resulting signal versus cycle # plots is presented in FIG. 11(d). As it is observed, by following the example sample pretreatment wash steps described above, electrical treatment greatly reduces the inhibitory effects of blood debris. While the Ct value in the case of GB lysis was above 35 cycles, the corresponding Ct for electrical lysis was 25 cycles. In other words, the effects of electrical treatment in reducing the inhibitory effects of blood lysis debris, is equivalent to diluting inhibitors by a factor of 13. Moreover, in the case of the RT-PCR reagents used in the present tests, 4 washes are sufficient for eliminating the inhibitory effects of blood debris.

Example 4: Dependence of Detection Efficiency on the Blood Lysis Reagent Composition and Pretreatment Vessel Interior Surface The experiments presented in the following examples were performed to demonstrate the efficiency by which the microbial cells in a whole blood sample are recovered into the pretreated sample and that molecular assay inhibitory compounds are removed or inactivated. As noted above, such methods may be applicable for downstream reagentless microbial cell lysis followed by a nucleic acid assay without requiring additional steps of nucleic acid extraction/purification and/or medium balance. The dependence of microbial cell recovery on blood cell lysis reagent composition, volume of cushioning liquid and interior surface property of the sample pretreatment vessel were verified.

In these experiments, the viability of the recovered microbial cells may not be of concern, which is in contrast to cases when microbial cells are intended for subsequent growth (such as in the disclosures of Dorn referenced above). Instead, it may be sufficient that the blood cell lysis reagent does not substantially damage the microbial cells, to the extent of releasing nucleic acids and other macromolecules of interest, and avoids the introduction of nucleic acid assay inhibitory agents in the pretreated sample. Accordingly, the blood cell lysis reagent composition may be selected such that it is appropriate for wide range of microorganisms, in particular Gram-negative bacteria that are less tolerant of strong blood cell lysis agents. In order to demonstrate the capability of the method for the preparation of such less tolerant bacteria, the following examples were performed with *Pseudomonas aeruginosa* as the test organism.

*P. aeruginosa* cells were cultured and the cell suspension was prepared as described above. 10 µL of Fluorinert™ was added to 2 mL siliconized microcentrifuge tubes, followed by the addition of 500 µL of the blood cell lysis reagent. Despite any variation is specified, human whole blood collected in BD vacutainer with sodium citrate (BD366415) is used. The blood spiked with *P. aeruginosa* in 1 mL volume at 600 CFU/mL was added to the tube containing the blood cell lysis reagent and the Fluorinert™ and mixed by inverting 10 times and vortexing at low speeds for 10 sec. The sample pretreatment was performed as described above. After the last wash, most of the supernatant was removed and the sedimented cells were re-suspended in 300 µL of 0.8 mM phosphate buffer pH 7.4. The resulting pretreated sample contained a nominal cell number of 600. A 60 µL volume of the pretreated samples and the positive control were lysed by electrical lysis as described above. 5 µL of the cell lysate, containing the equivalent of 10 lysed microbial cells, and the negative control were assayed with real-time RT-PCR. The forward and reverse primers used for RT-PCR were GGGCAGTAAGTTAATACCTTGC (SEQ. ID. 25) and TCTACGCATTTCACCGCTACAC (SEQ. ID. 26), respectively. The 16S rRNA gene fragment of 251 bases pair at a conserved region of *P. aeruginosa* (nucleotides 438 to 689 using *Pseudomonas aeruginosa* 077P as a reference) was amplified.

Blood cell lysis reagent with varying concentrations of saponin and SPS, and varying volumes of Fluorinert™ were tested to verify the significance of each component in the pretreatment mixture. Then, using the optimized composition of the pretreatment mixture, bacteria recovery from pretreatment vessels with or without interior surface treatment was investigated.

Figure 12:
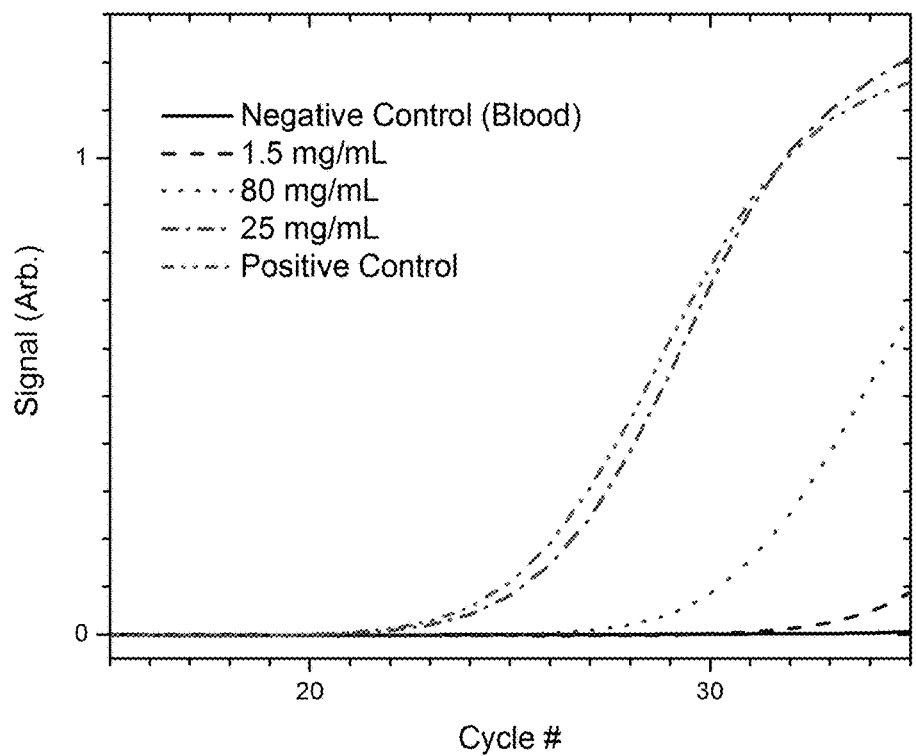
FIGS. 12(a) and (b) show the fluorescence signal versus PCR cycle number measured during real-time PCR assays, illustrating the dependence of the assay signal on (a) the concentration of saponin, and (b) the concentration of sodium polyanetholesulfonate (SPS).
Figure 12:
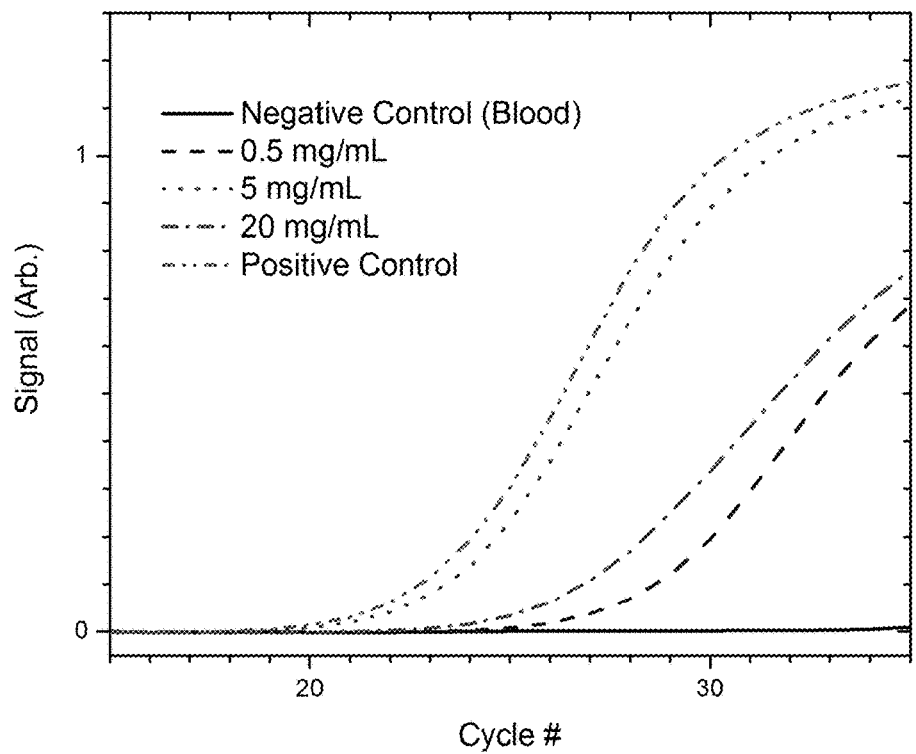

Example 4.1: Variation in Concentrations of Saponin Concentrations on Real-Time RT-PCR Assay Signal Human whole blood of 1 mL, spiked to 600 CFU/mL *P. aeruginosa* was added to 0.5 mL of the pretreatment mixture containing 10 µL of Fluorinert™ FC-40, 4.5 to 240 mg/mL saponin, 15 mg/mL SPS and 1% PPG, in a 2 mL siliconized microcentrifuge tube. The final concentrations of the components in the mixture were 1.5 to 80 mg/mL saponin, 5 mg/mL SPS and 0.33% PPG. The sample pretreatment procedure was performed and the pretreated samples and positive controls were electrically lysed. The real time RT-PCR assay signal of the bacteria in the pretreated sample recovered from the whole blood after the sample pretreatment is presented in FIG. 12(a). It appears that a final concentration of saponin of approximately 25 mg/mL is the most effective concentration for the present experimental conditions.

Example 4.2: Variation in Concentrations of SPS on Real-Time RT-PCR Assay Signal Human whole blood of 1 mL, spiked at 600 CFU/mL *P. aeruginosa* was added to 0.5 mL of the pretreatment mixture containing 10 µL of Fluorinert™ FC-40, 75 mg/mL saponin, SPS in the range of 0.5-20 mg/mL and 1% PPG, in 2 mL siliconized microcentrifuge tube. The final concentrations of the components in the mixture were 25 mg/mL saponin, 0.5 to 20 mg/mL SPS and 0.33% PPG The real time RT-PCR assay signal of the bacteria in the pretreated sample recovered from the whole blood after the sample pretreatment is presented in FIG. 12(b). It appears that a final concentration of SPS of approximately 5 mg/mL is the most effective concentration for the present experimental conditions.

Example 4.3: Variation in Type of Anticoagulant Used for Blood and the Pretreatment Mixture Composition Adjustment on Real-Time RT-PCR Assay Signal Human whole blood, which had been drawn into BD Vacutainer collection tubes with different anticoagulants. The collection tubes used were supplied with buffered sodium citrate (BD366415, normally used for coagulation testing), $K_2$ EDTA (BD367863, normally used for hematology testing), sodium heparin (BD367871, normally used for chemistry testing) and SPS containing 1.7 mL of 0.35% SPS and 0.85% sodium chloride (BD364960, specialty tubes normally used for blood culture specimen collection). The standard volume of blood specified by the manufacturer was drawn into each tube. Human whole blood collected in citrate, EDTA and Heparin tubes of 1 mL each, spiked at 600 CFU/mL *P. aeruginosa* was added to 0.5 mL of the pretreatment mixture containing 10 μL of Fluorinert™ FC-40, 75 mg/mL saponin, 15 mg/mL SPS and 1% PPG, in 2 mL (T-3531, Sigma) siliconized microcentrifuge tubes. The final concentrations of the components in the mixture were 25 mg/mL saponin, 5 mg/mL SPS and 0.33% PPG. For the blood collected in SPS tube, due to the presence of additional SPS in the anticoagulant solution in the tube, the pretreatment mixture was adjusted as 0.5 mL of the mixture containing 10 μL of Fluorinert™ FC-40, 112.5 mg/mL saponin, 7.5 mg/mL SPS and 1% PPG.

Figure 13:
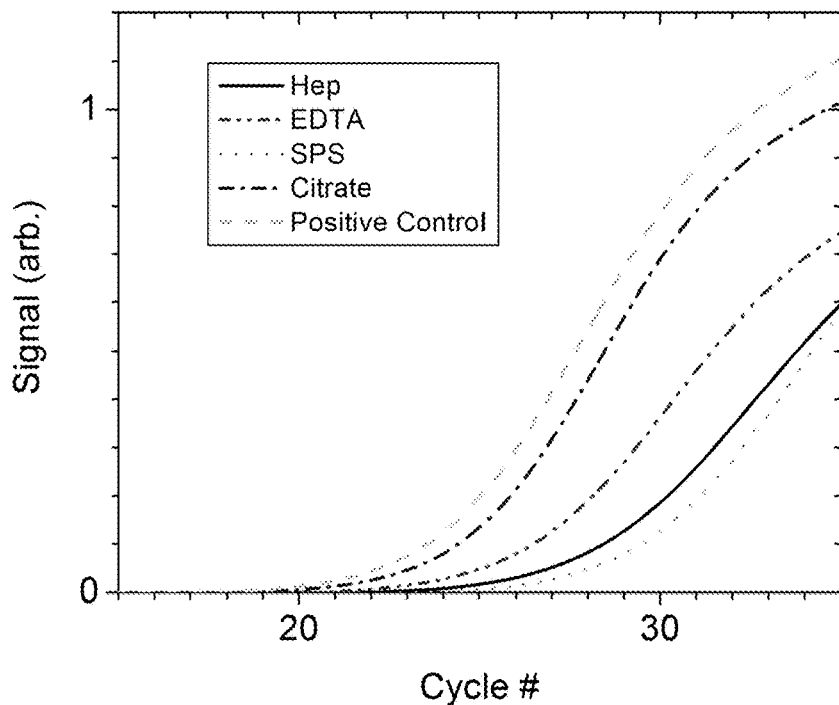
FIG. 13 shows the fluorescence signal versus PCR cycle number measured during real-time PCR assays, illustrating the recovery of microbial cells from human whole blood with different types of anticoagulants.

The pretreatment procedure was performed and the samples were electrically lysed. The real time RT-PCR assay signal of the bacteria in the pretreated sample recovered from the whole blood after the sample pretreatment is presented in FIG. 13. It was demonstrated that microbial cells were recovered from human whole blood despite the difference in the types of coagulants used.

Example 4.4: Variation in Volumes of Fluorinert™ on Real-Time RT-PCR Assay Signal Human whole blood of 1 mL, spiked at 600 CFU/mL *P. aeruginosa* was added to 0.5 mL of the pretreatment mixture containing different volumes of Fluorinert™ FC-40, 75 mg/mL saponin, 15 mg/mL SPS and 1% PPG. In addition the effect of variation in Fluorinert™ volume was tested in 2 different siliconized microcentrifuge tubes with different tube bottom geometry; 2 mL tubes (T-3531, Sigma) and 1.7 mL tubes (T-3406, Sigma). The final concentrations of the components in the mixture were 25 mg/mL saponin, 5 mg/mL SPS and 0.33% PPG. The pretreatment procedure was performed and the samples were electrically lysed. The real time RT-PCR assay signal of the bacteria in the pretreated sample recovered from the whole blood after the sample pretreatment is presented in FIGS. 14(*a*) and (*b*), where (a) shows the assay signal for the 2 ml tubes, and (b) shows the assay signal for the 1.7 ml tubes. It was demonstrated that for the present experimental condition, the volume of Fluorinert™ should be more than approximately 2.5 μL and less than approximately 100 μL for both types of tubes.

Figure 15:
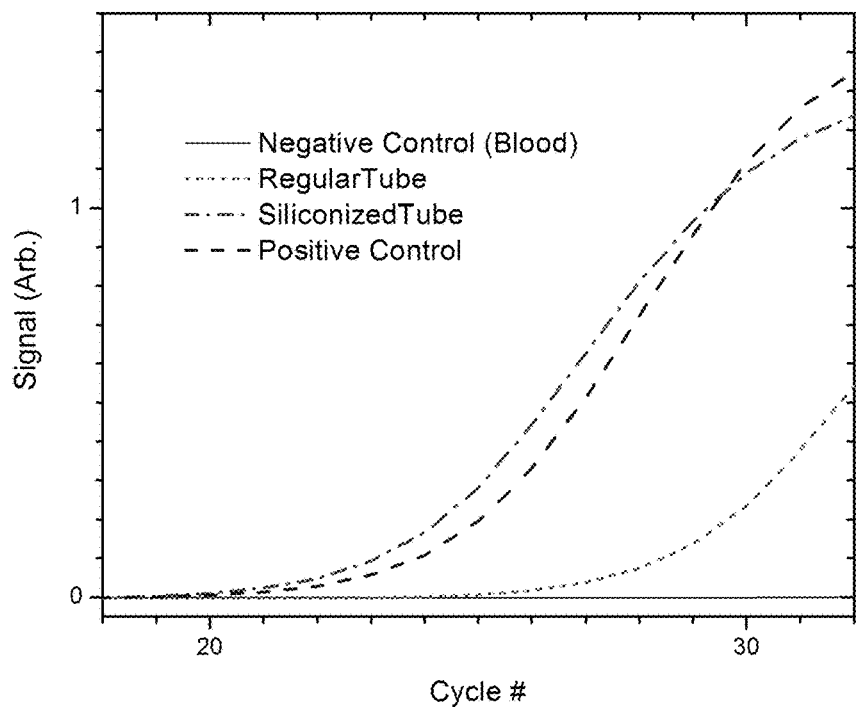
FIG. 15 shows the fluorescence signal versus PCR cycle number measured during real-time RT-PCR assays, illustrating the dependence of the assay signal on the pretreatment vessel surfaces.

Example 4.5: Variation in Pretreatment Vessel Interior Surface Property on Real-Time RT-PCR Assay Signal Human whole blood of 1 mL, spiked at 600 CFU/mL *P. aeruginosa* was added to 0.5 mL of the pretreatment mixture containing 10 μL of Fluorinert™ FC-40, 75 mg/mL saponin, 15 mg/mL SPS and 1% PPG, in 2 mL microcentrifuge tube with or without interior surface treatment. In one group, regular 2 mL polypropylene microcentrifuge tubes (B71420, Bioplastics) were used. In the other group, 2 mL siliconized microcentrifuge tubes (T-3631, Sigma) were used. The final concentrations of the components in the mixture were 25 mg/mL saponin, 5 mg/mL SPS and 0.33% PPG. The real time RT-PCR assay signal versus cycle number of the bacteria in the pretreated sample recovered from whole blood after sample pretreatment is presented in FIG. 15. The $C_T$ value for regular tube is about 4 cycles later than the case of siliconized tube, indicating more efficient cell recovery during the pretreatment process. Therefore, the siliconization of the interior surface may be employed for more efficient recovery of bacterial cells from the whole blood.

Example 4.6: Variation in Type of Blood Cell Lysing Reagent on Real-Time RT-PCR Assay Signal Human whole blood of 1 mL, spiked at 600 CFU/mL *P. aeruginosa* was added to the pretreatment mixture containing 10 μL of Fluorinert™ FC-40 in a 2 mL microcentrifuge tube. The pretreatment reagent used in this example were (a) 500 uL of saponin mixture containing 75 mg/mL saponin, 15 mg/mL SPS and 1% PPG and (b) 1 mL of 1% Triton X-100 in Sodium Carbonate buffer pH 10. After the centrifugation, following the cell lysis step, the supernatant was removed, leaving 150 uL of the liquid supernatant, Fluorinert™ and the sedimented microbial cells. Five washing cycles of pretreatment procedure were performed and the samples were electrically lysed. The real time RT-PCR assay signal of the bacteria in the treated sample recovered from the whole blood indicated that the Ct values of the two blood cell lysing reagents formulations were similar within 1 cycle.

Example 4.7: Variation in Type of Blood Cell Lysing Reagent on Real-Time RT-PCR Assay Signal Human whole blood of 1 mL, spiked at 600 CFU/mL *P. aeruginosa* was added to the pretreatment mixture containing 10 μL of Fluorinert™ FC-40 in a 2 mL microcentrifuge tube. The pretreatment reagent of 500 uL used in this example were (a) saponin mixture containing 75 mg/mL saponin, 15 mg/mL SPS and 1% PPG, (b) 1.5% Triton X-100 and 18.75 mg/mL SPS in Sodium Phosphate buffer pH 7.4, (c) 1.5% Triton X-100 and 22.5 mg/mL SPS in Sodium Phosphate buffer pH 7.4, (d) 4.5% Triton X-100 and 15 mg/mL SPS in Sodium Phosphate buffer pH 7.4 and (e) 3% Triton X-100 and 22.5 mg/mL SPS in Sodium Phosphate buffer pH 7.4, After the centrifugation, following the cell lysis step, the supernatant was removed, leaving 150 uL of the liquid supernatant, Fluorinert™ and the sedimented microbial cells. Five washing cycles of the pretreatment procedure were performed and the samples were electrically lysed. The real time RT-PCR assay signal of the bacteria in the treated sample recovered from the whole blood indicated that the Ct values of the blood cell lysing reagents were similar within 1 to 2 cycles.

Example 5: Detection Limit of Microorganisms Spiked in Human Whole Blood

The three examples presented in this section demonstrate the ability of the device to detect microbial cells in human whole blood with a detection limit in the range of 1-10 cells per mL for fungi, Gram-positive bacteria and Gram-negative bacteria.

Human whole blood (Bioreclemation Inc.) of 1 mL volume was spiked with the microbial cells specific to each example below and subjected to pretreatment and electrical lysis as described above. As a positive control, the same concentration of the microbial cells in 0.8 mM phosphate buffer was subjected to electrical lysis without pretreatment.

Human whole blood of 1 mL spiked with 300 and 30 CFU/mL of microbial cells was added to the tube containing blood cell lysis reagent and Fluorinert™, and the example sample pretreatment procedure described above was performed.

After the last wash, the supernatant was removed and the sedimented cells were re-suspended in 300 μL of 0.8 mM phosphate buffer pH 7.4 (resulting in a nominal concentration of $10^3$ and $10^2$ CFU/mL).

A 60 μL volume of the pretreated samples and the positive controls were subjected to electrical lysis. In each case, a cell lysate volume of 10 μL (nominally 10 and 1 cells respectively per sample) was subjected to amplification by RT-PCR.

In the following examples, RT-PCR reaction mixture of 25 μL volume was prepared by mixing 10 μL of sample, 12.5 μL of 2×PCR reaction mix (2G Robust HotStart, KAPA Biosystems), 1.3 μL of reverse transcriptase (GoScript, Promega), 0.6 μl of forward primer (10 μM) and 0.6 μL of reverse primer (10 μM). One-step real time RT-PCR was performed by reverse transcription at 55° C. for 5 min, inactivation of reverse transcription at 95° C. for 2 min, followed by 35 cycles of cDNA amplification (denaturation at 95° C. for 3 sec, annealing at 55° C. for 3 sec, and extension at 72° C. for 3 sec) and final extension at 72° C. for 1 min in Eco Real-Time PCR System (illumine). The resulting RT-PCR product of 15 μL was resolved by gel electrophoresis on 1% agarose gel in 0.5×TBE buffer and 0.5 μg/mL ethidium bromide at 150 volts for 30 min. The specific nucleotide sequences within the amplified region were detected using specific molecular beacon. RT-PCR product of 5 μL was mixed with 1 μL of the buffer containing 20 mM Tris-HCl pH 8, 10 mM KCl and 7 mM $MgCl_2$ as well as 1 μM of molecular beacon. The mixture was heated at 95° C. for 30 sec to denature the amplicon and the molecular beacon, followed by cooling to room temperature, allowing hybridization of the molecular beacon to the target sequence. The resulting mixture of 6 μL was transferred to a microwell and the fluorescence intensity of excitation at 492 nm and emission at 517 nm was measured using fluorescence microscopy (LumaScope, etaluma).

Example 5.1: Detection of Fungi Spiked in Human Whole Blood

Samples spiked with *C. albicans* were prepared and processed as described above for RT-PCR assay. The one-step RT-PCR protocol used UFF3 forward primer (5'-AAC-GAAAGTTAGGGGATCGAAG-3') (SEQ. ID. 15) and UFR3 reverse primer (5'-CTTTAAGTTTCAGCCTT-GCGA-3') (SEQ. ID. 16). The 18S rRNA gene fragment of 167 bases pair at a hypervariable region of all fungi species (nucleotides 940 to 1107 using *Candida albicans* AB013586 as a reference) was amplified.

Figure 16:
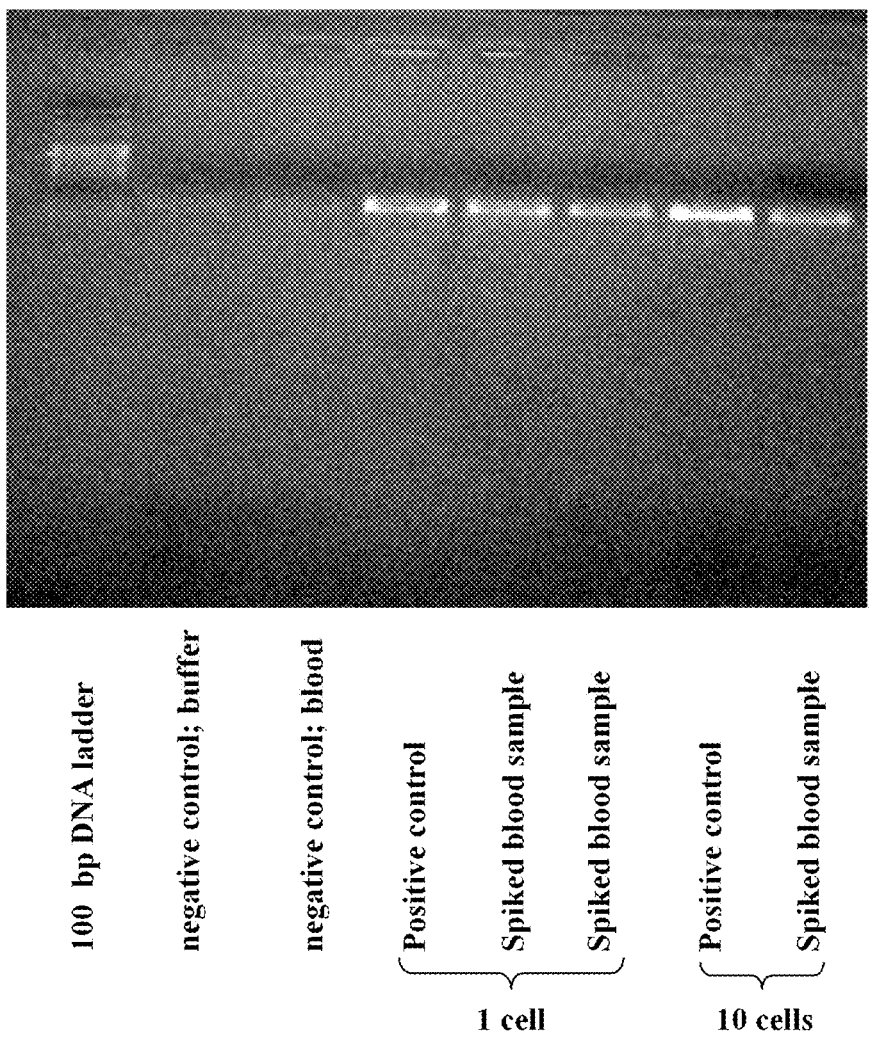
FIG. 16 demonstrates the detection limit of *Candida albicans* in blood samples. The RT-PCR amplified product of the 18S rRNA fragment of *C. albicans* was visualized after resolving on agarose gel electrophoresis, showing the detection of 1 and 10 *C. albicans* cells.

The resulting RT-PCR product of 15 μL was resolved by gel electrophoresis and the amplified region of 18S rRNA was observed in FIG. 16. This example demonstrates the detection of *C. albicans* fungal cells spiked in human whole blood with sensitivity in the range of 1-6 cells.

The specific nucleotide sequences within the amplified region were detected using the molecular beacon 6-FAM-5'-CCGAGCCGTAGTCTTAACCATAAACTATGCGCT-3'-DABCYL (SEQ. ID. 17) (nucleotides 977 to 997 using *Candida albicans* AB013586 as a reference), designed to detect all fungal pathogens. The detection signals of the positive controls and the spiked blood samples recovered from blood pretreatment are presented in FIG. 17. This example demonstrates the efficiency of molecular beacon method to detect *C. albicans* spiked in human whole blood with sensitivity in the range of 1-6 cells.

Example 5.2: Detection of Gram-Positive Bacteria Spiked in Human Whole Blood

Samples spiked with *S. pneumoniae* were prepared and processed as described above for RT-PCR assay. The one-step RT-PCR protocol used Ubea primer pair (UbeaF forward primer; 5'-GACAGGTGGTGCATGGTTGTC-3' (SEQ. ID. 18) and UbeaR reverse primer, 5'-ACGTCATC-CCCACCTTCCTC-3') (SEQ. ID. 19) and GP1 primer pair (GP1F forward primer; 5'-ATGCATAGCCGACCT-GAGAG-3' (SEQ. ID. 11) and GP1R reverse primer; 5'-AGTTAGCCGTSSCTTTCTG-3') (SEQ. ID. 12). The 16S rRNA gene fragment of 170 bases pair at a hypervariable region of all bacterial species (nucleotides 1035 to 1185 using *Streptococcus pneumonia* G54 as a reference) was amplified by universal bacterial Ubea primer pair and the 16S rRNA gene fragment of 230 base pairs at a hypervariable region of all Gram-positive bacterial species (nucleotide 290 to 520 using *Staphylococcus aureus* NR 037007 as reference) was amplified by Gram-positive specific GP1 primer pair.

Figure 18:
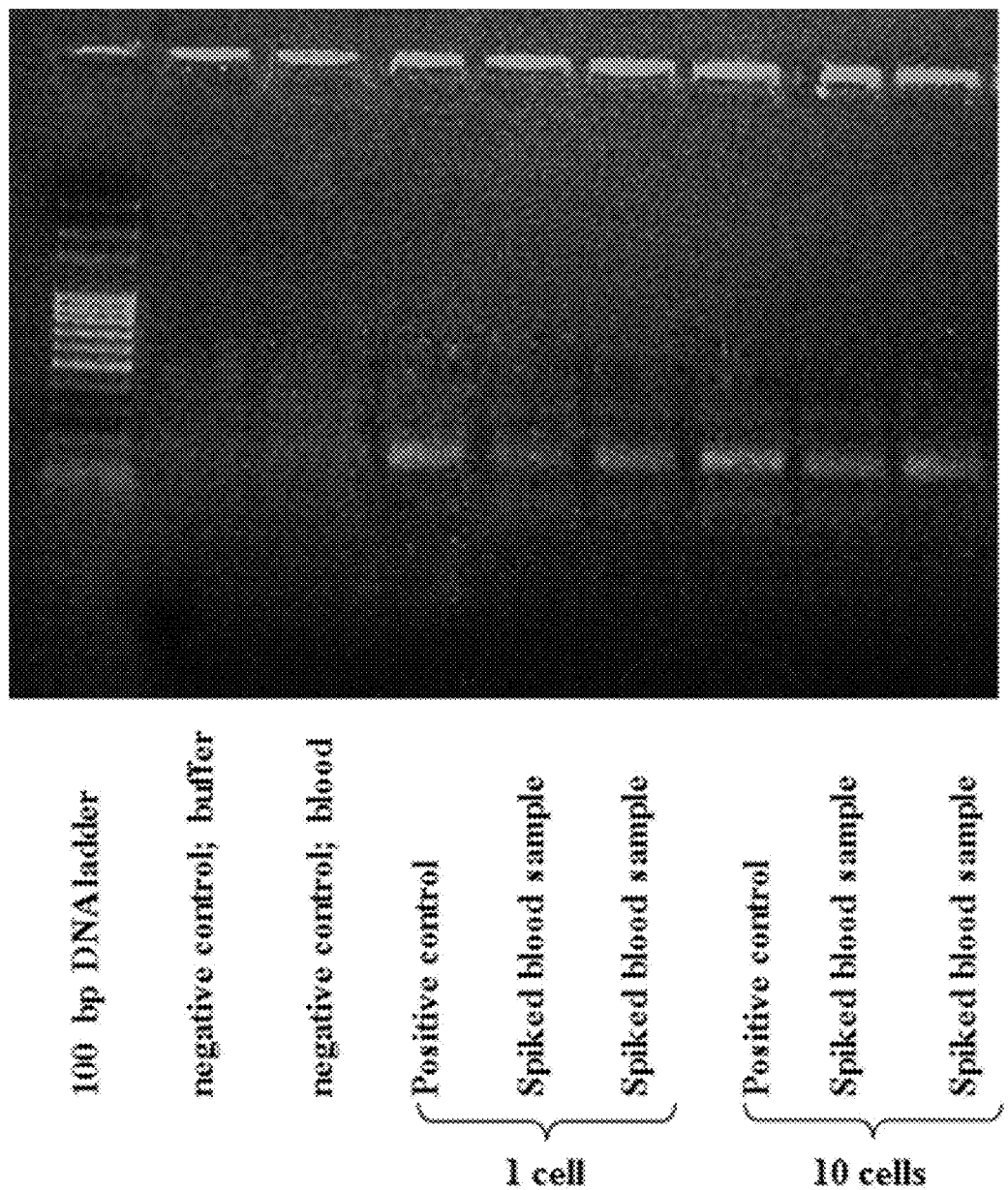
FIG. 18 demonstrates detection limit of *Streptococcus pneumoniae* in blood samples. The RT-PCR amplified product of the 16S rRNA fragment of *S. pneumoniae* was visualized after resolving on agarose gel electrophoresis, showing the detection of 1 and 10 *S. pneumoniae* cells.

The resulting amplified product using GP1 primer pair, targeting all Gram-positive bacterial species was resolved by gel electrophoresis and the amplified fragment of 16S rRNA was observed in FIG. 18. This example demonstrates the detection of Gram-positive *S. pneumoniae* bacteria in blood with sensitivity in the range of 1-6 cells.

The Gram-positive specific nucleotide sequences within the amplified product using Ubea universal bacterial primer pair, targeting all bacterial species were detected using the molecular beacon; 6-FAM-5'-CCGAGCTTAGTTGCCAT-CATTTAGTTGGGCACTCTAGCTCGG-3'-DABCYL (SEQ. ID. 20) (nucleotides 1113 to 1142 using *Streptococcus pneumonia* G54 as a reference) designed to detect all Gram-positive bacterial pathogens. The detection signals of the positive controls and the spiked blood samples recovered from blood pretreatment were presented in FIG. 19. This example demonstrates the efficiency of molecular beacon method to detect Gram-positive *S. pneumoniae* spiked in human whole blood with sensitivity in the range of 1-6 cells.

Example 5.3: Detection of Gram-Negative Bacteria Spiked in Human Whole Blood

Samples spiked with *E. coli* were prepared and processed as described above for RT-PCR assay. The one-step RT-PCR protocol used UB primer pair (UBF8 forward primer; 5'-CG-GCTAACTCCGTGCCAGCAG-3' (SEQ. ID. 12) and UBRs reverse primer; 5'-ATCTCTACGCATTTCACCGCTACAC-3') (SEQ. ID. 2) and GN1 primer pair (GN1F forward primer; 5'-GTTACCCGCAGAAGAAGCAC-3' (SEQ. ID. 13) and GN1R reverse primer; 5'-ACCTGAGCGTCA-GTCTTCGT-3' (SEQ. ID. 14) targeting all Gram-negative bacterial species. The 16S rRNA gene fragment of 203 base pairs at a hypervariable region of all bacterial species (nucleotides 504 to 707 using *Escherichia coli* O104:H4 str. 2011C-3493 as a reference) was amplified by universal bacterial UB primer pair and the 16S rRNA gene fragment of 278 bases pair in a hypervariable region of all Gram-negative bacterial species (nucleotide 475 to 753 using *Escherichia coli* NR 024570.1 as reference) was amplified by Gram-negative specific GN1 primer pair.

Figure 20:
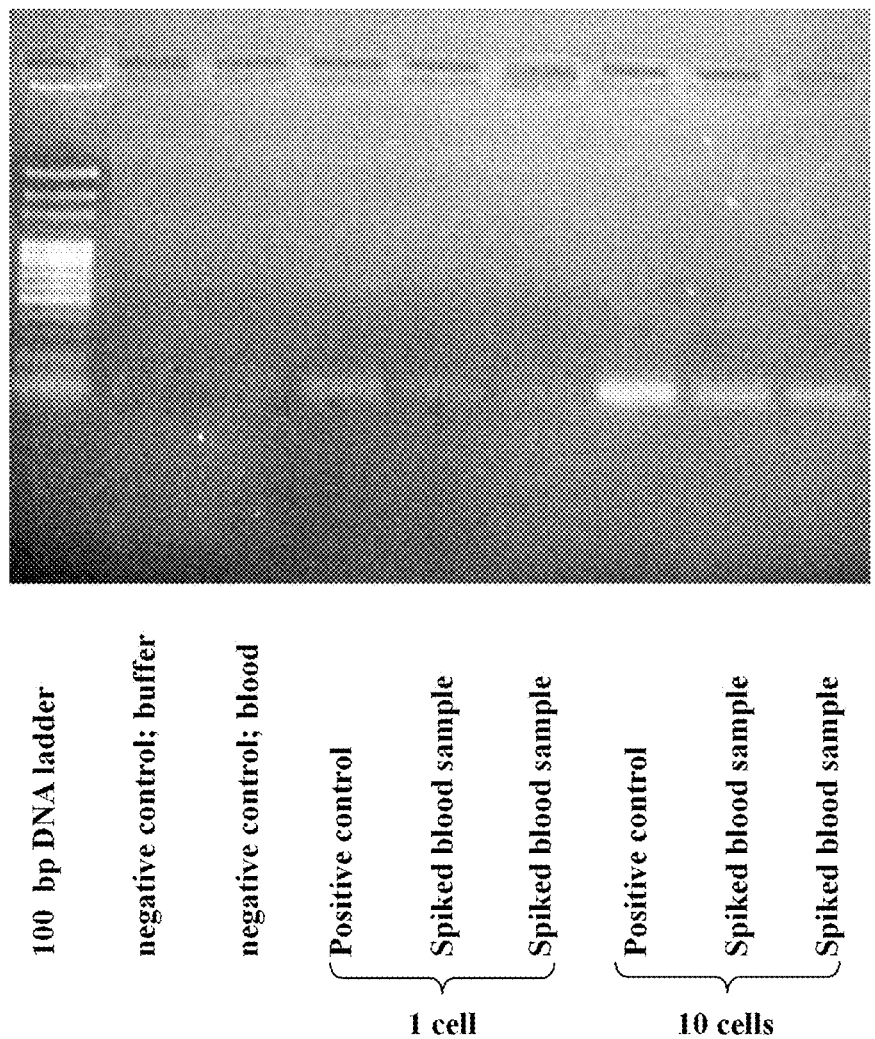
FIG. 20 demonstrates detection limit of *Escherichia coli* in blood samples. The RT-PCR amplified product of the 16S rRNA fragment of *E. coli* was visualized after resolving on agarose gel electrophoresis, showing the detection of 1 and 10 *E. coli* cells.

The resulting amplified product using GN1 primer pair, targeting all Gram-negative bacterial species was resolved by gel electrophoresis and the amplified fragment of 16S rRNA was observed in FIG. 20. This example demonstrates the detection of Gram-negative E. coli bacteria in blood with sensitivity in the range of 1-6 cells.

The Gram-positive specific nucleotide sequences within the amplified product using UB universal bacterial primer pair, targeting all bacterial species were detected using the molecular beacon; 6-FAM-5'-CCGAGCGGTGCAAGCGT-TAATCGGAATTACTGGGCGCTCGG-3'-DABCYL (SEQ. ID. 5) (nucleotides 541-569 using *Escherichia coli* O104:H4 str. 2011C-3493 as a reference) designed to detect all Gram-negative bacterial pathogens. The detection signals of the spiking controls and the spiked blood samples recovered from blood pretreatment were presented in FIG. 21. This example demonstrates the efficiency of molecular beacon method to detect Gram negative *E. coli* spiked in human whole blood with sensitivity in the range of 1-6 cells.

Example 6: Repeatability of Detection Method as Measured Using Real-Time RT-PCR This example demonstrates the repeatability of the detection of microbial cells in 1 mL of human whole blood sample within a total run-time of 30 minutes. Although the end goal is a multiplexed detection scheme, the present example is the detection of each species by individual RT-PCR assays.

Five different species each of Gram-positive, Gram-negative and fungal microbial cells described in FIG. 22, the representatives of the example panels in FIGS. 9 and 10, were tested. Sixty cells of each species were spiked into 1 mL of blood. The blood samples were then pre-treated to obtain 300 μL of pretreated samples in filter-sterilized 0.8 mM phosphate buffer and designated as spiked blood samples. Sixty cells of each species were added into 300 μL of filter-sterilized 0.8 mM phosphate buffer and used as respective positive controls. The blood of 1 mL volume without spiking with microbial cells also was pre-treated to obtain 300 μL of a pretreated sample in filter-sterilized 0.8 mM phosphate buffer and designated as a negative control (blood). Each sample and control of 70 μL was electrically lysed and RT-PCR assay was performed on 5.5 μL of each lysate, which is equivalent to detection at a single cell level. RT-PCR reaction of 20 μL volume was prepared by mixing 5.5 μL of sample, 10 μl of 2×PCR reaction mix (GoTaq Colourless, Promega), 1.5 μL of reverse transcriptase (GoScript, Promega), 0.5 μl of forward primer (10 μM), 0.5 μl of reverse primer (10 μM) and 2 μl of SYTO-9 (100 nM). One-step real-time RT-PCR was performed by reverse transcription at 55° C. for 5 min, inactivation of reverse transcription at 95° C. for 2 min, followed by 30 cycles of cDNA amplification at 95° C. for 3 sec, 59° C. for 3 sec, and 72° C. for 3 sec in Eco real time PCR system (Illumina) using a double stranded DNA binding fluorescent dye, SYTO-9. The primers used for RT-PCR to detect Gram-positive bacteria, Gram-negative bacteria and fungi are presented in FIG. 23.

The duration of sample pretreatment process was 6 minutes. The electrical lysis of samples or controls in steps of 10 μL/10 s took place in 1 minute. The RT-PCR assay with real time detection was under 20 minutes. Therefore, the total run-time for the detection of microbial cells in 1 mL of raw human whole blood was 27 minutes.

Figure 24:
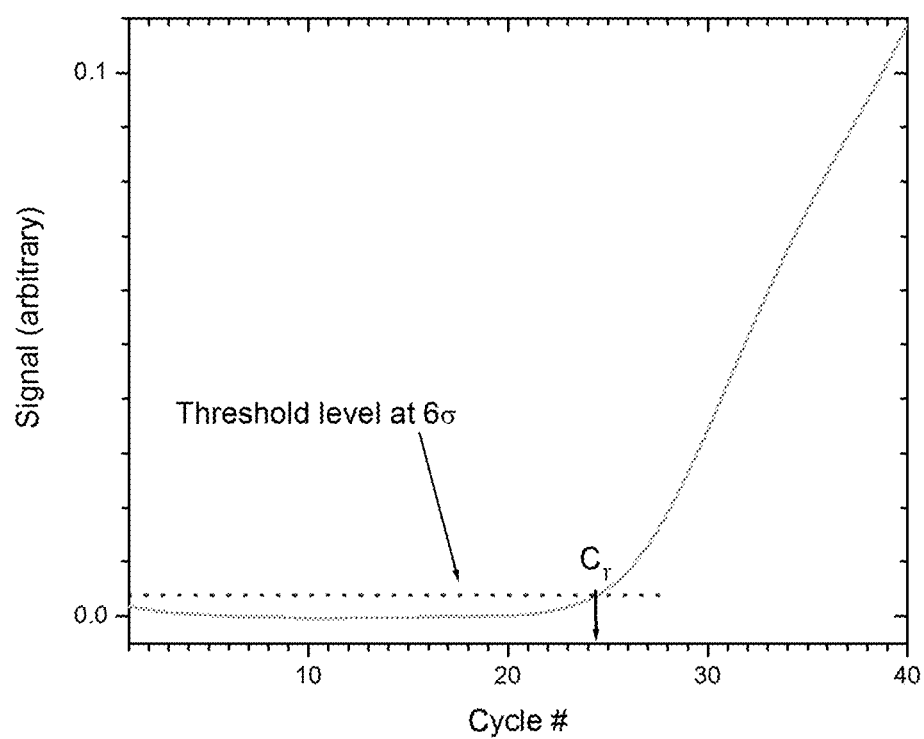
FIG. 24 shows the fluorescence signal measured during a typical real-time RT-PCR assay.

The detectability criterion was defined as the following. The RT-PCR fluorescence signal versus cycle number for the case of a single *Enterococcus faecalis* cell in human whole blood is presented in FIG. 24. The standard deviation of the signal over the first 10 cycles, where the signal is predominately background noise, is calculated and indicated as a large dashed line in FIG. 24. A threshold signal level is decided to be 6σ. The cycle number where the recorded signal exceeds the threshold level is defined as $C_T$. If the $C_T$ value of a sample differs by more than 5 cycles (a signal to noise ratio of over 32) from the $C_T$ value of the corresponding negative control blood sample running in parallel with the sample, the detection is considered to be unambiguous.

Example 6.1: Rapid Detection of Gram-Positive Bacteria in Raw Human Whole Blood Five pathogenic species were tested: EF (*Enterococcus faecalis*), SS (*Streptococcus sanguis*), SP (*Streptococcus pneumonia*), SA (*Staphylococcus aureus*), and SPy (*Streptococcus pyogenes*). Spiked blood samples, and positive and negative controls were prepared and subjected to electrical lysis as described above. The RT-PCR protocol used GPF8 forward primer; 5'-GCTCGTGTCGTGAGATGTTGGG-3' (SEQ. ID. 21) and GPR8 reverse primer, CAGGT-CATAAGGGGCATGATGAT-3' (SEQ. ID. 22). The 16S rRNA gene fragment of 151 base pairs at a hypervariable region of all Gram-positive bacterial species (nucleotides 1069 to 1220 using *Staphylococcus* sp. LS255 as a reference) was amplified.

Figure 25:
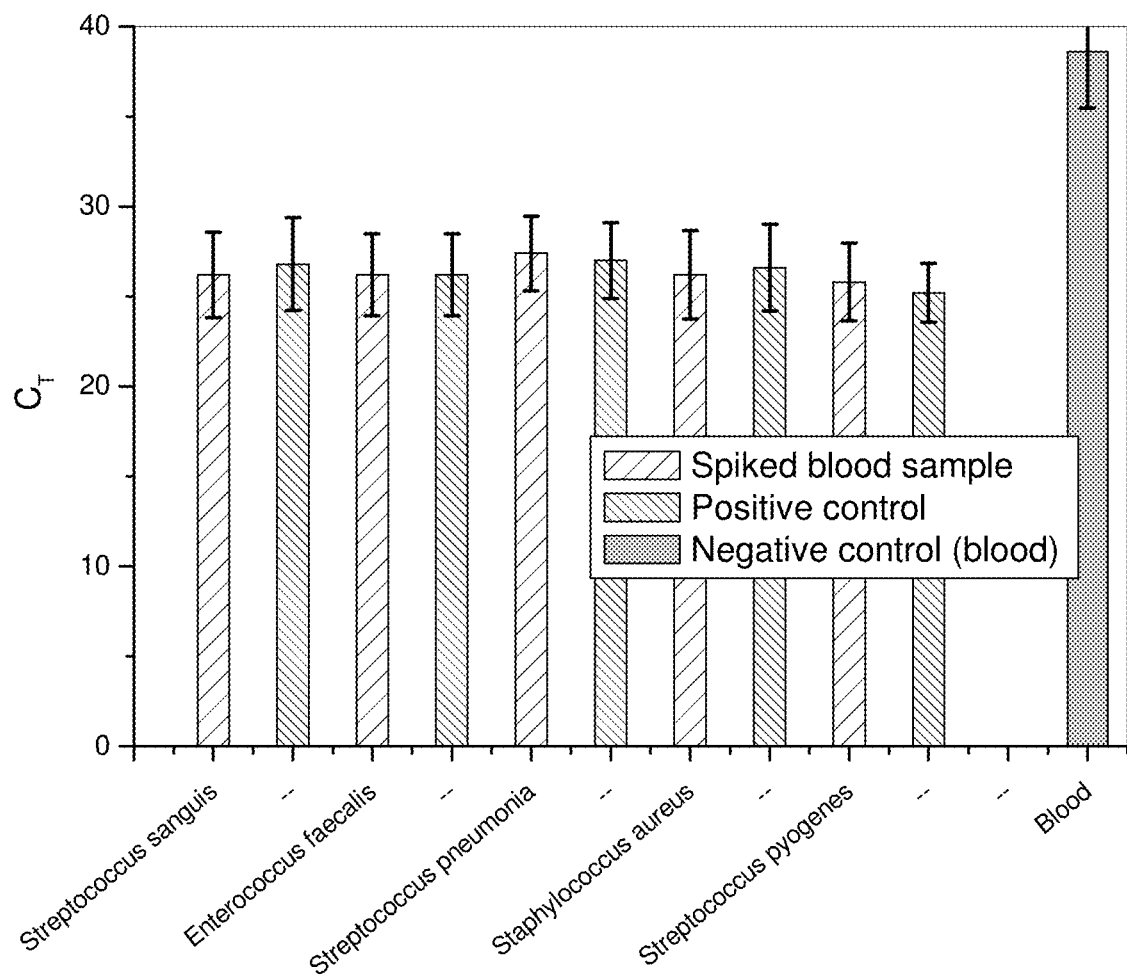
FIG. 25 shows the $C_T$ values for the real-time RT-PCR detection of a single cell of different Gram-positive bacterial species in blood samples.

The resulting $C_T$ values for different species over five independent runs are presented in FIG. 25. The detection limit criterion as described above was satisfied for all Gram-positive species.

Figure 26:
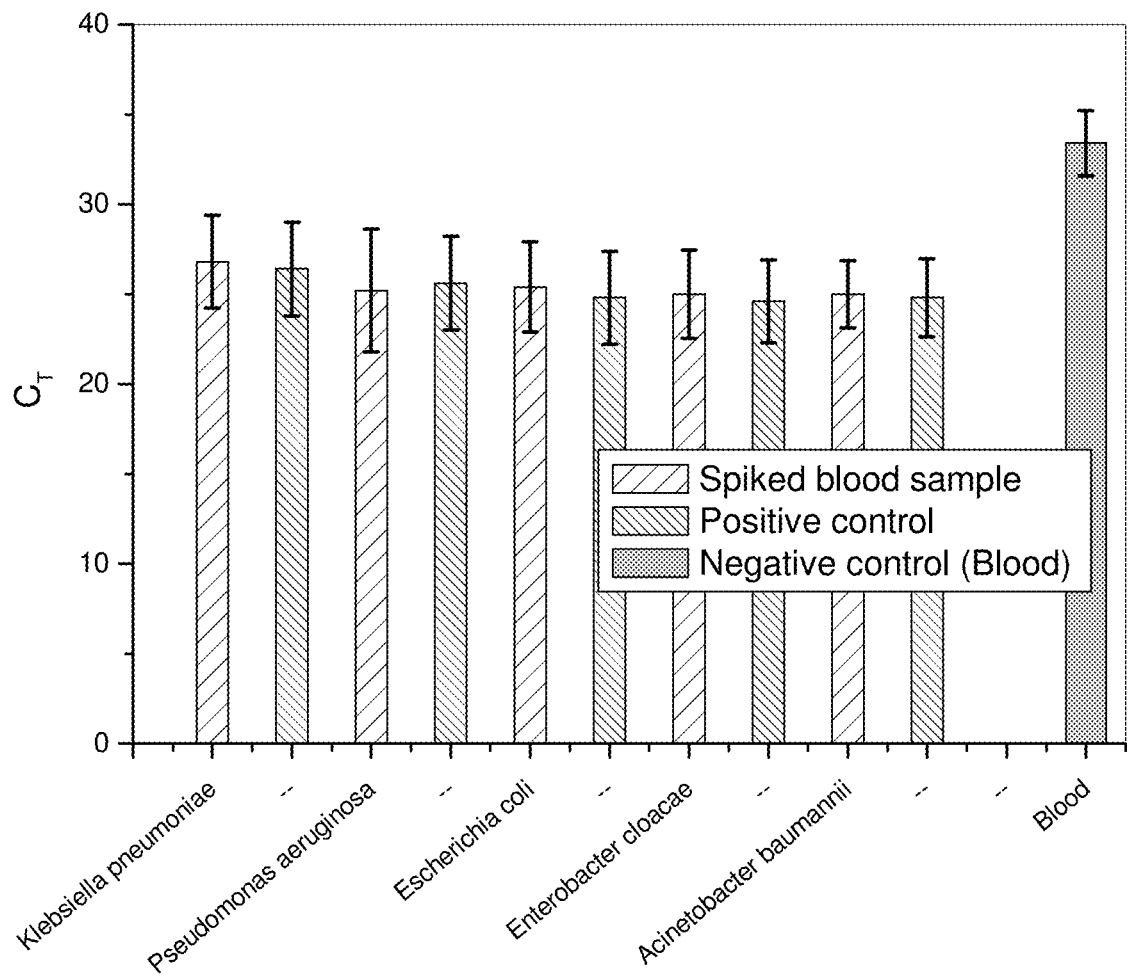
FIG. 26 shows the $C_T$ values for the real-time RT-PCR detection of a single cell of different Gram-negative bacterial species in blood samples.

Example 6.2: Rapid Detection of Gram-Negative Bacteria in Raw Human Whole Blood Five pathogenic species were tested: KP (*Klebsiella pneumoniae*), PA (*Pseudomonas aeruginosa*), EC (*Escherichia coli*), ECL (*Enterobacter cloacae*), and AB (*Acinetobacter baumannii*). Spiked blood samples, and positive and negative controls were prepared and subjected to electrical lysis as described above. The RT-PCR protocol used GNF8 forward primer; 5'-GTTACCCGCAGAAGAAGCACCG-3' (SEQ. ID. 23) and GNR8 reverse primer, 5'-ATGCAGTTC-CCAGGTTGAGCC-3' (SEQ. ID. 24). The 16S rRNA gene fragment of 151 base pairs at a hypervariable region of all Gram-negative bacterial species (nucleotides 484 to 635 using *Escherichia coli* la11 as a reference) was amplified. The resulting $C_T$ values for different species over five independent runs are presented in FIG. 26. The detection limit criterion as described above was satisfied for all Gram-negative species.

Example 6.3: Rapid Detection of Fungi in Raw Human Whole Blood

Figure 27:
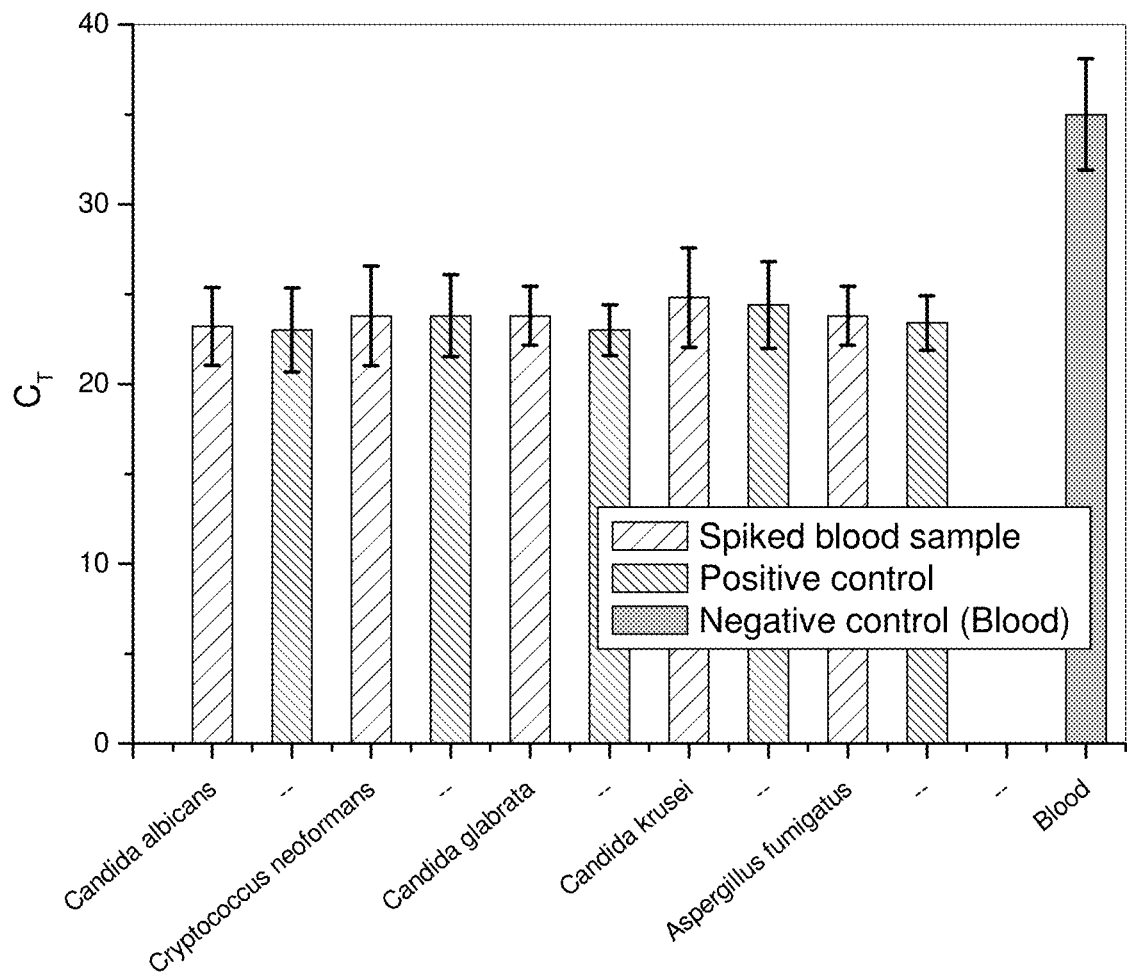
FIG. 27 shows the $C_T$ values for the real-time RT-PCR detection of a single cell of different fungal species in blood samples.

Five pathogenic species were tested: CA (*Candida albicans*), CrN (*Cryptococcus neoformans*), CG (*Candida glabrata*), CK (*Candida krusei*), and AF (*Aspergillus fumigatus*). Spiked blood samples, and positive and negative controls were prepared and subjected to electrical lysis as described above. The RT-PCR protocol used UFF2 forward primer; 5'-ACGGGGAGGTAGTGACAATAAAT-3' (SEQ. ID. 9) and UFR2 reverse primer, 5'-CCCAAGGTTCAAC-TACGAGCTT-3' (SEQ. ID, 10). The 18S rRNA gene fragment of 190 base pairs at a hypervariable region of all fungal species (nucleotide 434 to 624 using *Candida albicans* AB013586 as a reference) was amplified. The resulting $C_T$ values for different species over five independent runs are presented in FIG. 27. The detection limit criterion as described above was satisfied for all fungal species.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

We claim:

1. A method of extracting microbial cells from a sample, the method comprising:
centrifuging, within a vessel, a mixture comprising a sample and a hydrophobic cushioning liquid, such that the cushioning liquid forms a liquid interface below a supernatant, wherein microbial cells from the sample are removed from suspension and collected adjacent to the liquid interface;
withdrawing a substantial quantity of the supernatant without removing the collected microbial cells;
mixing the contents of the vessel and allowing the cushioning liquid to re-establish the liquid interface below a suspension containing the microbial cells; and
extracting a least a portion of the suspension without extracting a substantial portion of the cushioning liquid, thereby obtaining an extracted suspension comprising microbial cells.

2. The method according to claim 1 further wherein the mixture further comprises one or more of a buffer and a reagent.

3. The method according to claim 2 wherein the reagent comprises a lysis reagent effective for lysing one or more non-microbiological cells within the sample.

4. The method according to claim 3 wherein the sample is a blood-containing sample and the lysis reagent is a blood cell lysis reagent.

5. The method according to claim 4 wherein the sample comprises whole blood.

6. The method according to claim 4 wherein the blood cell lysis reagent is an aqueous solution containing saponin in an amount ranging between approximately 1.5 and 80 mg/ml, and sodium polyanetholesulfonate in an amount ranging between approximately 0.5 and 20 mg/ml, expressed in terms of the mixture of blood containing sample and blood cell lysis reagent.

7. The method according to claim 4 wherein the blood cell lysis reagent is an aqueous solution containing saponin in an amount ranging between approximately 10 and 30 mg/ml, and sodium polyanetholesulfonate in an amount ranging between approximately 2.5 and 10 mg/ml, expressed in terms of the mixture of blood containing sample and blood cell lysis reagent.

8. The method according to claim 4 wherein the blood cell lysis reagent is an aqueous solution containing polyethylene glycol tert-octylphenyl ether in an amount ranging between approximately 0.05 and 2.5%, and sodium polyanetholesulfonate in an amount ranging between approximately 5 and 10 mg/ml, expressed in terms of the mixture of blood containing sample and blood cell lysis reagent.

9. The method according to claim 8 wherein the pH of the blood cell lysis reagent is between approximately 5 and 11.

10. The method according to claim 8 wherein the pH of the blood cell lysis reagent is between approximately 9 and 11.

11. The method according to claim 8 wherein polyethylene glycol tert-octylphenyl ether is provided in an amount ranging between approximately 0.5 and 1.5%.

12. The method according to claim 4 wherein the blood cell lysis reagent further comprises an antifoaming agent.

13. The method according to claim 12 wherein the antifoaming agent comprises poly(propylene glycol).

14. The method according to claim 2 wherein the buffer and/or reagent is mixed with the sample within the vessel.

15. The method according to claim 2 wherein the buffer and/or reagent is mixed with the sample prior to adding the sample to the vessel.

16. The method according to claim 1 wherein the sample is selected from the group consisting of a sputum sample, a cerebral spinal fluid sample, a urine sample, and a homogenized stool sample.

17. The method according to claim 1 wherein the sample is one of a food sample and a homogenized food sample.

18. The method according to claim 1 wherein the sample is an environmental sample.

19. The method according to claim 1 wherein the volume of the cushioning liquid is between approximately 2.5 microliters and 100 microliters.

20. The method according to claim 1 wherein the volume of the cushioning liquid is between approximately 5 microliters and 15 microliters.

21. The method according to claim 1 wherein a volume of cushioning liquid is provided such that surface of the vessel that is wetted by the cushioning liquid envelops at least the region of the vessel surface where the microbial cells would sediment under centrifugation in the absence of the cushioning liquid.

22. The method according to claim 1 wherein prior to mixing the contents of the vessel and allowing the cushioning liquid to re-establish the liquid interface below the suspension containing the microbial cells, the following washing steps are performed:
adding a volume of wash buffer to the vessel;
mixing the contents of the vessel;
centrifuging the vessel such that the cushioning liquid forms a liquid interface below a supernatant, and such that microbial cells are transported to and collected at the liquid interface; and
withdrawing a substantial quantity of the supernatant without extracting the collected microbial cells.

23. The method according to claim 22 further comprising performing the washing steps one or more additional times.

24. The method according to claim 1 wherein after centrifugation, the liquid interface is formed on a side portion of the vessel, wherein the method further comprises re-orienting the vessel such that the liquid interface is substantially horizontal, and wherein reorientation of the vessel is performed such that a substantial quantity of the microbial cells remains collected at the liquid interface.

25. The method according to claim 1 further comprising:
lysing the microbial cells within the extracted suspension to obtain a lysate; and
performing at least one assay to detect at least one analyte that may be present in the lysate.

26. The method according to claim 25 wherein the microbial cells are electrically lysed.

27. The method according to claim 26 wherein the microbial cells are electrically lysed according to the steps of:
providing a microfluidic device comprising:
a fluidic channel having an upper channel surface, a lower channel surface, a side wall, and a thickness on a submillimeter scale;
an upper electrode on the upper channel surface; and
a lower electrode on the lower channel surface;
wherein the channel is adapted to support flash heating of the extracted suspension under the application of voltage pulses to the electrodes;
flowing the extracted suspension into the channel; and
applying a series of bipolar voltage pulses between the upper electrode and the lower electrode, wherein an amplitude, pulse width, and duration of the voltage pulses are sufficient to flash heat the extracted suspension and lyse the microbial cells, thereby releasing macromolecules from the microbial cells.

28. The method according to claim 27 wherein the voltage pulses are applied such that Joule heating of the extracted suspension occurs with a rate of at least approximately 250 degrees per second.

29. The method according to claim 27 wherein under application of the voltage pulses, the extracted suspension is heated faster than a timescale of thermal diffusion from the channel.

30. The method according to claim 27 wherein thermal properties of the channel surfaces are selected to such that, in response to applied voltage pulses, Joule heating of the extracted suspension occurs with a rate of at least approximately 2000 degrees per second.

31. The method according to claim 25 wherein at least one of the assays is performed by polymerase chain reaction.

32. The method according to claim 25 wherein at least one of the assays is performed, at least in part, by reverse transcription polymerase chain reaction.

33. The method according to claim 25 wherein at least one of the analytes is rRNA.

34. The method according to claim 25 wherein the microbial cells are bacterial and/or fungal cells.

* * * * *

UNITED STATES PATENT AND TRADEMARK OFFICE
CERTIFICATE OF CORRECTION

PATENT NO. : 10,662,420 B2
APPLICATION NO. : 15/612091
DATED : May 26, 2020
INVENTOR(S) : Talebpour et al.

Page 1 of 1

It is certified that error appears in the above-identified patent and that said Letters Patent is hereby corrected as shown below:

On the Title Page

Item (63), should read:
Continuation of application No. 14/648,161, filed as application No. PCT/CA2013/000992 on Nov. 26, 2013, now Pat. No. 9,707,555 which is a continuation-in-part of application No. 13/833,872, filed on Mar. 15, 2013, now Pat. No. 8,975,060.

Signed and Sealed this
Eleventh Day of August, 2020

Andrei Iancu
*Director of the United States Patent and Trademark Office*

```
                              SEQUENCE LISTING

<160> NUMBER OF SEQ ID NOS: 26

<210> SEQ ID NO 1
<211> LENGTH: 21
<212> TYPE: DNA
<213> ORGANISM: Artificial
<220> FEATURE:
<223> OTHER INFORMATION: Pan bacterial primer

<400> SEQUENCE: 1
cggctaactc cgtgccagca g                                              21

<210> SEQ ID NO 2
<211> LENGTH: 25
<212> TYPE: DNA
<213> ORGANISM: Artificial
<220> FEATURE:
<223> OTHER INFORMATION: Pan bacterial primer

<400> SEQUENCE: 2
atctctacgc atttcaccgc tacac                                          25

<210> SEQ ID NO 3
<211> LENGTH: 23
<212> TYPE: DNA
<213> ORGANISM: Artificial
<220> FEATURE:
<223> OTHER INFORMATION: Pan fungal primer

<400> SEQUENCE: 3 aggggggaggt agtgacaata aat                                           23

<210> SEQ ID NO 4
<211> LENGTH: 20
<212> TYPE: DNA
<213> ORGANISM: Artificial
<220> FEATURE:
<223> OTHER INFORMATION: Pan fungal primer

<400> SEQUENCE: 4
caaagttcaa ctacgagctt                                                20

<210> SEQ ID NO 5
<211> LENGTH: 41
<212> TYPE: DNA
<213> ORGANISM: Artificial
<220> FEATURE:
<223> OTHER INFORMATION: Pan gram negative bacterial  probe

<400> SEQUENCE: 5
ccgagcggtg caagcgttaa tcggaattac tgggcgctcg g                        41

<210> SEQ ID NO 6
<211> LENGTH: 38
<212> TYPE: DNA
<213> ORGANISM: Artificial
<220> FEATURE:
<223> OTHER INFORMATION: Pan fungal probe

<400> SEQUENCE: 6
```

```
ccgagctctg gtgccagcag ccgcggtaat tcgctcgg                            38

<210> SEQ ID NO 7
<211> LENGTH: 19
<212> TYPE: DNA
<213> ORGANISM: Artificial
<220> FEATURE:
<223> OTHER INFORMATION: Pan bacterial primer

<400> SEQUENCE: 7
agagtttgat cctggctag                                                 19

<210> SEQ ID NO 8
<211> LENGTH: 20
<212> TYPE: DNA
<213> ORGANISM: Artificial
<220> FEATURE:
<223> OTHER INFORMATION: Pan bacterial primer

<400> SEQUENCE: 8
taaggttctt cgcgttgctt                                                20

<210> SEQ ID NO 9
<211> LENGTH: 23
<212> TYPE: DNA
<213> ORGANISM: Artificial
<220> FEATURE:
<223> OTHER INFORMATION: Pan fungal primer

<400> SEQUENCE: 9
acggggaggt agtgacaata aat                                            23

<210> SEQ ID NO 10
<211> LENGTH: 22
<212> TYPE: DNA
<213> ORGANISM: Artificial
<220> FEATURE:
<223> OTHER INFORMATION: Pan fungal primer

<400> SEQUENCE: 10
cccaaggttc aactacgagc tt                                             22

<210> SEQ ID NO 11
<211> LENGTH: 20
<212> TYPE: DNA
<213> ORGANISM: Artificial
<220> FEATURE:
<223> OTHER INFORMATION: Pan gram positive bacterial primer

<400> SEQUENCE: 11
atgcatagcc gacctgagag                                                20

<210> SEQ ID NO 12
<211> LENGTH: 19
<212> TYPE: DNA
<213> ORGANISM: Artificial
<220> FEATURE:
<223> OTHER INFORMATION: Pan gram positive bacterial primer

<400> SEQUENCE: 12
agttagccgt ssctttctg                                                 19

<210> SEQ ID NO 13
<211> LENGTH: 20
<212> TYPE: DNA
<213> ORGANISM: Artificial
```

```
<220> FEATURE:
<223> OTHER INFORMATION: Pan gram negative bacterial primer

<400> SEQUENCE: 13
gttacccgca gaagaagcac                                              20

<210> SEQ ID NO 14
<211> LENGTH: 20
<212> TYPE: DNA
<213> ORGANISM: Artificial
<220> FEATURE:
<223> OTHER INFORMATION: Pan gram negative bacterial primer

<400> SEQUENCE: 14
acctgagcgt cagtcttcgt                                              20

<210> SEQ ID NO 15
<211> LENGTH: 22
<212> TYPE: DNA
<213> ORGANISM: Artificial
<220> FEATURE:
<223> OTHER INFORMATION: Pan fungal primer

<400> SEQUENCE: 15
aacgaaagtt aggggatcga ag                                           22

<210> SEQ ID NO 16
<211> LENGTH: 21
<212> TYPE: DNA
<213> ORGANISM: Artificial
<220> FEATURE:
<223> OTHER INFORMATION: Pan fungal primer

<400> SEQUENCE: 16
ctttaagttt cagccttgcg a                                            21

<210> SEQ ID NO 17
<211> LENGTH: 33
<212> TYPE: DNA
<213> ORGANISM: Artificial
<220> FEATURE:
<223> OTHER INFORMATION: Pan fungal probe

<400> SEQUENCE: 17
ccgagccgta gtcttaacca taaactatgc gct                               33

<210> SEQ ID NO 18
<211> LENGTH: 21
<212> TYPE: DNA
<213> ORGANISM: Artificial
<220> FEATURE:
<223> OTHER INFORMATION: Pan bacterial primer

<400> SEQUENCE: 18
gacaggtggt gcatggttgt c                                            21

<210> SEQ ID NO 19
<211> LENGTH: 20
<212> TYPE: DNA
<213> ORGANISM: Artificial
<220> FEATURE:
<223> OTHER INFORMATION: Pan bacterial primer

<400> SEQUENCE: 19
acgtcatccc caccttcctc                                              20
```

<210> SEQ ID NO 20
<211> LENGTH: 42
<212> TYPE: DNA
<213> ORGANISM: Artificial
<220> FEATURE:
<223> OTHER INFORMATION: Pan gram positive bacterial probe

<400> SEQUENCE: 20
ccgagcttag ttgccatcat ttagttgggc actctagctc gg        42

<210> SEQ ID NO 21
<211> LENGTH: 22
<212> TYPE: DNA
<213> ORGANISM: Artificial
<220> FEATURE:
<223> OTHER INFORMATION: Pan gram positive bacterial primer

<400> SEQUENCE: 21
gctcgtgtcg tgagatgttg gg        22

<210> SEQ ID NO 22
<211> LENGTH: 23
<212> TYPE: DNA
<213> ORGANISM: Artificial
<220> FEATURE:
<223> OTHER INFORMATION: Pan gram positive bacterial primer

<400> SEQUENCE: 22
caggtcataa ggggcatgat gat        23

<210> SEQ ID NO 23
<211> LENGTH: 22
<212> TYPE: DNA
<213> ORGANISM: Artificial
<220> FEATURE:
<223> OTHER INFORMATION: Pan gram negative bacterial primer

<400> SEQUENCE: 23
gttacccgca gaagaagcac cg        22

<210> SEQ ID NO 24
<211> LENGTH: 21
<212> TYPE: DNA
<213> ORGANISM: Artificial
<220> FEATURE:
<223> OTHER INFORMATION: Pan gram negative bacterial primer

<400> SEQUENCE: 24
atgcagttcc caggttgagc c        21

<210> SEQ ID NO 25
<211> LENGTH: 22
<212> TYPE: DNA
<213> ORGANISM: Artificial
<220> FEATURE:
<223> OTHER INFORMATION: Pseudomonas aeruginosa primer

<400> SEQUENCE: 25
gggcagtaag ttaatacctt gc        22

<210> SEQ ID NO 26
<211> LENGTH: 22
<212> TYPE: DNA
<213> ORGANISM: Artificial
<220> FEATURE:
<223> OTHER INFORMATION: Pseudomonas aeruginosa primer

```
<400> SEQUENCE: 26
tctacgcatt tcaccgctac ac                                                    22
```